(12) United States Patent
Regina et al.

(10) Patent No.: US 7,812,221 B2
(45) Date of Patent: Oct. 12, 2010

(54) WHEAT WITH ALTERED BRANCHING ENZYME ACTIVITY AND STARCH AND STARCH CONTAINING PRODUCTS DERIVED THEREFROM

(75) Inventors: Ahmed Regina, Ngunnawal ACT (AU); Sadequr Rahman, Nicholls ACT (AU); Matthew Kennedy Morell, Aranda ACT (AU); Zhongyi Li, Kaleen ACT (AU)

(73) Assignees: Commonwealth Scientific and Industrial Research Organization, Campbell (AU); Limagrain Cereales Ingredients S.A., Saint Ignat (FR)

( * ) Notice: Subject to any disclaimer, the term of this patent is extended or adjusted under 35 U.S.C. 154(b) by 360 days.

(21) Appl. No.: 10/881,808

(22) Filed: Jun. 30, 2004

(65) Prior Publication Data

US 2005/0071896 A1    Mar. 31, 2005

Related U.S. Application Data

(60) Provisional application No. 60/484,360, filed on Jul. 1, 2003, provisional application No. 60/484,169, filed on Jun. 30, 2003.

(51) Int. Cl.
| | |
|---|---|
| A01H 5/10 | (2006.01) |
| C12N 15/82 | (2006.01) |
| C12N 15/63 | (2006.01) |
| C12N 15/29 | (2006.01) |
| C12N 15/11 | (2006.01) |
| A23L 1/0522 | (2006.01) |

(52) U.S. Cl. .................. 800/286; 800/285; 800/284; 800/278; 800/295; 800/320.3; 435/320.1; 435/468; 536/23.1; 536/23.2; 536/24.5; 426/578

(58) Field of Classification Search .................. None
See application file for complete search history.

(56) References Cited

U.S. PATENT DOCUMENTS

| | | |
|---|---|---|
| 4,863,655 A | 9/1989 | LaCourse et al. |
| 5,035,930 A | 7/1991 | LaCourse et al. |
| 5,043,196 A | 8/1991 | LaCourse et al. |
| 5,051,271 A | 9/1991 | Iyengar et al. |
| 5,268,367 A | 12/1993 | Miwa et al. |
| 5,281,276 A | 1/1994 | Chiu et al. |
| 5,300,145 A | 4/1994 | Fergason et al. |
| 5,409,542 A | 4/1995 | Henley et al. |
| 5,480,669 A | 1/1996 | Zallie et al. |
| 5,593,503 A | 1/1997 | Shi et al. |
| 5,714,600 A | 2/1998 | McNaught et al. |
| 5,718,770 A | 2/1998 | Shah et al. |
| 5,792,754 A | 8/1998 | Green et al. |
| 5,792,920 A * | 8/1998 | Bridges et al. .............. 800/284 |
| 5,849,090 A | 12/1998 | Haralampu et al. |
| 5,866,793 A | 2/1999 | Baga et al. |
| 5,902,410 A | 5/1999 | Chiu et al. |
| 5,929,052 A | 7/1999 | Brynolf et al. |
| 5,932,017 A | 8/1999 | Chiu et al. |
| 5,977,454 A | 11/1999 | McNaught et al. |
| 5,994,623 A | 11/1999 | Broglie et al. |
| 6,001,628 A | 12/1999 | Kossmann et al. |
| 6,010,574 A | 1/2000 | Jeffcoat et al. |
| 6,043,229 A | 3/2000 | Kettlitz et al. |
| 6,060,050 A | 5/2000 | Brown et al. |
| 6,066,782 A | 5/2000 | Kossmann et al. |
| 6,103,893 A | 8/2000 | Cooke et al. |
| 6,117,665 A | 9/2000 | Kossmann et al. |
| 6,147,279 A | 11/2000 | Poulsen |
| 6,169,226 B1 | 1/2001 | Ek et al. |
| 6,215,042 B1 | 4/2001 | Willmitzer et al. |
| 6,221,350 B1 | 4/2001 | Brown et al. |
| 6,221,420 B1 | 4/2001 | Thomas et al. |
| 6,232,122 B1 | 5/2001 | Poulsen |
| 6,274,567 B1 | 8/2001 | Brown et al. |
| 6,287,621 B1 | 9/2001 | LaCourse et al. |
| 6,348,452 B1 | 2/2002 | Brown et al. |
| 6,352,733 B1 | 3/2002 | Haynes et al. |
| 6,376,749 B1 * | 4/2002 | Broglie et al. .............. 800/284 |
| 6,409,840 B1 | 6/2002 | McNaught et al. |
| 6,423,886 B1 | 7/2002 | Singletary et al. |
| 6,433,253 B1 | 8/2002 | Kossmann et al. |
| 6,451,121 B2 | 9/2002 | Chiu et al. |
| 6,451,367 B1 | 9/2002 | McNaught et al. |
| 6,468,355 B1 | 10/2002 | Thompson et al. |
| 6,469,231 B1 | 10/2002 | Ek et al. |
| 6,528,498 B2 | 3/2003 | Brown et al. |
| 6,566,585 B1 | 5/2003 | Quanz et al. |
| 6,570,066 B1 | 5/2003 | Willmitzer et al. |
| 6,608,018 B1 | 8/2003 | Shinohara et al. |
| 6,613,373 B2 | 9/2003 | Haynes et al. |
| 6,623,943 B2 | 9/2003 | Schmiedel et al. |
| 6,635,454 B1 | 10/2003 | Kossmann et al. |

(Continued)

FOREIGN PATENT DOCUMENTS

EP    0885556    12/1998

(Continued)

OTHER PUBLICATIONS

Tetlow et al 2004. Journal of Experimental Botany 55(406):2131-2145, pp. 2131 and 2135.*

(Continued)

*Primary Examiner*—Anne Marie Grunberg
*Assistant Examiner*—Brent Page
(74) *Attorney, Agent, or Firm*—John P. White; Cooper & Dunham LLP

(57) ABSTRACT

Wheat having a reduced level of SBEIIa activity, that may have a relative high amylose content. Wheat having a mutant SBEIIa gene in the A genome. The wheat might additionally have reduced levels of SBEIIb activity. The wheat grain of this invention can be of a non-shrunken phenotype despite a lesion in the amylopectin synthesis pathway, and may also have a high relative amylose content.

32 Claims, 27 Drawing Sheets

U.S. PATENT DOCUMENTS

| | | | |
|---|---|---|---|
| 6,664,389 B1 | 12/2003 | Shi et al. | |
| 6,696,563 B2 | 2/2004 | Bengs et al. | |
| 6,699,694 B1 | 3/2004 | Buttcher et al. | |
| 6,716,612 B2 | 4/2004 | Kossmann et al. | |
| 6,730,825 B1 | 5/2004 | Goldsbrough et al. | |
| 6,734,340 B2 | 5/2004 | Schewe et al. | |
| 6,734,341 B2 | 5/2004 | Singletary et al. | |
| 6,825,342 B1 | 11/2004 | Cooke et al. | |
| 6,890,571 B2 | 5/2005 | Shi et al. | |
| 6,916,976 B1 * | 7/2005 | Li et al. | 800/320.3 |
| 6,940,001 B1 | 9/2005 | Landschutze | |
| 6,956,148 B1 | 10/2005 | Jobling et al. | |
| 7,001,771 B1 | 2/2006 | Morell | |
| 7,009,092 B1 * | 3/2006 | Jane et al. | 800/320.1 |
| 7,015,318 B2 | 3/2006 | Fuertes et al. | |
| 7,097,831 B1 | 8/2006 | Bengs et al. | |
| 7,217,857 B2 | 5/2007 | Goldsbrough et al. | |
| 7,521,593 B2 | 4/2009 | Regina et al. | |
| 7,667,114 B2 | 2/2010 | Morell et al. | |
| 2001/0000827 A1 | 5/2001 | Yamamori et al. | |
| 2002/0002713 A1 | 1/2002 | Allen et al. | |
| 2002/0138876 A1 | 9/2002 | Block et al. | |
| 2002/0197373 A1 | 12/2002 | Shi et al. | |
| 2002/0198175 A1 | 12/2002 | Brown et al. | |
| 2003/0004332 A1 | 1/2003 | Bengs et al. | |
| 2003/0045504 A1 | 3/2003 | Brown et al. | |
| 2003/0046730 A1 | 3/2003 | Ek et al. | |
| 2003/0054501 A1 | 3/2003 | Schmiedel et al. | |
| 2003/0094172 A1 | 5/2003 | Bengs et al. | |
| 2003/0110534 A1 | 6/2003 | Schewe et al. | |
| 2003/0113429 A1 | 6/2003 | McNaught et al. | |
| 2003/0135883 A1 | 7/2003 | Singletary et al. | |
| 2003/0166919 A1 | 9/2003 | Cooke et al. | |
| 2003/0175931 A1 | 9/2003 | Kossmann et al. | |
| 2003/0200581 A1 | 10/2003 | Yamamori et al. | |
| 2003/0208806 A1 | 11/2003 | Yamamori et al. | |
| 2003/0215561 A1 | 11/2003 | Shi et al. | |
| 2003/0215562 A1 | 11/2003 | Shi et al. | |
| 2003/0219520 A1 | 11/2003 | Shi et al. | |
| 2003/0221220 A1 | 11/2003 | Broglie et al. | |
| 2004/0047963 A1 | 3/2004 | Haynes et al. | |
| 2004/0058890 A1 | 3/2004 | Brown et al. | |
| 2004/0060083 A1 | 3/2004 | Regina et al. | |
| 2004/0068766 A1 | 4/2004 | Poulsen et al. | |
| 2004/0110254 A1 | 6/2004 | Buttcher et al. | |
| 2004/0172679 A1 | 9/2004 | Schewe et al. | |
| 2004/0199942 A1 | 10/2004 | Morell et al. | |
| 2004/0216188 A1 | 10/2004 | Goldsbrough et al. | |
| 2004/0234663 A1 | 11/2004 | Motoi et al. | |
| 2005/0031754 A1 | 2/2005 | Maningat et al. | |
| 2005/0031755 A1 | 2/2005 | Maningat et al. | |
| 2005/0031756 A1 | 2/2005 | Maningat et al. | |
| 2005/0037125 A1 | 2/2005 | Maningat et al. | |
| 2005/0074891 A1 | 4/2005 | Allen et al. | |
| 2005/0177901 A1 | 8/2005 | Zhu et al. | |
| 2006/0010517 A1 | 1/2006 | Li et al. | |
| 2006/0035379 A1 | 2/2006 | Morell et al. | |
| 2006/0130181 A1 | 6/2006 | Hoehne et al. | |
| 2006/0204597 A1 | 9/2006 | Bird et al. | |
| 2006/0286186 A1 | 12/2006 | Bird et al. | |
| 2007/0059431 A1 | 3/2007 | Simon et al. | |
| 2007/0300319 A1 | 12/2007 | Li et al. | |

FOREIGN PATENT DOCUMENTS

| | | |
|---|---|---|
| EP | 1431393 | 6/2004 |
| GB | 2 360 521 | 9/2001 |
| JP | 6261767 | 9/1994 |
| JP | 10004970 | 1/1998 |
| JP | 10014575 | 1/1998 |
| JP | 2000279180 | 10/2000 |
| KR | 20030072094 | 9/2003 |
| KR | 20030091103 | 12/2003 |
| WO | WO 92/11375 | 7/1992 |
| WO | PCT/US96/19678 | 12/1996 |
| WO | WO 98/37214 | 8/1998 |
| WO | WO 98/48610 | 11/1998 |
| WO | WO 99/04649 | 2/1999 |
| WO | WO 00/015810 | 3/2000 |
| WO | WO 0015810 | 3/2000 |
| WO | PCT/AU2000/00385 | 4/2000 |
| WO | WO 00/38528 | 7/2000 |
| WO | PCT/CA00/01276 | 10/2000 |
| WO | WO 00/63399 | 10/2000 |
| WO | PCT/AU01/00175 | 2/2001 |
| WO | WO 01/32886 | 5/2001 |
| WO | PCT/AU01/01452 | 11/2001 |
| WO | PCT/EP02/006265 | 6/2002 |
| WO | PCT/JP02/009221 | 9/2002 |
| WO | WO 02/101059 A2 | 12/2002 |
| WO | WO 03/023024 | 3/2003 |
| WO | WO 03094600 | 11/2003 |
| WO | PCT/AU04/000901 | 6/2004 |
| WO | PCT/AU2004/001517 | 10/2004 |

OTHER PUBLICATIONS

Rahman et al 2001 Plant Physiology 125:1314-1324.*
Thomas et al 2001 The Plant Journal 25:417-425.*
Wolters et al 2000 Plant Molecular Biology 43:377-386.*
Wesley et al 2001 The Plant Journal 27:581-590.*
Notification Concerning Transmittal of International Preliminary Report on Patentability issued Jan. 12, 2006 by The International Bureau of WIPO in connection with PCT International Application No. PCT/AU2004/000901, including a Jan. 3, 2006 International Preliminary Report on Patentability.
Miao, Hongmei et al., (2004) "Evaluation And Characterization of an Endosperm-Specific sbeIIa Promoter in Wheat" *Chinese Science Bulletin*, vol. 49, No. 6, pp. 579-585.
Rahman, Sadequr et al., (2001) "Comparison of Starch-Branching Enzyme Genes Reveals Evolutionary Relationships Among Isoforms. Characterization of a Gene for Starch-Branching Enzyme IIa from the Wheat D Genome Donor *Aegilops tauschii*" *Plant Physiology*, vol. 125, pp. 1314-1324.
Sun, Chuanxin et al., (1998) "The Two Genes Encoding Starch-Branching Enzymes IIa and IIb Are Differently Expressed in Barley" *Plant Physiology*, vol. 118, pp. 37-49.
Abel, G.J.W. et al., "Cloning and functional analysis of a cDNA encoding a novel 139 kDa Starch Synthase from Potato (*Solanum tuberosum* L.)," *Plant J.* 10 (6): 981-991 (1996).
Ainsworth, C. et al., "Expression, organization and structure of the genes encoding the waxy protein (granule-bound starch synthase) in wheat," *Plant Mol. Biol.* 22:67-82 (1993).
Baba, T. et al., "Identification, cDNA cloning and gene expression of soluble starch synthase in rice (*Oryza stativa* L.) Immature Seeds," Plant Physiol. 103:565-573 (1993).
Banks et al., "Studies on Starches of High Amylose Content," *Starch* 26: 289-300 (1974).
Batey and Curtin, "Measurement of Amylose/Amylopectin Ratio by High-Performance Liquid Chromatography," *Starch* 48: 338-344 (1996).
Blauth et al., "Identification of Mutator Insertional Mutants of Starch-Branching Enzyme 2a in Corn," *Plant Physiology* 125:1396-1405 (2001).
Boyer and Preiss, "Evidence for Independent Genetic Control of the Multiple Forms of Maize Endosperm Branching Enzymes and Starch Synthases," *Plant Physiology* 67: 1141-1145 (1981).
Buleon et al., "Starch Granules: Structure and Biosynthesis," *International Journal of Biological Macromolecules* 23: 85-112 (1998).
Craig et al., "Mutations in the Gene Encoding Starch Synthase II Profoundly Alter Amylopectin Structure in Pea Embryos," *The Plant Cell* 10:413-426 (1998).
Denyer, K. et al., "Identification of Multiple Isoforms of Soluble and Granule Bound Starch Synthase in Developing Wheat Endosperm," *Planta* 196: 256-265 (1995).

Dry, I. et al., "Characterization of cDNAs encoding two isoforms of granule-bound synthase which show differential expression in developing storage organs of pea and potato," *Plant J.* 2 (2):193-202 (1992).

Edwards et al., "Biochemical and Molecular Characterization of a Novel Starch Synthase from Potato Tubers," *Plant J.* 8 (2):283-294 (1995).

Flipse et al., "Introduction of Sense and Antisense cDNA for Branching Enzyme in the Amylose-Free Potato Mutant Leads to Physico-Chemical Changes in the Starch," *Planta* 198:340-347 (1996).

Fujita et al., "Grain and Starch Characteristics of the Double Recessive Lines for Amylose-free and High Amylose Gene in Barley," *Breeding Science* 49: 217-219 (1999).

Gao et al., "Triticum aestivum mRNA for Starch Synthase IIa-2 (wSs2a-2." EMBL Abstract Accession No. AJ269503, Jul. 6, 2000.

Gao et al., "Characterization of dull 1, a Maize Gene Coding for a Novel Starch Synthase," *Plant Cell* 10:399-412 (1998).

Gao and Chibbar, "Isolation, Characterization, and Expression Analysis of Starch Synthase IIa cDNA from wheat (*Triticum aestivum* L.)," *Genome* 43:768-775 (2000).

Goering and DeHass, "A Comparison of the Properties of Large-and Small-Granule Starch Isolated from Several Isogenic Lines of Barley," *Cereal Chemistry* 51: 573-578 (1974).

Harn et al., "Isolation and Characterization of the zSSIIA and zSSIIb Starch Synthase cDNA, Clones from Maize Endosperm," *Plant Mol. Biol.* 37:639-649 (1998).

Holmes et al., Henderson's Dictionary of Biological Terms, 9th Ed., Van Nostrand Reinhold Co., New York, 1979, p. 218.

Klosgen, et al., "Molecular Analysis of the Waxy Locus of Zea mays," *Mol. Gen. Genet.* 203: 237-244 (1986).

Knight, et al., "Molecular Cloning of Starch Synthase I from Maize (w64) Endosperm and Expression in *Escherichia coli*," *Plant J.* 14 (5): 613-622 (1998).

Kull et al., "Genetic Engineering of Potato Starch Composition: Inhibition of Amylose Biosynthesis in Tubers from Transgentic Potato Lines by the Expression of Antisense Sequences of the Gene for Granule-bound Starch Synthase," *J. Genet. Breed.* 49:69-76 (1995).

Jansson et al., "Cloning, Characterization and Modification of Genes Encoding Starch Branching Enzymers In Barley." Starch: Structure and Functionality. Royal Society of Chemistry, London, pp. 196-203 (1997).

Jarvi and Eslick, "Shrunken Endosperm Mutants in Barley," *Crop Science* 15:363-366 (1975).

Li et al., "Triticum aestivum Starch Synthase IIA mRNA, Complete cds," EMBL Abstract Accession No. AF155217, Sep. 7, 1999.

Li et al., "The Localization and Expression of the Class II Starch Synthases of Wheat," *Plant Physiology* 120:1147-1155 (1999).

Li et al., "Cloning and Characterization of a Gene Encoding Wheat Starch Synthase I," *Theor. Appl. Genet.* 98:1208-1216 (1999).

Mazzolini et al., "Assaying synthetic ribozymes in plants: high-level expression of a functional hammerhead structure fails to inhibit target gene activity in transiently transformed protoplasts," *Plant Mol. Biol.* 20: 715-731 (1992).

Mizuno et al., "Alteration of the Structural Properties of Starch Components by the Lack of an Isoform of Starch Branching Enzyme in Rice Seeds," *J. Biol. Chem.* 268 (25):19084-19091 (1993).

Morell et al., "The Biochemistry and Molecular Biology of Starch Synthesis in Cereals," *Aust. J. Plant. Physiol.* 22:647-660 (1995).

Morell et al., "Barley sex6 Mutants Lack Starch Synthase iia Activity and Contain a Starch with Novel Properties," *The Plant Journal* 34:173-185 (2003).

Myers et al., "Recent Progress toward Understanding Biosynthesis of the Amylopection Crystal," *Plant Physiology* 122: 989-997 (2000).

Nishi et al., "Biochemical and Genetic Analysis of the Effects of Amylose-Extender Mutation in Rice Endosperm." *Plant Physiology* 127:459-472 (2001).

Nakamura Y., Towards a Better Understanding of the Metabolic Synstem for Amylopectin Biosynthesis in Plants: Rice Endosperm as s Model Tissue. *Plant Cell Physiology* 43 (7):718-725 (2002).

Okagaki R.J., "Nucleotide Sequence of a Long cDNA from the Rice Waxy Gene," *Plant Molecular Biology* 19:513-516 (1992).

Puchta, "Gene Replacement by Homologous Recombination in Plants," *Plant. Mol. Biol.* 48: 173-182 (2002).

Rahman, S. et al., "A Complex Arrangement of Genes at a Starch Branching Enzyme I Locus in the D-genome Donor of Wheat," *Genome* 40:465-474 (1997).

Rahman, S. et al., "The Major Proteins of Wheat Endosperm Starch Granules," *Aust. J. Plant Physiol.* 22:793-803 (1995).

Rahman, S. et al., "Characterisation of a Gene Encoding Wheat Endosperm Starch Branching Enzyme-I," *Theor. Appl. Genet.* 98: 156-163 (1999).

Safford, et al., "Consequences of Antisense RNA Inhibition of Starch Branching Enzyme Activity on Properties of Potato Starch," *Carbohydrate Polymers* 35: 155-168 (1998).

Sathish et al. "Cloning and Anti-Sense RNA Constructs of a Startch Branching Enzyme Gene From Barley Endosperm," Photosynthesis: from Light to Biosphere vol. V. P. Mathis (ed.) pp. 313-316 (1995).

Schondelmaier et al., "Genetical Studies in the Mode of Inheritance and Localization of the amol (High Amylose) Gene in Barley," *Plant Breeding* 109: 274-280 (1992).

Schwall, et al., "Production of Very-High-Amylose Potato Starch by Inhibition of SBE A and B," *Nature Biotechnology* 18: 551-554 (2000).

Shannon and Garwood, "In Starch: Chemistry and Technology," Whistler et al., eds, Academic Press, Orlando, FL, 25-86 (1984).

Sidebottom, et al., "Characterization of the Difference of Starch Branching Enzyme Activities in Normal and Low-Amylopectin Maize during Kernel Development," *Journal of Cereal Science* 27:279-287 (1998).

Sun et al., "Identification of Four Starch-Branching Enzymes in Barley Endosperm: Partial Purification of forms I, IIa and IIb," *New Phytol.* 137:215-222 (1997).

Sundberg et al., "Glycaemic Responses and Hyopcholesterolaemic Effects of High-Amylose Barley Diets on Broiler Chicks," *J. Sci. Food Agric.* 76: 457-463 (1998).

Takaoka, M. 'et al., "Structural characterization of high molecular weight starch granule-bound proteins in wheat (*Triticum aestivum* L.)," *J. Agric. Food Chem.* 45: 2929-2934 (1997).

Terada at al., "Efficient Gene Targeting by Homologous Recombination in Rice," *Nature Biotech.* 20: 1030-1034 (1997).

Thomas, et al., "Size Constraints for Targeting Post- Transcriptional Gene Silencing and for RNA-directed Mehtylation in *Nicotiana benthamiana* Using a Potato Virus X Vector," *Plant J.* 25: 417-425 (2001).

Van der Leij et al., "Sequence of the Structural Gene for Granule-Bound Starch Synthase of Potato (*Solanum tuberosum* L.) and Evidence for a Single Point Deletion in the amfallele," *Mol. Gen. Genet.* 228: 240-248 (1991).

Vrinten and Nakamura, "Wheat Granule-Bound Starch Synthase I and II Are Encoded by Separate Genes. That Are Expressed in Different Tissues," *Plant Physiology* 122:255-263 (2000).

USDA, ARS, National Genetic Resources Program. Germplasm Resources Information Network (GRIN) [Online Database] National Germplasm Resources Laboratory, Beltsville, Maryland (http://www.ars-grin.gov/npgs/), GRIN System Accession No. GSHO 2476, Jun. 23, 1997).

Walker and Meritt, "Genetic Control of Abnormal Starch Granules and High Amylose Content in a Mutant of Glacier Barley," *Nature* 221:482-484 (1969).

Yamamori et al., "Genetic Elimination of a Starch Granule Protein, SGP-1, of Wheat Generates an Altered Starch with Apparent High Amylose," *Theor. Appl. Genet.* 101:21-29 (2000).

Yamamori and Endo, "Variation of Starch Granule Proteins and Chromosome Mapping of Their Coding Genes in Common Wheat," Theor. Appl. Genet. 93: 275-181 (1996).

Yamamori, "Selection of a Wheat Lacking a Putative Enzyme for Starch Synthesis, SGP-1," Proc. 9th In Wheat Gen. Symp. 4:300-302 (1998).

Abel et al., GenBank Accession #Y10416 (Jan. 1997) S. Tuberosum mRNA for Soluble Starch Synthase.

Bhullar et al., GenBank Accession #CAB40374 (Apr. 1999) Starch synthase isoform SS III [*Vigna unguiculata*].

Block et al., GenBank Accession #U48227 (Jun. 1996) *Triticum aestivum* soluble starch synthase mRNA, partial cds.

D'Hulst et al., GenBank Accession #AAC17969 (Nov. 2001) Granule-bound starch synthase I precursor [*Chlamydomonas reinhardtii*].
Gao et al., GenBank Accession #AAC14014 (Apr. 1998) Starch synthase DULL 1 [*Zea mays*].
Gao et al., GenBank Accession #AAC14015 (Apr. 1998) Starch synthase DULL 1 [*Zea mays*].
Gao et al., GenBank Accession #CAB86618 (Apr. 2002) Starch synthase IIa-1 [*Triticum aestivum*].
Gao et al., GenBank Accession #AJ26502 (Apr. 2002) *Triticum aestivum* mRNA for starch synthase IIa-1 (wSs2a-1 gene).
Rahman et al., GenBank Accession #AF076680 (May 1999) *Aegilops tauschii* starch branching enzyme-I (SBE-I) gene, complete cds.
Walter et al., GenBank Accession #AAB17085 (Oct. 1996) Starch Synthase.
Walter et al., GenBank Accession #U66377 (Oct. 1996) *Triticum aestivum* soluble starch synthase mRNA; partial cds.
Complete file history for U.S. Patent No. 6,916,976, B1, issued Jul. 12, 2005 (U.S. Appl. No. 09/508,377, filed Jun. 9, 2000; Li et al.).
Advisory Action issued Dec. 17, 2003 in connection with U.S. Appl. No. 09/508,377, filed Jun. 9, 2000.
Amendment and Request for Continued Examination submitted Mar. 31, 2004 in connection with U.S. Appl. No. 09/508,377, filed Jun. 9, 2000.
Amendment submitted Apr. 24, 2003 in connection with U.S. Appl. No. 09/508,377, filed Jun. 9, 2000.
Amendment submitted Nov. 18, 2004 in connection with U.S. Appl. No. 09/508,377, filed Jun. 9, 2000.
Amendment submitted Nov. 3, 2003 in connection with U.S. Appl. No. 09/508,377, filed Jun. 9, 2000.
Amendment submitted Nov. 3, 2003 initialed by the Examiner in connection with U.S. Appl. No. 09/508,377, filed Jun. 9, 2000.
Examiner Interview Summary issued Feb. 8, 2005 in connection with U.S. Appl. No. 09/508,377, filed Jun. 9, 2000.
Final Office Action issued Jul. 2, 2003 in connection with U.S. Appl. No. 09/508,377, filed Jun. 9, 2000.
Notice of Allowance issued Feb. 8, 2005 in connection with U.S. Appl. No. 09/508,377, filed Jun. 9, 2000.
Office Action issued Jun. 18, 2004 in connection with U.S. Appl. No. 09/508,377, filed Jun. 9, 2000.
Office Action issued Oct. 24, 2002 in connection with U.S. Appl. No. 09/508,377, filed Jun. 9, 2000.
Preliminary Amendment submitted Feb. 19, 2002 in connection with U.S. Appl. No. 09/508,377, filed Jun. 9, 2000.
Preliminary Amendment submitted Mar. 10, 2000 in connection with U.S. Appl. No. 09/508,377, filed Jun. 9, 2000.
Response to Restriction Requirement submitted Jul. 22, 2002 in connection with U.S. Appl. No. 09/508,377, filed Jun. 9, 2000.
Restriction Requirement issued Mar. 22, 2002 in connection with U.S. Appl. No. 09/508,377, filed Jun. 9, 2000.
Amendment and Request for Continued Examination submitted Jan. 11, 2008 in connection with U.S. Appl. No. 10/434,893, filed May 9, 2003.
Amendment submitted Apr. 19, 2007 in connection with U.S. Appl. No. 10/434,893, filed May 9, 2003.
Amendment submitted Aug. 4, 2008 in connection with U.S. Appl. No. 10/434,893, filed May 9, 2003.
Amendment submitted Mar. 14, 2006 in connection with U.S. Appl. No. 10/434,893, filed May 9, 2003.
Complete file history for U.S. Patent No. 7,521,593 B2, issued Apr. 21, 2009 (U.S. Appl. No. 10/434,893, filed May 9, 2002; Regina et al.).
Examiner Interview Summary issued Dec. 3, 2008 in connection with U.S. Appl. No. 10/434,893, filed May 9, 2003.
Final Office Action issued Jul. 11, 2007 in connection with U.S. Appl. No. 10/434,893, filed May 9, 2003.
Notice of Allowance issued Dec. 3, 2008 in connection with U.S. Appl. No. 10/434,893, filed May 9, 2003.
Office Action issued Apr. 3, 2008 in connection with U.S. Appl. No. 10/434,893, filed May 9, 2003.
Office Action issued Oct. 19, 2006 in connection with U.S. Appl. No. 10/434,893, filed May 9, 2003.
Response submitted Nov. 17, 2003 in connection with U.S. Appl. No. 10/434,893, filed May 9, 2003.
Response to Restriction Requirement submitted Aug. 7, 2006 in connection with U.S. Appl. No. 10/434,893, filed May 9, 2003.
Restriction Requirement issued Feb. 14, 2006 in connection with U.S. Appl. No. 10/434,893, filed May 9, 2003.
Restriction Requirement issued May 5, 2006 in connection with U.S. Appl. No. 10/434,893, filed May 9, 2003.
Amendment submitted Aug. 19, 2008 in connection with U.S. Appl. No. 11/144,630, filed Jun. 6, 2005.
Amendment submitted Jun. 18, 2007 in connection with U.S. Appl. No. 11/144,630, filed Jun. 6, 2005.
Amendment submitted Mar. 25, 2008 in connection with U.S. Appl. No. 11/144,630, filed Jun. 6, 2005.
Office Action issued Dec. 11, 2008 in connection with U.S. Appl. No. 11/144,630, filed Jun. 6, 2005.
Office Action issued Sep. 26, 2007 in connection with U.S. Appl. No. 11/144,630, filed Jun. 6, 2005.
Preliminary amendment submitted Jun. 6, 2005 in connection with U.S. Appl. No. 11/144,630, filed Jun. 6, 2005.
Restriction Requirement issued May 17, 2007 in connection with U.S. Appl. No. 11/144,630, filed Jun. 6, 2005.
Chuang CF, Meyerowitz EM., "Specific and heritable genetic interference by double-stranded RNA in *Arabidopsis thaliana*." Proc Natl Acad Sci U S A. Apr. 25, 2000;97(9): 4985-90.
Levin JZ et al., Methods of double-stranded RNA-mediated gene inactivation in *Arabidopsis* and their use to define an essential gene in *Methionine biosynthesis. Plant Mol Biol*. Dec. 2000;44 (6):759-75.
Sun et al., "The Two Genes Encoding Starch-Branching Enzymes IIa and IIb Are Differentially Expressed in Barley," *Plant Physiology* 118:37-49 (1998).
Non-Final Office Action issued Apr. 4, 2007 in connection with U.S. Appl. No. 10/204,347.
Response to Apr. 4, 2007 Non-Final Office Action in connection with U.S. Appl. No. 10/204,347.
Non-Final Office Action issued Oct. 18, 2007 in connection with U.S. Appl. No. 10/204,347.
Response to Oct. 18, 2007 Non-Final Office Action in connection with U.S. Appl. No. 10/204,347.
Non-Final Office Action issued May 12, 2008 in connection with U.S. Appl. No. 10/204,347.
Response to May 12, 2008 Non-Final Office Action in connection with U.S. Appl. No. 10/204,347.
Final Office Action issued Mar. 13, 2009 in connection with U.S. Appl. No. 10/204,347.
Response to Mar. 13, 2009 Final Office Action in connection with U.S. Appl. No. 10/204,347.
Notice of Allowance issued Oct. 2, 2009 in connection with U.S. Appl. No. 10/204,347.
Australian Patent Application No. 2004252186 B2.
Examiner's First Report on Australian Patent Application No. 2004252186, issued Jun. 23, 2008.
Sep. 29, 2009 Response to Jun. 23, 2008 Examiner's First Report on Australian Patent Application No. 2004252186.
Examiner's Second Report on Australian Patent Application No. 2004252186, issued Oct. 19, 2009.
Jan. 12, 2010 Response to Oct. 19, 2009 Examiner's Second Report on Australian Patent Application No. 2004252186.
Notice of Acceptance, issued Feb. 12, 2010 in connection with Australian Patent Application No. 2004252186.
Office Action issued Apr. 30, 2009 in connection with Canadian Patent Application No. 2,530,874.
Response to Apr. 30, 2009 Office Action in connection with Canadian Patent Application No. 2,530,874.
Communication Pursuant to Article 94(3) EPC issued Apr. 14, 2008 in connection with European Patent Application No. 04737522.5.
Response to Apr. 14, 2008 Communication Pursuant to Article 94(3) EPC filed Oct. 23, 2008 in connection with European Patent Application No. 04737522.6.
Communication Pursuant to Article 94(3) EPC issued Nov. 12, 2009 in connection with European Patent Application No. 04737522.5.

Response to Nov. 12, 2009 Communication Pursuant to Article 94(3) EPC filed Jan. 4, 2010 in connection with European Patent Application No. 04737522.6.

Summons to Oral Proceedings, issued May 18, 2010 in connection with European Patent Application No. 04737522.5.

Notice of Reasons for Rejection issued May 12, 2010 in connection with Japanese Patent Application No. 2006-517898.

Examination Report issued Aug. 28, 2007 in connection with New Zealand Patent Application No. 544439.

Feb. 27, 2009 Response to Examination Report in connection with New Zealand Patent Application No. 544439.

Examination Report issued Mar. 19, 2009 in connection with New Zealand Patent Application No. 544439.

May 29, 2009 Response to Examination Report issued Mar. 19, 2009 in connection with New Zealand Patent Application No. 544439.

Examination Report issued Jun. 10, 2009 in connection with New Zealand Patent Application No. 544439.

Response to Jun. 10, 2009 Examination Report in connection with New Zealand Patent Application No. 544439.

Examination Report and Notice of Acceptance, issued Oct. 12, 2009 in connection with New Zealand Patent Application No. 544439.

Certificate of Grant issued Mar. 11, 2010 in connection with New Zealand Patent Application No. 544439.

First Examination Report issued Jun. 12, 2008 in connection with Indian Patent Application No. 6084/DELNP/2005.

Response to Jun. 12, 2008 First Examination Report in connection with Indian Patent Application No. 6084/DELNP/2005.

Patent Certificate issued Jun. 1, 2009 in connection with Indian Patent Application No. 234483.

Notification issued Feb. 14, 2008 in connection with Russian Patent Application No. 2006102494/13, including English translation.

Response to Feb. 14, 2008 Office Action in connection with Russian Patent Application No. 2006102494/13, including English translation of claims.

Official Action issued Aug. 14, 2008 in connection with Russian Patent Application No. 2006102494/13, including English translation.

Response to Aug. 14, 2008 Official Action in connection with Russian Patent Application No. 2006102494/13, including English translation of claims.

Official Action issued Feb. 10, 2009 in connection with Russian Patent Application No. 2006102494/13, including English translation.

Response to Feb. 10, 2009 Official Action in connection with Russian Patent Application No. 2006102494/13, including English translation of claims.

English Translation of Decision on Grant issued in connection with Russian Patent Application No. 2006102494/13.

First Notification of Office Action issued Mar. 7, 2008 in connection with Chinese Patent Application No. 200480018658X, with English translation.

Response to First Notification of Office Action issued Mar. 7, 2008 in connection with Chinese Patent Application No. 20040018658X.

Second Notification of Office Action issued Sep. 25, 2009 in connection with Chinese Patent Application No. 200480018658X, with English translation.

Response to Second Notification of Office Action issued Sep. 25, 2009 in connection with Chinese Patent Application No. 200480018658X.

Official Action issued Feb. 5, 2009 in connection with Ukrainian Patent Application No. 200600767, with English translation.

Response to Feb. 5, 2009 Official Action in connection with Ukrainian Patent Application No. 200600767, with English translation of claims.

Decision on Grant in connection with Ukrainian Patent Application No. 200600767, with English translation.

Ukrainian Patent No. 88268 Certificate of Grant.

Certificate of Grant issued Jan. 31, 2007 in connection with South African Patent Application No. 2005/10474.

Tester, T.F. "Influence of growth conditions on barley starch properties." (1997) Biological Macromolecules 21:37-45.

* cited by examiner

Figure 1. Sequence of the Starch Branching Enzyme IIa gene (wSBE II-D1)
from *A. tauschii*

```
   1 AGAAACACCT CCATTTTAGA TTTTTTTTTT GTTCTTTTCG GACGGTGGGT
  51 CGTGGAGAGA TTAGCGTCTA GTTTTCTTAA AAGAACAGGC CATTTAGGCC
 101 CTGCTTTACA AAAGGCTCAA CCAGTCCAAA ACGTCTGCTA GGATCACCAG
 151 CTGCAAAGTT AAGCGCGAGA CCACCAAAAC AGGCGCATTC GAACTGGACA
 201 GACGCTCACG CAGGAGCCCA GCACCACAGG CTTGAGCCTG ACAGCGGACG
 251 TGAGTGCGTG ACACATGGGG TCATCTATGG GCGTCGGAGC AAGGAAGAGA
 301 GACGCACATG AACACCATGA TGATGCTATC AGGCCTGATG GAGGGAGCAA
 351 CCATGCACCT TTTCCCCTCT GGAAATTCAT AGCTCACACT TTTTTTTAAT
 401 GGAAGCAAGA GTTGGCAAAC ACATGCATTT TCAAACAAGG AAAATTAATT
 451 CTCAAACCAC CATGACATGC AATTCTCAAA CCATGCACCG ACGAGTCCAT
 501 GCGAGGTGGA AACGAAGAAC TGAAAATCAA CATCCCAGTT GTCGAGTCGA
 551 GAAGAGGATG ACACTGAAAG TATGCGTATT ACGATTTCAT TTACATACAT
 601 GTACAAATAC ATAATGTACC CTACAATTTG TTTTTTGGAG CAGAGTGGTG
 651 TGGTCTTTTT TTTTTACACG AAAATGCCAT AGCTGGCCCG CATGCGTGCA
 701 GATCGGATGA TCGGTCGGAG ACGACGGACA ATCAGACACT CACCAACTGC
 751 TTTTGTCTGG GACACAATAA ATGTTTTTGT AAACAAAATA AATACTTATA
 801 AACGAGGGTA CTAGAGGCCG CTAACGGCAT GGCCAGGTAA ACGCGCTCCC
 851 AGCCGTTGGT TTGCGATCTC GTCCTCCCGC ACGCAGCGTC GCCTCCACCG
 901 TCCGTCCGTC GCTGCCACCT CTGCTGTGCG CGCGCACGAA GGGAGGAAGA
 951 ACGAACGCCG CACACACACT CACACACGGC ACACTCCCCG TGGGTCCCCT
1001 TTCCGGCTTG GCGTCTATCT CCTCTCCCCC GCCCATCCCC ATGCACTGCA
1051 CCGTACCCGC CAGCTTCCAC CCCCGCCGCA CACGTTGCTC CCCCTTCTCA
1101 TCGCTTCTCA ATTAATATCT CCATCACTCG GGTTCCGCGC TGCATTTCGG
1151 CCGGCGGGTT GAGTGAGATC TGGGCGACTG GCTGACTCAA TCACTACGCG
1201 GGGATGGCGA CGTTCGCGGT GTCCGGCGCG ACTCTCGGTG TGGCGCGGGC
1251 CGGCGTCGGA GTGGCGCGGG CCGGCTCGGA GCGGAGGGGC GGGGCGGACT
1301 TGCCGTCGCT GCTCCTCAGG AAGAAGGACT CCTCTCGTAC GCCTCGCTCT
1351 CTCGAATCTC CCCCGTCTGG CTTTGGCTCC CCTTCTCTCT CCTCTGCGCG
1401 CGCATGGCCT GTTCGATGCT GTTCCCCAAT TGATCTCCAT GAGTGAGAGA
1451 GATAGCTGGA TTAGGCGATC GCGCTTCCTG AACCTGTATT TTTTCCCCCG
1501 CGGGGAAATG CGTTAGTGTC ACCCAGGCCC TGGTGTTACC ACGGCTTTGA
1551 TCATTCCTCG TTTCATTCTG ATATATATTT TCTCATTCTT TTTCTTCCTG
1601 TTCTTGCTGT AACTGCAAGT TGTGGCGTTT TTTCACTATT GTAGTCATCC
1651 TTGCATTTTG CAGGCGCCGT CCTGAGCCGC GCGGCCTCTC CAGGGAAGGT
1701 CCTGGTGCCT GACGGCGAGA GnGACGACTT GGCAAGTCCG GCGCAACCTG
1751 AAGAATTACA GGTACACACA CTCGTGCCGG TAAATCTTCA TACAATCGTT
1801 ATTCACTTAC CAAATGCCGG ATGAAACCAA CCACGGATGC GTCAGGTTTC
1851 GAGCTTCTTC TATCAGCATT GTGCAGTACT GCACTGCCTT GTTCATTTTG
1901 TTAGCCTTGG CCCCGTGCTG GCTCTTGGGC CACTGAAAAA ATCAGATGGA
1951 TGTGCATTCT AGCAAGAACT TCACAACATA ATGCACCGTT TGGGGTTTCG
2001 TCAGTCTGCT CTACAATTGC TATTTTTCGT GCTGTAGATA CCTGAAGATA
2051 TCGAGGAGCA AACGGCGGAA GTGAACATGA CAGGGGGGAC TGCAGAGAAA
2101 CTTCAATCTT CAGAACCGAC TCAGGGCATT GTGGAAACAA TCACTGATGG
2151 TGTAACCAAA GGAGTTAAGG AACTAGTCGT GGGGGAGAAA CCGCGAGTTG
2201 TCCCAAAACC AGGAGATGGG CAGAAAATAT ACGAGATTGA CCCAACACTG
2251 AAAGATTTTC GGAGCCATCT TGACTACCGG TAATGCCTAC CCGCTGCTTT
2301 CGCTCATTTT GAATTAAGGT CCTTTCATCA TGCAAATTTG GGAACATCA
2351 AAGAGACAAA GACTAGGGAC CACCATTTCA TACAGATCCC TTCGTGGTCT
2401 GAGAATATGC TGGGAAGTAA ATGTATAATT GATGGCTACA ATTTGCTCAA
2451 AATTGCAATA CGAATAACTG TCTCCGATCA TTACAATTAA AGAGTGGCAA
2501 ACTGATGAAA ATGTGGTGGA TGGGTTATAG ATTTTACTTT GCTAATTCCT
2551 CTACCAAATT CCTAGGGGGG AAATCTACCA GTTGGGAAAC TTAGTTTCTT
2601 ATCTTTGTGG CCTTTTTGTT TTGGGGAAAA CACATTGCTA AATTCGAATG
2651 ATTTTGGGTA TACCTCGGTG GATTCAACAG ATACAGCGAA TACAAGAGAA
2701 TTCGTGCTGC TATTGACCAA CATGAAGGTG GATTGGAAGC ATTTTCTCGT
2751 GGTTATGAAA AGCTTGGATT TACCCGCAGG TAAATTTAAA GCTTTATTAT
2801 TATGAAACGC CTCCACTAGT CTAATTGCAT ATCTTATAAG AAAATTTATA
```

Figure 1 continued

```
2851  ATTCCTGTTT TCCCCTCTCT TTTTTCCAGT GCTGAAGGTA TCGTCTAATT
2901  GCATATCTTA TAAGAAAATT TATATTCCTG TTTTCCCCTA TTTTCCAGTG
2951  CTGAAGGTAT CACTTACCGA GAATGGGCTC CCTGGAGCGC ATGTTATGTT
3001  CTTTTAAGTT CCTTAACGAG ACACCTTCCA ATTTATTGTT AATGGTCACT
3051  ATTCACCAAC TAGCTTACTG GACTTACAAA TTAGCTTACT GAATACTGAC
3101  CAGTTACTAT AAATTTATGA TCTGGCTTTT GCACCCTGTT ACAGTCTGCA
3151  GCATTAGTAG GTGACTTCAA CAATTGGAAT CCAAATGCAG ATACTATGAC
3201  CAGAGTATGT CTACAGCTTG GCAATTTTCC ACCTTTGCTT CATAACTACT
3251  GATACATCTA TTTGTATTTA TTTAGCTGTT TGCACATTCC TTAAAGTTGA
3301  GCCTCAACTA CATCATATCA AAATGGTATA ATTTGTCAGT GTCTTAAGCT
3351  TCAGCCCAAA GATTCTACTG AATTTAGTCC ATCTTTTTGA GATTGAAAAT
3401  GAGTATATTA AGGATGAATG AATACGTGCA ACACTCCCAT CTGCATTATG
3451  TGTGCTTTTC CATCTACAAT GAGCATATTT CCATGCTATC AGTGAAGGTT
3501  TGCTCCTATT GATGCAGATA TTTGATATGG TCTTTTCAGG ATGATTATGG
3551  TGTTTGGGAG ATTTTCCTCC CTAACAACGC TGATGGATCC TCAGCTATTC
3601  CTCATGGCTC ACGTGTAAAG GTAAGCTGGC CAATTATTTA GTCGAGGATG
3651  TAGCATTTTC GAACTCTGCC TACTAAGGGT CCCTTTTCCT CTCTGTTTTT
3701  TAGATACGGA TGGATACTCC ATCCGGTGTG AAGGATTCAA TTTCTGCTTG
3751  GATCAAGTTC TCTGTGCAGG CTCCAGGTGA AATACCTTTC AATGGCATAT
3801  ATTATGATCC ACCTGAAGAG GTAAGTATCG ATCTACATTA CATTATTAAA
3851  TGAAATTTCC AGTGTTACAG TTTTTTAATA CCCACTTCTT ACTGACATGT
3901  GAGTCAAGAC AATACTTTTG AATTTGGAAG TGACATATGC ATTAATTCAC
3951  CTTCTAAGGG CTAAGGGCA ACCAACCTTG GTGATGTGTG TATGCTTGTG
4001  TGTGACATAA GATCTTATAG CTCTTTTATG TGTTCTCTGT TGGTTAGGAT
4051  ATTCCATTTT GGCCTTTTGT GACCATTTAC TAAGGATATT TACATGCAAA
4101  TGCAGGAGAA GTATGTCTTC CAACATCTCA ACTAAACGAC CAGAGTCACT
4151  AAGGATTTAT GAATCACACA TTGGAATGAG CAGCCCGGTA TGTCAATAAG
4201  TTATTTCACC TGTTTCTGGT CTGATGGTTT ATTCTATGGA TTTTCTAGTT
4251  CTGTTATGTA CTGTTAACAT ATTACATGGT GCATTCACTT GACAACCTCG
4301  ATTTTATTTT CTAATGTCTT CATATTGGCA AGTGCAAAAC TTTGCTTCCT
4351  CTTTGTCTGC TTGTTCTTTT GTCTTCTGTA AGATTTCCAT TGCATTTGGA
4401  GGCAGTGGGC ATGTGAAAGT CATATCTATT TTTTTTTTGT CAGAGCATAG
4451  TTATATGAAT TCCATTGTTG TTGCAATAGC TCGGTATAAT GTAACCATGT
4501  TACTAGCTTA AGATTTCCCA CTTAGGATGT AAGAAATATT GCATTGGAGC
4551  GTCTCCAGCA AGCCATTTCC TACCTTATTA ATGAGAGAGA GACAAGGGGG
4601  GGGGGGGGGG GGGGGTTCCC TTCATTATTC TGCGAGCGAT TCAAAAACTT
4651  CCATTGTTCT GAGGTGTACG TACTGCAGGG ATCTCCCATT ATGAAGAGGA
4701  TATAGTTAAT TCTTTGTAAC CTACTTGGAA ACTTGAGTCT TGAGGCATCG
4751  CTAATATATA CTATCATCAC AATACTTAGA GGATGCATCT GAAnATTTTA
4801  GTGTGATCTT GCACAGGAAC CGAAGATAAA TTCATATGCT AATTTTAGGG
4851  ATGAGGTGTT GCCAAGAATT AAAAGGCTTG GATACAATGC AGTGCAGATA
4901  ATGGCAATCC AGGAGCATTC ATACTATGCA AGCTTTGGGT ATTCACACAA
4951  TCCATTTTTT TCTGTATACA CnTCTTCACC CATTTGGAGC TATTACATCC
5001  TAATGCTTCA TGCACATAAA ATATTTGGAT ATAATCCTTT ATTAGATATA
5051  TAGTACAACT ACACTTAGTA TTCTGAnnAA nAAGATCATT TTATTGTTGT
5101  TGGCTTGTTC CAGGTACCAT GTTACTAATT TTTTGCACC AAGTAGCCGT
5151  TTTGGAACTC CAGAGGACTT AAAATCCTTG ATCGATAGAG CACATGAGCT
5201  TGGTTTGCTT GTTCTTATGG ATATTGTTCA TAGGTAATTA GTCCAATTTA
5251  ATTTTAGCTG TTTTACTGTT TATCTGGTAT TCTAAAGGGA AATTCAGGCA
5301  ATTATGATAC ATTGTCAAAA GCTAAGAGTG GCGAAAGTGA AATGTCAAAA
5351  TCTAGAGTGG CATAAGGAAA ATTGGCAAAA ACTAGAGTGG CAAAAATAAA
5401  ATTTTCCCAT CCTAAATGGC AGGGCCCTAT CGCCGAATAT TTTTCCATTC
5451  TATATAATTG TGCTACGTGA CTTCTTTTTT CTCAGATGTA TTAAACCAGT
5501  TGGACATGAA ATGTATTTGG TACATGTAGT AAACTGACAG TTCCATAGAA
5551  TATCGTTTTG TAATGGCAAC ACAATTTGAT GCCATAGATG TGGATTGAGA
5601  AGTTCAGATG CTATCAATAG AATTAATCAA CTGGCCATGT ACTCGTGGCA
5651  CTACATATAG TTTGCAAGTT GGAAAACTGA CAGCAATACC TCACTGATAA
5701  GTGGCCAGGC CCCACTTGCC AGCTTCATAC TAGATGTTAC TTCCCTGTTG
5751  AATTCATTTG AACATATTAC TTAAAGTTCT TCATTTGTCC TAAGTCAAAC
5801  TTCTTTAAGT TTGACCAAGT CTATTGGAAA ATATATCAAC ATCTACAACA
5851  CCAAATTACT TTGATCAGAT TAACAATTTT TATTTTATTA TATTAGCACA
```

Figure 1 continued

```
5901  TCTTTGATGT TGTAGATATC AGCACATTTT TCTATAGACT TGGTCAAATA
5951  TAGAGAAGTT TGACTTAGGA CAAATCTAGA ACTTCAATCA ATTTGGATCA
6001  GAGGGAACAT CAAATAATAT AGATAGATGT CAACACTTCA ACAAAAAAAT
6051  CAGACCTTGT CACCATATAT GCATCAGACC ATCTGTTTGC TTTAGCCACT
6101  TGCTTTCATA TTTATGTGTT TGTACCTAAT CTACTTTTCC TTCTACTTGG
6151  TTTGGTTGAT TCTATTTCAG TTGCATTGCT TCATCAATGA TTTTGTGTAC
6201  CCTGCAGTCA TTCGTCAAAT AATACCCTTG ACGGTTTGAA TGGTTTCGAT
6251  GGCACTGATA CACATTACTT CCACGGTGGT CCACGCGGCC ATCATTGGAT
6301  GTGGGATTCT CGTCTATTCA ACTATGGAG TTGGAAGTA TGTAGCTCTG
6351  ACTTCTGTCA CCATATTTGG CTAACTGTTC CTGTTAATCT GTTCTTACAC
6401  ATGTTGATAT TCTATTCTTA TGCAGGTATT GAGATTCTTA CTGTCAAACG
6451  CGAGATGGTG GCTTGAAGAA TATAAGTTTG ATGGATTTCG ATTTGATGGG
6501  GTGACCTCCA TGATGTATAC TCACCATGGA TTACAAGTAA GTCATCAAGT
6551  GGTTTCAGTA ACTTTTTTAG GGCACTGAAA CAATTGCTAT GCATCATAAC
6601  ATGTATCATG ATCAGGACTT GTGCTACGGA GTCTTAGATA GTTCCCTAGT
6651  ATGCTTGTAC AATTTTACCT GATGAGATCA TGGAAGATTG GAAGTGATTA
6701  TTATTTATTT TCTTTCTAAG TTTGTTTCTT GTTCTAGATG ACATTTACTG
6751  GGAACTATGG CGAATATTTT GGATTTGCTA CTGATGTTGA TGCGGTAGTT
6801  TACTTGATGC TGGTCAACGA TCTAATTCAT GGACTTTATC CTGATGCTGT
6851  ATCCATTGGT GAAGATGTAA GTGCTTACAG TATTTATGAT TTTTAACTAG
6901  TTAAGTAGTT TTATTTTGGG GATCAGTCTG TTACACTTTT TGTTAGGGGT
6951  AAAATCTCTC TTTTCATAAC AATGCTAATT TATACCTTGT ATGATAATGC
7001  ATCACTTAnG TAATTTGAAA AGTGCAAGGG CATTCAAGCT TACGAGCATA
7051  TTTTTTGATG GCTGTAATTT ATTTGATAGT ATGCTTGTTT GGGTTTTTCA
7101  ATAAGTGGGA GTGTGTGACT AATGTTGTAT TATTTATTTA ATTGCGGAAG
7151  AAATGGGCAA CCTTGTCAAT TGCTTCAGAA GGCTAACTTT GATTCCATAA
7201  ACGCTTTGGA AATGAGAGGC TATTCCCAAG GACATGAATT ATACTTCAGT
7251  GTGTTCTGTA CATGTATTTG TAATAGTGGT TTAACTTAAA TTCCTGCACT
7301  GCTATGGAAT CTCACTGTAT GTTGTnAGTG TACACATCCA CAAACAAGTA
7351  ATCCTGAGCT TTCAACTCAT GAGAAAATAn GAnGTCCGCT TCTGCCAGCA
7401  TTAACTGTTC ACAGTTCTAA TTTGTGTAAC TGTGAAATTG TTCAGGTCAG
7451  TGGAATGCCT ACATTTTGCA TCCCTGTTCC AGATGGTGGT GTTGGTTTTG
7501  ACTACCGCCT GCATATGGCT GTAGCAGATA AATGGATTGA ACTCCTCAAG
7551  TAAGTGCAGG AATATTGGTG ATTACATGCG CACAATGATC TAGATTACAT
7601  TTTCTAAATG GTAAAAAGGA AAATATGTAT GTGAATATCT AGACATTTGC
7651  CTGTTATCAG CTTGAATACG AGAAGTCAAA TACATGATTT AAATAGCAAA
7701  TCTCGGAAAT GTAATGGCTA GTGTCTTTAT GCTGGGCAGT GTACATTGCG
7751  CTGTAGCAGG CCAGTCAACA CAGTTAGCAA TATTTTCAGA AACAATATTA
7801  TTTATATCCG TATATGAnGA AAGTTAGTAT ATAAACTGTG GTCATTAATT
7851  GTGTTCACCT TTTGTCCTGT TTAAGGATGG GCAGTAGGTA ATAAATTTAG
7901  CCAGATAAAA TAAATCGTTA TTAGGTTTAC AAAAGGAATA TACAGGGTCA
7951  TGTAGCATAT CTAGTTGTAA TTAATGAAAA GGCTGACAAA AGGCTCGGTA
8001  AAAAAAACTT TATGATGATC CAGATAGATA TGCAGGAACG CGACTAAAGC
8051  TCAAATACTT ATTGCTACTA CACAGCTGCC AATCTGTCAT GATCTGTGTT
8101  CTGCTTTGTG CTATTTAGAT TTAAATACTA ACTCGATACA TTGGCAATAA
8151  TAAACTTAAC TATTCAACCA ATTTGGTGGA TACCAGAnAT TTCTGCCCTC
8201  TTGTTAGTAA TGATGTGCTC CCTGCTGCTG TTCTCTGCCG TTACAAAAGC
8251  TGTTTTCAGT TTTTTGCATC ATTATTTTTG TGTGTGAGTA GTTTAAGCAT
8301  GTTTTTTGAA GCTGTGAGCT GTTGGTACTT AATACATTCT TGGAAGTGTC
8351  CAAATATGCT GCAGTGTAAT TTAGCATTTC TTTAACACAG GCAAAGTGAC
8401  GAATCTTGGA AAATGGGCGA TATTGTGCAC ACCCTAACAA ATAGAAGGTG
8451  GCTTGAGAAG TGTGTAACTT ATGCAGAAAG TCATGATCAA GCACTAGTTG
8501  GTGACAAGAC TATTCCATTC TGGTTGATGG ATAAGGTACT AGCTGTTACT
8551  TTTGGACAAA AGAATTACTC CCTCCCGTTC CTAAATATAA GTCTTTGTAG
8601  AGATTCCACT ATGGACCACA TAGTATATAG ATGCATTTTA GAGTGTAGAT
8651  TCACTCCATT TGCTTCGTAT GTAGTCCATA GTGAAATCTC TACAGAGACT
8701  TATATTTAGG AACGGAGGGA GTACATAATT GATTTGTCTC ATCAGATTGC
8751  TAGTGTTTTC TTGTGATAAA GATTGGCTGC CTCACCCATC ACCAGCTATT
8801  TCCCAACTGT TACTTGAGCA GAATTTGCTG AAAACGTACC ATGTGGTACT
8851  GTGGCGGCTT GTGAACTTTG ACAGTTATGT TGCAATTTTC TGTTCTTATT
8901  TATTTGATTG CTTATGTTAC CGTTCATTTG CTCATTCCTT TCCGAGACCA
```

Figure 1 continued

```
8951   GCCAAAGTCA CGTGTTAGCT GTGTGATCTG TTATCTGAAT CTTGAGCAAA
9001   TTTTATTAAT AGGCTAAAAT CCAACGAATT ATTTGCTTGA ATTTAAATAT
9051   ACAGACGTAT AGTCACCTGG CTCTTTCTTA GATGATTACC ATAGTGCCTG
9101   AAGGCTAAA  TAGTTTTGGT GTTTCTTGGA TGCCGCCTAA AGGAGTGATT
9151   TTTATTGGAT AGATTCCTGG CCGAGTCTTC GTTACAACAT AACATTTTGG
9201   AGATATGCTT AGTAACAGCT CTGGGAAGTT TGGTCACAAG TCTGCATCTA
9251   CACGCTCCTT GAGGTTTTAT TATGGCGCCA TCTTTGTAAC TAGTGGCACC
9301   TGTAAGGAAA CACATTCAAA AGGAAACGGT CACATCATTC TAATCAGGAC
9351   CACCATACTA AGAGCAAGAT TCTGTTCCAA TTTTATGAGT TTTTGGGACT
9401   CCAAAGGGAA CAAAAGTGTC TCATATTGTG CTTATAACTA CAGTTGTTTT
9451   TATACCAGTG TAGTTTTATT CCAGGACAGT TGATACTTGG TACTGTGCTG
9501   TAAATTATTT ATCCGACATA GAACAGCATG AACATATCAA GCTCTCTTTG
9551   TGCAGGATAT GTATGATTTC ATGGCTCTGG ATAGGCTTCA ACTCTTCGCA
9601   TTGATCGTGG CATAGCATTA CATAAAATGA TCAGGCTTGT CACCATGGGT
9651   TTAGGTGGTG AAGGCTATCT TAACTTCATG GAAATGAGT  TTGGGCATCC
9701   TGGTCAGTCT TTACAACATT ATTGCATTCT GCATGATTGT GATTTACTGT
9751   AATTTGAACC ATGCTTTTCT TTCACATTGT ATGTATTATG TAATCTGTTG
9801   CTTCCAAGGA GGAAGTTAAC TTCTATTTAC TTGGCAGAAT GGATAGATTT
9851   TCCAAGAGGC CCACAAACTC TTCCAACCGG CAAAGTTCTc CCCTGGAAAT
9901   AACAATAGTT ATGATAAATG CCGCCGTAGA TTTGATCTTG TAAGTTTTAG
9951   CTGTGCTATT ACATTCCCTC ACTAGATCTT TATTGGCCAT TTATTTCTTG
10001  ATGAAATCAT AATGTTTGTT AGGAAAGATC AACATTGCTT TTGTAGTTTT
10051  GTAGACGTTA ACATAAGTAT GTGTTGAGAG TTGTTGATCA TTAAAAATAT
10101  CATGATTTTT TGCAGGGAGA TGCAGATTTT CTTAGATATC GTGGTATGCA
10151  AGAGTTCGAT CAGGCAATGC AGCATCTTGA GGAAAAATAT GGGGTATGTC
10201  ACTGGTTTGT CTTTGTTGCA TAACAAGTCA CAGTTTAACG TCAGTCTCTT
10251  CAAGTGGTAA AAAAAGTGTA GAATTAATTC CTGTAATGAG ATGAAAACTG
10301  TGCAAAGGCG GAGCTGGAAT TGCTTTTCAC CAAAACTATT TTCTTAAGTG
10351  CTTGTGTATT GATACATATA CCAGCACTGA CAATGTAACT GCAGTTTATG
10401  ACATCTGAGC ACCAGTATGT TTCACGGAAA CATGAGGAAG ATAAGGTGAT
10451  CATCCTCnAA AAGAGGAGAT TTGGTATTTG TTTTCAACTT CCACTGGAGC
10501  AATAGCTTTT TTGACTACCG TGTTGGGTGT TCCAAGCCTG GAAGTACAA
10551  GGTATGCTTG CCTTTTCATT GTCCACCCTT CACCAGTAGG GTTAGTGGGG
10601  GCTTCTACAA CTTTTAATTC CACATGGATA GAGTTTGTTG GTCGTGCAGC
10651  TATCAATATA AAGAATAGGG TAATTTGTAA AGAAAAGAAT TTGCTCGAGC
10701  TGTTGTAGCC ATAGGAAGGT TGTTCTTAAC AGCCCGAAG  CACATACCAT
10751  TCATTCATAT tATCTACTTA AGTGTTTGTT TCAATCTTTA TGCTCAGTTG
10801  GACTCGGTCT AATACTAGAA CTATTTTCCG AATCTACCCT AACCATCCTA
10851  GCAGTTTTAG AGCAGCCCCA TTTGACAAT  TGGCTGGGTT TTTGTTAGTT
10901  GTGACAGTTT CTGCTATTTC TTAATCAGGT GGCCTTGGAC TCTGACGATG
10951  CACTCTTTGG TGGATTCAGC AGGCTTGATC ATGATGTCGA CTACTTCACA
11001  ACCGTAAGTC TGGGCTCAAG CGTCACTTGA CTCGTCTTGA CTCAACTGCT
11051  TACAAATCTG AATCAACTTC CCAATTGCTG ATGCCCTTGC AGGAACATCC
11101  GCATGACAAC AGGCCGCGCT CTTTCTCGGT GTACACTCCG AGCAGAACTG
11151  CGGTCGTGTA TGCCCTTACA GAGTAAGAAC CAGCAGCGGC TTGTTACAAG
11201  GCAAAGAGAG AACTCCAGAG AGCTCGTGGA TCGTGAGCGA AGCGACGGGC
11251  AACGGCGCGA GGCTGCTCCA AGCGCCATGA CTGGAGGGG  ATCGTGCCTC
11301  TTCCCCAGAT GCCAGGAGGA GCAGATGGAT AGGTAGCTTG TTGGTGAGCG
11351  CTCGAAAGAA AATGGACGGG CCTGGGTGTT TGTTGTGCTG CACTGAACCC
11401  TCCTCCTATC TTGCACATTC CCGGTTGTTT TTGTACATAT AACTAATAAT
11451  TGCCCGTGCG CTCAACGTGA AAATCC
```

Figure 2. Partial wheat SBEIIb gene sequence (wbe2b genomic)

```
   1 AAGCTTTGTA GCCTTGCACG GGCTCCCCAA CAAACTGCCT CACTCGATTG
  51 TCAAAAAAGT AAAAATGATT GTAGAAAAAA AAACTGACTC ACTCGTCACT
 101 ACCCTACCGT CCTACATGAC ACCTGGCCGC AAGACGACGC CGTCCTCCTG
 151 CCGCGCGCGT CCGCGATCAC ACCACCGCAA AAACCAAAAC CTCTTCGCCG
 201 GTGCGTCCCA CGCTACCATC CATGCAGCCG TCCGCCCGCG CGCGCGTTGC
 251 CCGCACCACC CGCTGGCGGC CACCACGCCG CCACTCTCGC GTGAAGGCTC
 301 CGTCCGCTTC CTCCTAGTTC CACTCTCTCT CCGTGCTAGC AGTATATAGC
 351 ATCCGCCCTC CGCCCCCTCC CAATCTTAGA ACACCCCTCC CTTTGCCTCC
 401 TCATTTCGCT CGCGTGGGTT TAAGCAGGAG ACGAGGCGGG GTCAGTTGGG
 451 CAGTTAGGTT GGATCCGATC CGGCTGCGGC GGCGGCGACG GGATGGCTGC
 501 GCCGGCATTC GCAGTTTCCG CGGCGGGGCT GGCCCGGCCG TCGGCTCCTC
 551 GATCCGGCGG GGCAGAGCGG AGGGGCGCG GGGTGGAGCT GCAGTCGCCA
 601 TCGCTGCTCT TCGGCCGCAA CAAGGGCACC CGTTCACCCC GTAATTATTT
 651 GCGCCACCTT TCTCACTCAC ATTCTCTCGT GTATTCTGTC GTGCTCGCCC
 701 TTCGCCGACG ACGCGTGCCG ATTCCGTATC GGGCTGCGGT GTTCAGCGAT
 751 CTTACGTCGG TTCCCTCCTG GTGTGGTGAT GTCTGTAGGT GCCGTCGGCG
 801 TCGGAGGTTC TGGATGGCGC GTGGTCATGC GCGCGGGGGG GCCGTCCGGG
 851 GAGGTGATGA TCCCTGACGG CGGTAGTGGC GGAACACCGC CTTCCATCGA
 901 CGGTCCCGTT CAGTTCGATT CTGATGATCT GAAGGTAGTT TTTTTTTGC
 951 ATCGATCTGA AGGTACTTGA CATATACTAC TGTATTACCC TGAGTAAATA
1001 CTGCCACCAT ATTTTTATGG TTCGCTTGAA ATACCTGTTT ACTTGCTACG
1051 GTTTTCACTT TCATTGAGAC GTCGGACGAA ATTCACTGAA TTCCTATAAT
1101 TTGGTAGACA CCGAAATATA TACTACTCCT TCCGTCCCAT AATATAAGAG
1151 CGTTTTTGGC ACCTTATATT ATAGGGCGGA GGGAGTACCT TTTAGGTCAA
1201 AATATTGTGG TAGTTTCAAT TGTATACAAG AATTCAAATA TTTTTTTTAA
1251 AAAAAAATCA ACTAATTGGT TGAGTTTCAA GTGAAGCGTT TTGGTCCTTT
1301 GGCTGAGATG TAAACCGAAA TCACTGAAAT TCATAGTAGC CGAAACTTTA
1351 ATAGAACTGA AACTCAAAAT CTGCTATCCG GCGAAATTCT AAAGATTTGC
1401 TTATTTCACA CGTAGGTTGC AGTACACCCT CTTTCTAATT TATTGGGGAA
1451 GGGGTATTAT TATCTTGTTA GTACCTGCCT GCATGACAAT TGAAATCTAA
1501 GACAAAACAC CATATGCGAG GCCTACACAC GGTAGGTTGG TTTACAACTA
1551 TGTGTGCCAC AGTTCGTCTG AACTTTTGT CCTTCACATC GTGTTAGGTT
1601 CCATTCATTG ATGATGAAAC AAGCCTACAG GATGGAGGTG AAGATAGTAT
1651 TTGGTCTTCA GAGACAAATC AGGTTAGTGA AGAAATTGAT GCTGAAGACA
1701 CGAGCAGAAT GGACAAAGAA TCATCTACGA GGGAGAAATT ACGCATTCTG
1751 CCACCACCGG GAAATGGACA GCAAATATAC GAGATTGACC CAACGCTCCG
1801 AGACTTTAAG TACCATCTTG AGTATCGGTA TGCTTCGCTT CTATTGTGTG
1851 CACTTTAAAA ACAATTTACA GTCTTTGATA AGATGTGAAT GGCTGCTTGC
1901 TGTGACACGA AACTCTTGAA GTTCGTAGTC ACTCTTGTGT GTTCATGGTT
1951 CTGAGGTAAC ATGGTAACCG AACAAAAATA GGAAAGTGGC AAGCACTGCA
2001 ATGTGAGCTA CTGATAACCA CCCATTGTAA TTGGGTACAC TGATTAATAT
2051 ATATGTCTTC ATGGGCTCTA TTTTTTTTCA ATATCTATGC CAATTGAACA
2101 ACAATGCTTT GTGGACGGGT GTTCTTTTAC CCTCTTCTTC TATCAATAGA
2151 TGATATGCAT ACTCATGCGT ATCCTACAAA AAATTGAACA ACAATGCCAC
2201 TTTCCCCCGT GTTGCTTTTG TAAGGATGAA ACACATATGT CCAGATCAAA
2251 CTATACTAGC AGTCTAACTG TGCCTTAATG GATCAAAAAC AGATATAGCC
2301 TATACAGGAG AATACGTTCA GACATTGATG AACACGAAGG AGGCATGGAT
2351 GTATTTCCC GCGGTTACGA GAAGTTTGGA TTTATGCGCA GGTGAAATTT
2401 CTTGACTAAA TAACTATGTA TCTACCTTTT CTTTGTACTC TATCAACATT
2451 CCTCTTCCCA TGCAGCGCTG AAGGTATCAC TTACCGAGAA TGGGCTCCTG
2501 GAGCAGATGT ACGTTCTTCT AACCATCTGA TCGTTTACCT GACTATACTA
2551 ATTCTATCTT TCAACTAATT GTGAATAATT ACTGCTCATC AGCTATCCTA
2601 AGGTTGGGGA TTTTGCACCT CCCAGATGAA CAGCATATTA AGTCGCACAA
2651 CTAGCATTAT TAAGAACTAA CTCCTGCTTC CAATTGCAGT CTGCAGCATT
2701 AGTTGGCGAC TTCAACAATT GGGATCCAAA TGCAGACCAT ATGAGCAAAG
2751 TATGCATGTA GTTCACAAA TATATCATAT TTTCTTTGTA GATTTTTTT
2801 TTTAGATCGG CTTATCTATT TAATGTGGT TGAATATACA CCTTATATGT
2851 ACGTTGAGCT GTAAATATAG TTGGAAGTGT TTAGGAGTAT TAAATTCACT
2901 GGACTCTATT CTTTCACTTG CCTGTTGCAC GAGCCCATTA CTAGATATCA
```

Figure 2 continued

```
2951 ATGTTGATGA TGCTTTTGTT GTATGAGGTC GAAGTGAAAC ATGCATGTTA
3001 CCCTTTTATA TAAGTAAGGT TGCACATGTA TTTTTTATGA TCTAAACATT
3051 ATTTACTGAT TTTGTTCTTG CAAGACACTA AGCAGTTTTA CATAATAATG
3101 GCGTTGGAGC AGGCCGACTG CACATCTGAA CTGTAGCTCC ATGTGGTTGA
3151 TATAGATTAC AAATGCTCAT ATTCAATGTA ACTGTTTTCA GAATGACCTT
3201 GGTGTTTGGG AGATTTTTCT GCCAAACAAT GCAGATGGTT CGCCACCAAT
3251 TCCTCACGGC TCACGGGTGA AGGTTGTTTT CTTCTCCTTG CCAACGGTGT
3301 TAGGCTCAGG AACATGTCCT GTATTACTCA GAAGCTCTTT TGAACATCTA
3351 GGTGAGAATG GATACTCCAT CTGGGATAAA GGATTCAATT CCTGCTTGGA
3401 TCAAGTACTC CGTGCAGACT CCAGGAGATA TACCATACAA TGGAATATAT
3451 TATGATCCTC CCGAAGAGGT ATTTTACTTC ATCTTCTGTG CTTTTAGATT
3501 TCAGATATTT TTATTAGAAG AAAATTATGA TTTTTTCCCT CACGAACCTT
3551 CCCAATTGCT ATTTCAAGCT GTCCTACTTA TTTGCTGCTG GCATCTTATT
3601 TTTCTATTCT CTAACCAGTT ATGAAATTCC TTACATGCAT ATGCAGGAGA
3651 AGTATGTATT CAAGCATCCT CAACCTAAAC GACCAAAATC ATTGCGGATA
3701 TATGAAACAC ATGTTGGCAT GAGTAGCCCG GTATTTCATC TTTACCATGT
3751 ATTCCATAAA TGAAGTTAGC TATATGCAGT TCAAATTTAT TTACAGGTTG
3801 TTACAATGGT ATTTTGTGT TGGTGCCCTT CTTTCGTTTT ATAAGTAAAA
3851 AACTTATCAT AAATTTATTT GTTATGCCGC TTGGTTAATA CAATCTGAAA
3901 AATGTAACTG TGGACAATCT AGAACTAGAT AATACAAATC TGAAAAAACA
3951 TGCTGGAATA GTGTCATTTC AGTCAACTAG GATGTTTTGA ATGCTCAAGA
4001 GAAGTACTAG TGTGTAGCAT CAAAAGCTGG TGTCCATTTG TTCAAATGTT
4051 TAATTAACAC TATAGTGAAA CAAGTAATT GCACAAAGAA ACAAGTAATT
4101 GCCCAAGTTC ATATGTTTT TCACTATATT ACATGTTTCA TCAACAATTT
4151 AATTAACCTC ATTCCTTACA AACATTTGTA TTTACATTTG TTCCTACATA
4201 TATAGTTATT TTATATATCA ACTTTATAAA TCATGACTGT TATAATTAAA
4251 ACCGATGGTA TATCAACGAT TGAGATAATT TGGCATATGT GGATGAATTT
4301 TGTGGCTTGT TATGCTCTTG TTTTAATAAC ATAATAAATA GATTATGCTT
4351 GTTGGTAGCC TTTTTACATT AACACATGGG CAATTACTTG TTTCTTTGTG
4401 CAACCAGGAA CCAAAGATCG ACACATATGC AAACTTCAGG GATGAGGTGC
4451 TTCCAAGAAT TAAAAGACTT GGATACAATG CAGTGCAAAT AATGGCAATC
4501 CAAGAGCACT CATACTATGG AAGCTTTGGG TAGTTCTCTG GGTCGATTTC
4551 TGGTTCTTTT AGTTATCTTT TGTCCATAGA ACATATTTCA ACTTTAGCAA
4601 CTATACTATT ATATTAACTT TTCAGCTATT GTCTTNCTTT TTCTTATGTG
4651 AGAGACTGCT GCNTCTTGCT ACTTCCTGTG TTCTCATTCA GAGTANACAT
4701 CTTATGANTA GACAACTCTA TGTNGACATT CCGGAAGTAT NCACTGGCTG
4751 ATTCGGTCTA AAATAACATA CTGCTCAGAT AGCCACATAA CAGTACGATT
4801 ACACACATAA TGACCATGTT TGCATAGAGT GGCGGTAGTA TGTTCCTCAC
4851 CATACTAGCA TAATGACTTG TTATATAAGA GTATATCATA TTAACTTCTT
4901 TTCCAATGAC ATGGAAGCTG TAACAACTTT CAAATCATTT TTGTCTTTTA
4951 AGTGCTGCTT TTTTCCTGTT TGACAATTAA TACAATACCA CTTTTATGTG
5001 TTTTTACTTC TATTGCAGGT ACCATGTTAC CAATTTCTTT GCACCAAGTA
5051 GCCGTTTTGG GTCCCCAGAA GATTTAAAAT CTTTGATTGA TAGAGCTCAC
5101 GAGCTTGGCT TGGTTGTCCT CATGGATGTT GTTCACAGGT ACTTAATGTA
5151 ATTTGAGGTT GGCGTGTTAA GTTCACATTA ATCTTAATTC TTTATTTCAA
5201 TTCCTATGGC CTCTCTCCTA GATTGGAACA GTAAAAGCAT CATCCAGTTT
5251 GTATAAATTG CTAAAAGAAC ATTTTACATG TTAAGTATTT TCAATTACTA
5301 TGAAACATAT AAATTTACAT ACTTATTGAT TTTACGACAG AAGTACCGAT
5351 CTCACAAGAT GAACAATTGG TTGATCACAT ATCATTTCAT ACTACAATAC
5401 AAGAAAATGA ATAGAGAACG AGTTAATATT AGCCTTGGTA AAATCAGCAA
5451 CTTGTTTGGA AATAAAGTAT AGTGATGCCA GTGCAAANAA CAAGGCATCA
5501 AGTTGGTTTC AGCTCCCACG GTCGGTGCTA GCTGTCAAGG GTAAATTTGCA
5551 CGTAGTCGCA CATAGATTTG TGTGGGAGTG GAAAGTAACC ACAGATTGTC
5601 CGAGGAACAC GGGACACACG TCTTAGCCAC AGGTTTGGGC TCCCCTTGAT
5651 GCGGGTAGTA GCTTTACTCC TTATATGAAA TTATCTCAAG ATAGATTTCA
5701 ATTTGGGGTT ACACTTANGA ACTCANCAAG TTAAGGATCA ACTCNCTGAG
5751 TTCTATACGA CTGATCTTTG ACCGAGATAT CTTGATCAGG CTAAGTANCA
5801 AAATCCAGGC CTTGAGATGT TGAACATGTC CTTCATTTTG GGCTGGGTGC
5851 CCTTGGGCAT AAGGTGTNGT CCTTCCTTCA TGTGCTTCTT GCAGCGTATG
5901 ACATAAACNT CCTCTGAGTT GGTANATGCA CGGTTCCCTT TGAGGAAATC
5951 AGGGGTAGTC GCATCTNGGG AAAGTTGGTC ACCCANGCAT GGATCCTCNG
```

Figure 2 continued

```
6001  CGCACACCGG GCAAACACGG TGAAACCACT TCTCCTCGAC ACTAGCTAAC
6051  TTGACATTCA AGCAAACTAA GAATATAACT TTATNTCTAA ATGAACCGGA
6101  CACCCTCCTT GTGCCTGCAC CTACAGAGTA CAATGCCAGT TTTGGACTGA
6151  ACTCTTGTGT TCATGTATGT GCTAATNACA TAGGTTCTAA CCATGATTCT
6201  AAATAGCGCG TTATAACTCC ACTATAGTAA TGCTATAGCG TTTANAAGAT
6251  CCCGCACTAA GGGACCTTAG TCCAAATACA TGATCAAACA TTTTACATAG
6301  CGCGCTATAG CTATTTAAAA CTATGGTCAC CCGCTAAGAG GCATAACTCG
6351  CTATTTAAAA CTATGGTTCT AACTTTTAAT CTATTTTATG TCTTGGTCCA
6401  AAGCCCCTTT TTGTTCTATA GCTTTACCTT TGGGTTGAGA TCACCCTTAA
6451  CCCATTGGTA ATCCTGGTTG ATTTACTCCA TCCTTTCTTG CGTAGCTTTA
6501  CTTTTGGTTT TTTGTTTCTC ACAGTCACGC GTCAAATAAT ACCTTGGACG
```

Figure 3. Schematic of duplex-RNA constructs. A. The order of the gene elements used were promoter, SBEIIa or SBEIIb gene sequence (exons 1, 2 and 3) in sense orientation, intron (intron 3), SBEIIa or SBEIIb gene sequence (exons 1, 2, 3 and 4) in antisense orientation, and transcription terminator/polyadenylation sequence. B. The transcript of the ds-SBEIIa and ds-SBEIIb genes forms a "hairpin" RNA structure with a double-stranded region formed by hybridization between the sense and antisense sequences. The intron sequence bordered by the GT and AG nucleotides is spliced out.

A

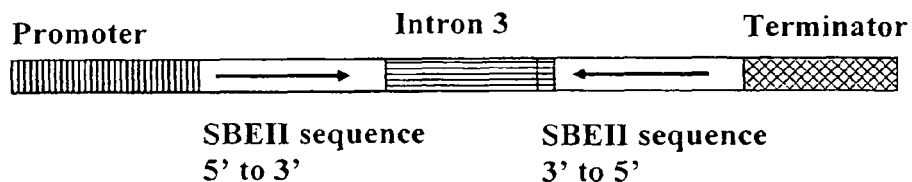

B

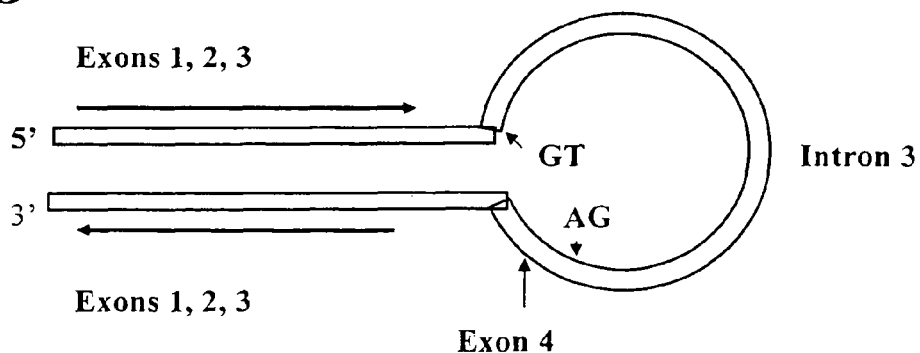

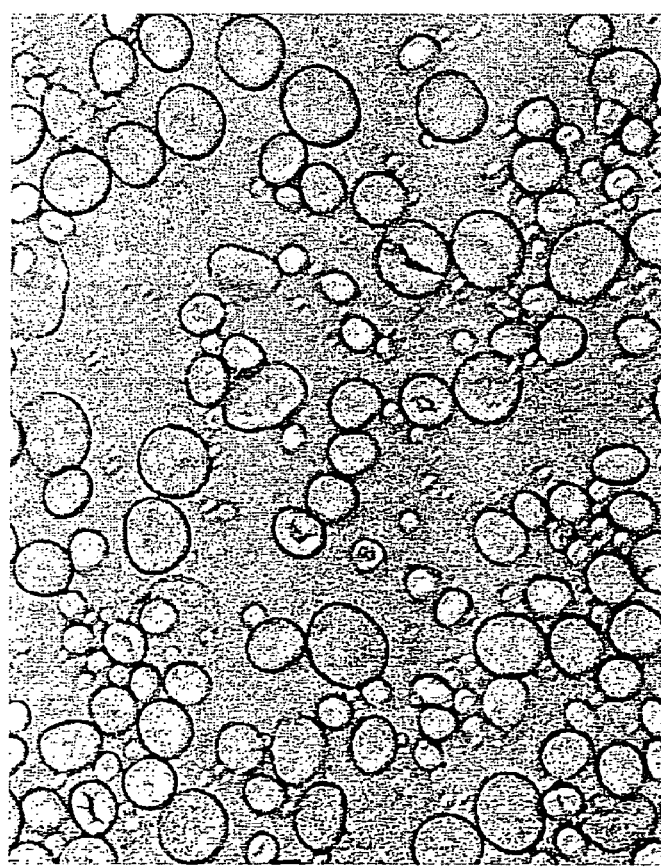
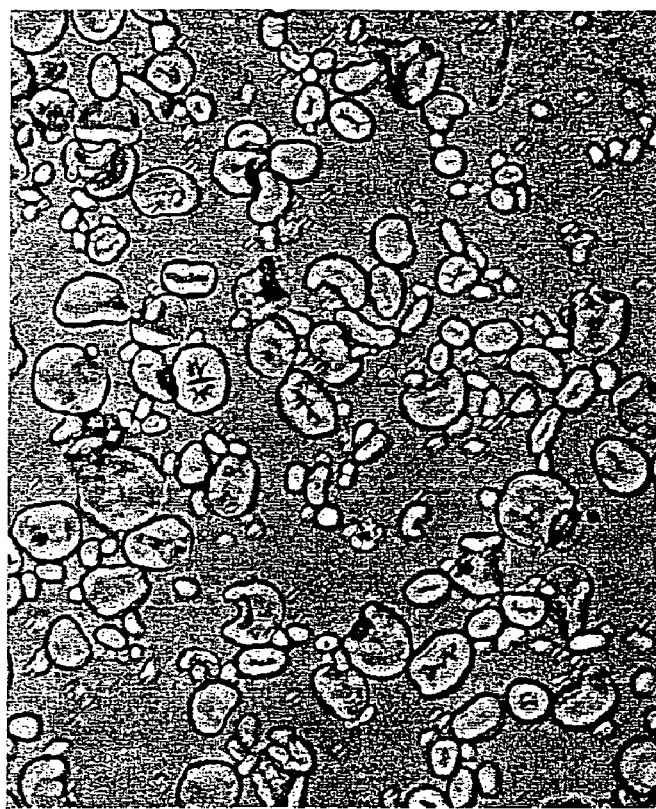
Figure 4

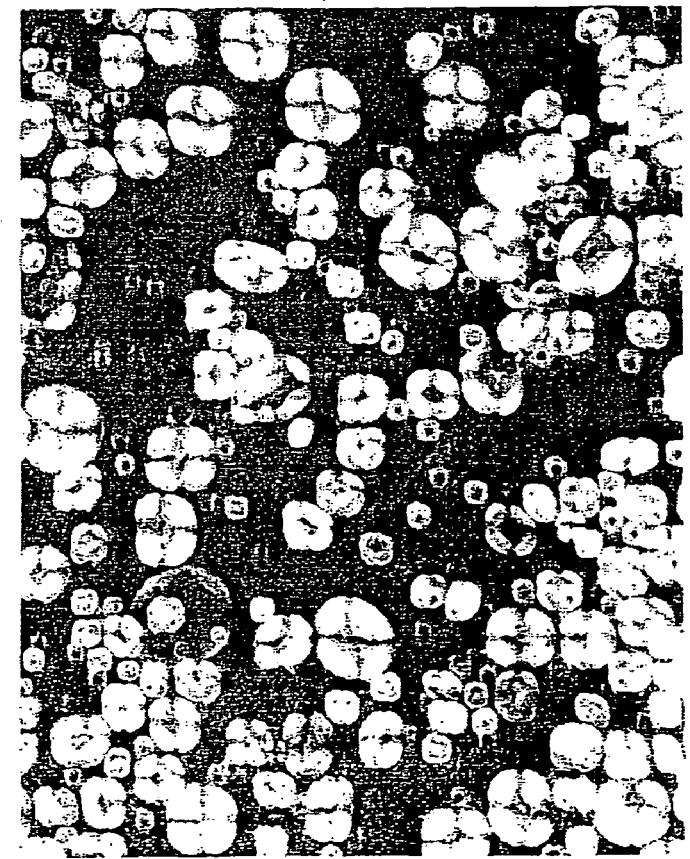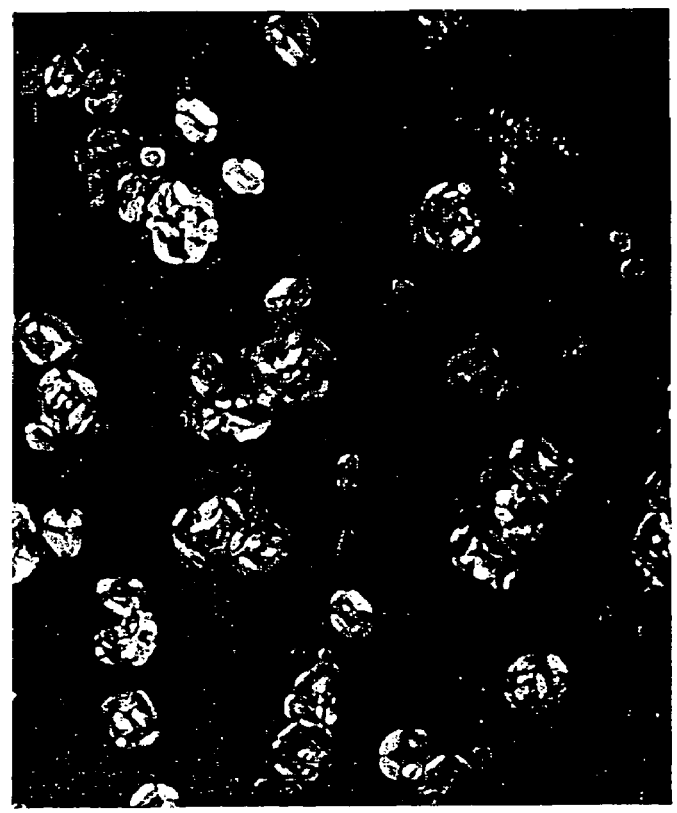
Figure 5

Figure 6. Comparison of SBEIIa cDNA sequences.

```
Y11282  CGCCAGCTTC CACCCCCGCC GCACACGTTG CTCCCCCTTC TCATCGCTTC
sr997   ~~~~~~~~~~ ~~~~~~~~~~ ~~~~~~~~~~ ~~~~~~~~~~ ~~~~~~~~~~
sr995   ~~~~~~~~~~ ~~~~~~~~~~ ~~~~~~~~~~ ~~~~~~~~~~ ~~~~~~~~~~
sbe9    ---------- ---------- --------AC GTTG CTCCCCCTTC TCATCGCTTC 51                                                   100
Y11282  TCAATTAATA TCTCCATCAC TCGGGTTCCG CGCTGCATTT CGGCCGGCGG
sr997   ~~~~~~~~~~ ~~~~~~~~~~ ~~~~~~~~~~ ~~~~~~~~~~ ~~~~~~~~~~
sr995   ~~~~~~~~~~ ~~~~~~~~~~ ~~~~~~~~~~ ~~~~~~~~~~ ~~~~~GGCGG
sbe9    TCAATTAATA TCTCCATCAC TC-GGTTCCG CGCTGCATTT CGGCCGGCGG 101                                                  150
Y11282  GTTGAGTGAG ATCTGGGCCA CTGACCGACT CACTCGCTCG CTGCGCGGGG
sr997   ~~~~~~~~~~ ~~~~~~GCCA CTGACCGACT CACTCGCTCG CTGCGCGGGG
sr995   GTTGAGTGAG ATCTGGGCGA CTGGCTGACT CA....ATCA CTACGCGGGG
sbe9    GTTGAGTGAG ATCTGGGCCA CTGACCGACT CACTCGCTCG CT--GCGGGG 151                                                  200
Y11282  ATGGCGACGT TCGCGGTGTC CGGCGCGACC CTCGGTGTGG CGCGGCCCGC
sr997   ATGGCGACGT TTGCGGTGTC CGGCGCGACC CTCGGTGTGG CGCGGCCCGC
sr995   ATGGCGACGT TCGCGGTGTC CGGCGCGACT CTCGGTGTGG CGCGGGCCGG
sbe9    ATGGCGACGT TCGCGGTGTC CGGCGCGACC CTCGGTGTGG CGCGG-CCGC 201                                                  250
Y11282  CGGCGCCGGC GGCGGACTGC TGCCGCGATC CGGCTCGGAG CGGAGGGGCG
sr997   CGGCGCCGGC GGCGGACTGC TGCCGCGATC CGGCTCGGAG CGGAGGGGCG
sr995   CGTCGGAG.. .......... TGGCGCGGGC CGGCTCGGAG CGGAGGGGCG
sbe9    CGGCGG.... .......... .......... .......... ..........

251                                                  300
Y11282  GGGTGGACCT GCCGTCGCTG CTCCTCAGGA AGAAGGACTC CTCTCGCGCC
sr997   GGGTGGACCT GCCGTCGCTG CTCCTCAGGA AGAAGGACTC CTCTCGCGCC
sr995   GGGCGGACTT GCCGTCGCTG CTCCTCAGGA AGAAGGACTC CTCTCGCGCC
sbe9    .......... .......... .......... .......... ..........

301                                                  350
Y11282  GTCCTGAGCC GCGCGGCCTC TCCAGGGAAG GTCCTGGTGC CTGACGGTGA
sr997   GTCCTGAGCC GCGCGGCCTC TCCAGGGAAG GTCCTGGTGC CTGACGGTGA
sr995   GTCCTGAGCC GCGCGGCCTC TCCAGGGAAG GTCCTGGTGC CTGACGGCGA
sbe9    .......... .......... .......... .......... ..........

351                                                  400
Y11282  GAGCGACGAC TTGGCAAGTC CGGCGCAACC TGAAGAATTA CAGATACCTG
sr997   GAGCGACGAC TTGGCAAGTC CGGCGCAACC TGAAGAATTA CAGAT~~~~~
sr995   GAGCGACGAC TT.GCAAGTC CGGCGCAACC TGAAG~~~~
sbe9    .......... .......CGG CGCAACC TGAAGAATTA CAGATACCTG
```

Figure 8. Comparison of the deduced amino acid sequences of the D-subgenome polypeptide (sr854) with the product from the A or B subgenome (y11282). The transit sequence (positions 1-54) is italicized.

```
sr854    MATFAVSGATLGVAR-AGVG---VARAGSERRGGADLPSLLLRKKDSSRAVLSRAASPGK
         ||||||||||||||| ||:|    :|:||||||||:||||||||||||||||||||||||
y11282   MATFAVSGATLGVARPAGAGGGLLPRSGSERRGGVDLPSLLLRKKDSSRAVLSRAASPGK
                 10        20        30        40        50        60

60        70        80        90       100       110
sr854    VLVPDGESDDLASPAQPEELQIPEDIEEQTAEVNMTGGTAEKLQSSEPTQGIVETITDGV
         ||||||||||||||||||||||||||||||||||||||||||:|||||||||||||||||
y11282   VLVPDGESDDLASPAQPEELQIPEDIEEQTAEVNMTGGTAEKLESSEPTQGIVETITDGV
                 70        80        90       100       110       120

120       130       140       150       160       170
sr854    TKGVKELVVGEKPRVVPKPGDGQKIYEIDPTLKDFRSHLDYRYSEYKRIRAAIDQHEGGL
         |||||||||||||||||||||||||||||||||||||||||||||:||||||||||||||
y11282   TKGVKELVVGEKPRVVPKPGDGQKIYEIDPTLKDFRSHLDYRYSEYRRIRAAIDQHEGGL
                130       140       150       160       170       180

180       190       200       210       220       230
sr854    EAFSRGYEKLGFTRSAEGITYREWAPGAHSAALVGDFNNWNPNADTMTRDDYGVWEIFLP
         ||||||||||||||||||||||||||||||||||||||||||||||||||||||||||||
y11282   EAFSRGYEKLGFTRSAEGITYREWAPGAHSAALVGDFNNWNPNADTMTRDDYGVWEIFLP
                190       200       210       220       230       240

240       250       260       270       280       290
sr854    NNADGSSAIPHGSRVKIRMDTPSGVKDSISAWIKFSVQAPGEIPFNGIYYDPPEE-KYVF
         ||||||  |||||||||||||||||||||||||||||||||||||||||||||||| ||||
y11282   NNADGSPAIPHGSRVKIRMDTPSGVKDSISAWIKFSVQAPGEIPFNGIYYDPPEEEKYVF
                250       260       270       280       290       300

300       310       320       330       340       350
sr854    QHPQRKRPESLRIYESHIGMSSPEPKINSYANFRDEVLPRIKRLGYNAVQIMAIQEHSYY
         ||||  ||||||||||||||||||||||||||||||||||||||||||||||||||||||
y11282   QHPQPKRPESLRIYESHIGMSSPEPKINSYANFRDEVLPRIKRLGYNAVQIMAIQEHSYY
                310       320       330       340       350       360

360       370       380       390       400       410
sr854    ASFGYHVTNFFAPSSRFGTPEDLKSLIDRAHELGLLVLMDIVHSHSSNNTLDGLNGFDGT
         ||||||||||||||||||||||||||||||||||||||||||||||||||||||||||||
y11282   ASFGYHVTNFFAPSSRFGTPEDLKSLIDRAHELGLLVLMDIVHSHSSNNTLDGLNGFDGT
                370       380       390       400       410       420

420       430       440       450       460       470
sr854    DTHYFHGGPRGHHWMWDSRLFNYGSWEVLRFLLSNARWWLEEYKFDGFRFDGVTSMMYTH
         ||||||||||||||||||||||||||||||||||||||||||||||||||||||||||||
y11282   DTHYFHGGPRGHHWMWDSRLFNYGSWEVLRFLLSNARWWLEEYKFDGFRFDGVTSMMYTH
                430       440       450       460       470       480

480       490       500       510       520       530
sr854    HGLQMTFTGNYGEYFGFATDVDAVVYLMLVNDLIHGLYPDAVSIGEDVSGMPTFCIPVPD
         |||||||||||||||||||||||||||||||||||||:||||||||||||||||||||||
y11282   HGLQMTFTGNYGEYFGFATDVDAVVYLMLVNDLIHGLHPDAVSIGEDVSGMPTFCIPVPD
                490       500       510       520       530       540

```
sr854   GGVGFDYRLHMAVADKWIELLKQSDESWKMGDIVHTLTNRRWLEKCVTYAESHDQALVGD
        ||||:|||||||||||||||||||||||||||||||||||||||||||||||||||||||
y11282  GGVGLDYRLHMAVADKWIELLKQSDESWKMGDIVHTLTNRRWLEKCVTYAESHDQALVGD
                 550       560       570       580       590       600

600       610       620       630       640       650
sr854   KTIAFWLMDKDMYDFMALDRPSTLRIDRGIALHKMIRLVTMGLGGEGYLNFMGNEFGHPE
        ||||||||||||||||||||||||| ||||||||||||||||||||||||||||||||||
y11282  KTIAFWLMDKDMYDFMALDRPSTPRIDRGIALHKMIRLVTMGLGGEGYLNFMGNEFGHPE
                 610       620       630       640       650       660

660       670       680       690       700       710
sr854   WIDFPRGPQTLPTGKVLPGNNNSYDKCRRRFDLVNADFLRYRGMQEFDQAMQHLEEKYGF
        |||||||||||||||||||||||||||||||||:||||||:|||||||||||||||||||
y11282  WIDFPRGPQTLPTGKVLPGNNNSYDKCRRRFDLGDADFLRYHGMQEFDQAMQHLEEKYGF
                 670       680       690       700       710       720

720       730       740       750       760       770
sr854   MTSEHQYVSRKHEEDKVIILKRGDLVFVFNFHWSNSFFDYRVGCSKPGKYKVALDSDDAL
        |||||||||||||||||:|||||||||||||||||||||||||:|||||||||||||||
y11282  MTSEHQYVSRKHEEDKVIIFERGDLVFVFNFHWSNSFFDYRVGCSRPGKYKVALDSDDAL
                 730       740       750       760       770       780

780       790       800       810
sr854   FGGFSRLDHDVDYFTTEHPHDNRPRSFSVYTPSRTAVVYALTE
        ||||||||||||||||||||||||||||||||||||||||||||
y11282  FGGFSRLDHDVDYFTTEHPHDNRPRSFSVYTPSRTAVVYALTE
                 790       800       810       820
```

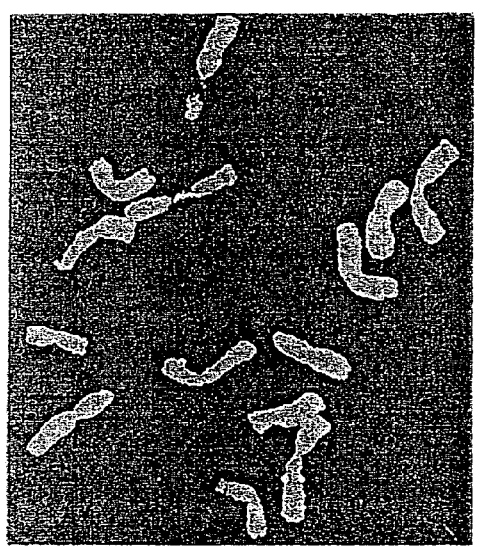
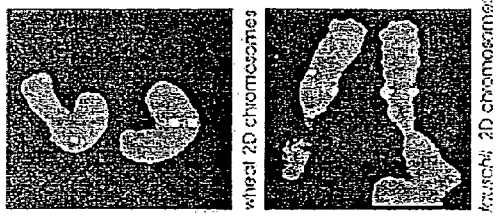
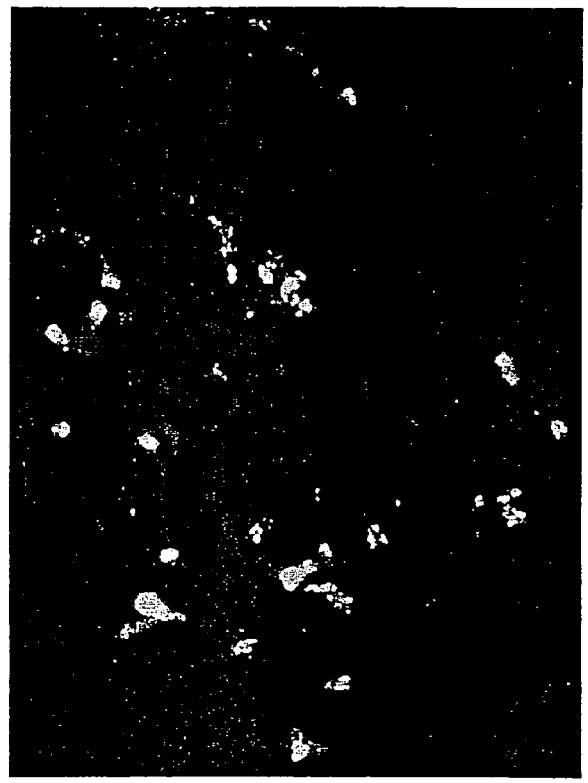
Figure 13

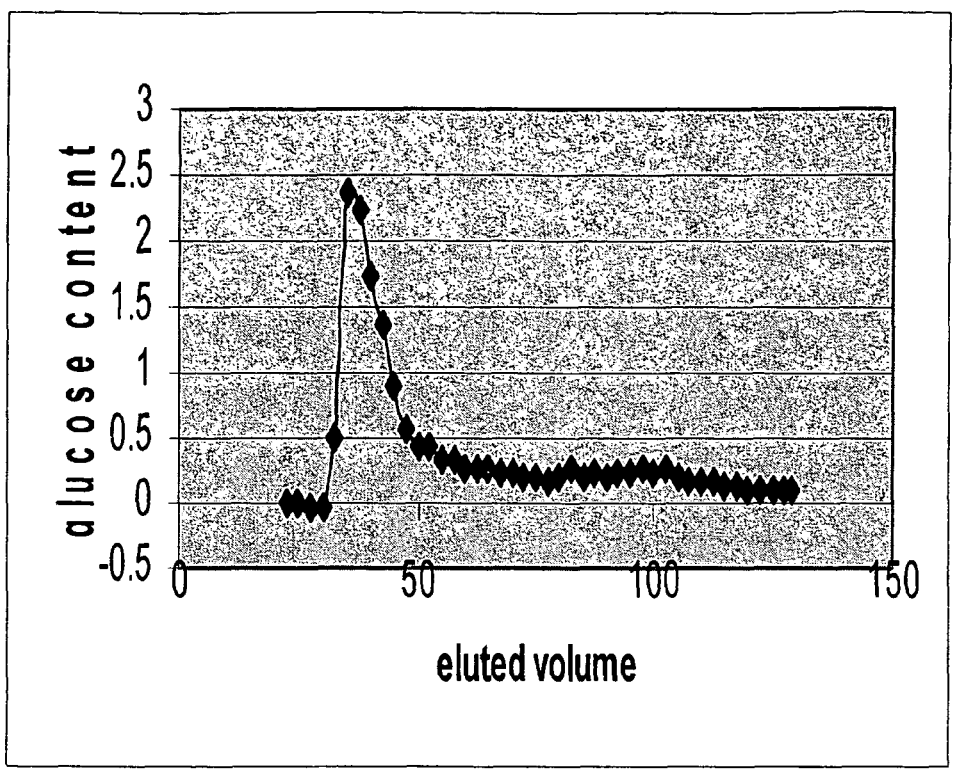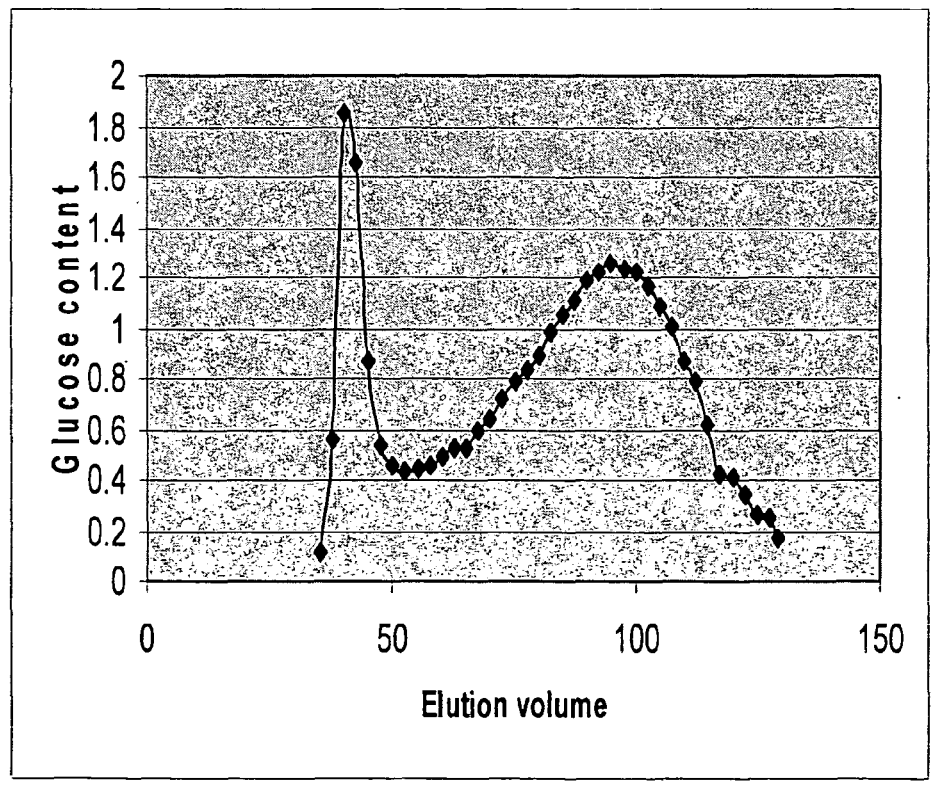
Figure 20

WHEAT WITH ALTERED BRANCHING ENZYME ACTIVITY AND STARCH AND STARCH CONTAINING PRODUCTS DERIVED THEREFROM

This application claims the benefit of U.S. Provisional Application No. 60/484,360, filed Jul. 1, 2003, and U.S. Provisional Application No. 60/484,169, filed Jun. 30, 2003, and the contents of which are hereby incorporated by reference into this application.

FIELD OF THE INVENTION

This invention relates to a wheat plant having kernel starch with a high relative amylose content. The invention also relates to wheat with a reduced starch branching enzyme IIa (SBEIIa) activity in the endosperm and methods of obtaining such plants. The invention also relates to grain and starch and food and non-food products obtained therefrom.

BACKGROUND OF THE INVENTION

In cereals, starch makes up approximately 45-65% of the weight of the mature grain. The starch is composed of two types of molecule, amylose and amylopectin. Amylose is an essentially linear molecule composed of α-1,4 linked glucosidic chains, while amylopectin is highly branched with α-1,6 glucosidic bonds linking linear chains.

The synthesis of starch in the endosperm of higher plants is carried out by a suite of enzymes that catalyse four key steps. Firstly, ADP-glucose pyrophosphorylase activates the monomer precursor of starch through the synthesis of ADP-glucose from G-1-P and ATP. Secondly, the activated glucosyl donor, ADP-glucose, is transferred to the non-reducing end of a pre-existing α1-4 linkage by starch synthases. Thirdly, starch branching enzymes introduce branch points through the cleavage of a region of α-1,4 linked glucan followed by transfer of the cleaved chain to an acceptor chain, forming a new α-1,6 linkage. Starch branching enzymes are the only enzymes that can introduce the α-1,6 linkages into α-polyglucans and therefore play an essential role in the formation of amylopectin. Finally, starch debranching enzymes remove some of the branch linkages although the mechanism through which they act is unresolved (Myers et al., 2000).

While it is clear that at least these four activities are required for normal starch granule synthesis in higher plants, multiple isoforms of each of the four activities are found in the endosperm of higher plants and specific roles have been proposed for individual isoforms on the basis of mutational analysis (Wang et al, 1998, Buleon et al., 1998) or through the modification of gene expression levels using transgenic approaches (Abel et al., 1996, Jobling et al., 1999, Scwall et al., 2000). However, the precise contributions of each isoform of each activity to starch biosynthesis are still not known, and it is not known whether these contributions differ markedly between species. In the cereal endosperm, two isoforms of ADP-glucose pyrophosphorylase are present, one form within the amyloplast, and one form in the cytoplasm (Denyer et al., 1996, Thorbjornsen et al., 1996). Each form is composed of two subunit types. The shrunken (sh2) and brittle (bt2) mutants in maize represent lesions in large and small subunits respectively (Giroux and Hannah, 1994). Four classes of starch synthase are found in the cereal endosperm, an isoform exclusively localised within the starch granule, granule-bound starch synthase (GBSS), two forms that are partitioned between the granule and the soluble fraction (SSI, Li et al., 1999a, SSII, Li et al., 1999b) and a fourth form that is entirely located in the soluble fraction, SSIII (Cao et al, 2000, Li et al., 1999b, Li et al, 2000). GBSS has been shown to be essential for amylose synthesis (Shure et al., 1983), and mutations in SSII and SSIII have been shown to alter amylopectin structure (Gao et al, 1998, Craig et al., 1998). No mutations defining a role for SSI activity have been described.

Three forms of branching enzyme are expressed in the cereal endosperm, branching enzyme I (SBEI), branching enzyme IIa (SBEIIa) and branching enzyme IIb (SBEIIb) (Hedman and Boyer, 1982, Boyer and Preiss, 1978, Mizuno et al., 1992, Sun et al., 1997). Genomic and cDNA sequences have been characterized for rice (Nakamura and Yamanouchi, 1992), maize (Baba et al., 1991; Fisher et al., 1993; Gao et al., 1997) and wheat (Repellin et al., 1997; Nair et al., 1997; Rahman et al., 1997). Sequence alignment reveals a high degree of sequence similarity at both the nucleotide and amino acid levels and allows the grouping into the SBEI, SBEIIa and SBEIIb classes. SBEIIa and SBEIIb generally exhibit around 80% sequence identity to each other, particularly in the central regions of the genes. SBEIIa and SBEIIb may also be distinguished by their expression patterns. SBEIIb is generally specifically expressed in endosperm while SBEIIa is present in every tissue of the plant.

In wheat endosperm, SBEI (Morell et al, 1997) is found exclusively in the soluble fraction, while SBEIIa and SBEIIb are found in both soluble and starch-granule associated fractions (Rahman et al., 1995). In maize and rice, high amylose phenotypes have been shown to result from lesions in the SBEIIb gene, also known as the amylose extender (ae) gene (Boyer and Preiss, 1981, Mizuno et al., 1993; Nishi et al., 2001). In these SBEIIb mutants, endosperm starch grains showed an abnormal morphology, amylose content was significantly elevated, the branch frequency of the residual amylopectin was reduced and the proportion of short chains (<DP 17, especially DP8-12) was lower. Moreover, the gelatinisation temperature of the starch was increased. In addition, there was a significant pool of material that was defined as "intermediate" between amylose and amylopectin (Boyer et al., 1980, Takeda, et al., 1993b). In contrast, maize plants mutant in the SBEIIa gene due to a mutator (Mu) insertional element and consequently lacking in SBEIIa protein expression were indistinguishable from wild-type plants in the branching of endosperm starch (Blauth et al., 2001), although they were altered in leaf starch. Similarly, rice plants deficient in SBEIIa activity exhibited no significant change in the amylopectin chain profile in endosperm (Nakamura 2002). In both maize and rice, the SBEIIa and SBEIIb genes are not linked in the genome In maize, the dull1 mutation causes decreased starch content and increased amylose levels in endosperm, with the extent of the change depended on the genetic background, and increased degree of branching in the remaining amylopectin (Shannon and Garwood, 1984). The gene corresponding to the mutation was identified and isolated by a transposon-tagging strategy using the transposon mutator (Mu) and shown to encode the enzyme designated starch synthase II (SSII) (Gao et al., 1998). The enzyme is now recognized as a member of the SSIII family in cereals (Li et al., 2003). Mutant endosperm had reduced levels of SBEIIa activity associated with the dull1 mutation. No corresponding mutation has been reported in other cereals. It is not known if these findings are relevant to other cereals, for example wheat.

WO94/09144 suggests the use of sense and antisense genes to alter the natural ratios of starch synthase (SS) and SBE in maize. However, no data are presented to substantiate the proposed molecular strategies and there is no suggestion of specifically reducing the activity of SBEIIa.

In potato, down regulation of SBEI alone causes minimal affects on starch structure (Filpse et al., 1996), although further work identified some qualitative changes (Safford et al., 1998). However, in potato the down regulation of SBEII and SBEI in combination increased the relative amylose content much more than the down-regulation of SBEII alone (Schwall et al., 2000).

Two types of debranching enzymes are present in higher plants and are defined on the basis of their substrate specificities, isoamylase type debranching enzymes, and pullulanase type debranching enzymes (Myers et al., 2000). Sugary-1 mutations in maize and rice are associated with deficiency of both debranching enzymes (James et al., 1995, Kubo et al., 1999) however the causal mutation maps to the same location as the isoamylase-type debranching enzyme gene. Representative starch biosynthesis genes that have been cloned from cereals are listed in Table 1.

effects of resistant starch result from the provision of a nutrient to the large bowel wherein the intestinal microflora are given an energy source which is fermented to form inter alia short chain fatty acids. These short chain fatty acids provide nutrients for the colonocytes, enhance the uptake of certain nutrients across the large bowel and promote physiological activity of the colon. Generally if resistant starches or other dietary fibre is not provided the colon is metabolically relatively inactive.

Whilst chemically or otherwise modified starches can be utilised in foods that provide functionality not normally afforded by unmodified sources, such processing has a tendency to either alter other components of value or carry the perception of being undesirable due to processes involved in modification. Therefore it is preferable to provide sources of constituents that can be used in unmodified form in foods.

More wheat is produced in the world each year than for any other cereal grain crop. Known variation in wheat starch structure is limited relative to the variation available in maize

TABLE 1

Starch branching enzyme genes characterized from cereals.

| Species | SBE isoform | Type of clone | Accession No. | Reference |
|---|---|---|---|---|
| Maize | SBEI | cDNA | U17897 | Fisher et al., 1995 |
| | | genomic | AF072724 | Kim et al., 1998a |
| | SBEIIb | cDNA | L08065 | Fisher et al., 1993 |
| | | genomic | AF072725 | Kim et al., 1998 |
| | SBEIIa | cDNA | U65948 | Gao et al., 1997 |
| Wheat | SBEII | cDNA | Y11282 | Nair et al., 1997 |
| | SBEI | cDNA and genomic | AJ237897 SBEI gene) AF002821 (SBEI pseudogene | Baga et al., 1999 Rahman et al., 1997, |
| | | | AF076680 (SBEI gene) AF076679 (SBEI cDNA) | Rahman et al., 1999 |
| | SBEI | cDNA | Y12320 | Repellin et al., 1997 |
| | SBEIIa | cDNA and genomic | AF338432 (cDNA) AF338431 (gene) | Rahman et al., 2001 |
| | SBEIIb | cDNA and genomic | | WO 01/62934 |
| | SBEIIb | cDNA | | WO 00/15810 |
| Rice | SBEI | cDNA | D10752 | Nakamura and Yamanouchi, 1992 |
| | SBEI | genomic | D10838 | Kawasaki et al., 1993 |
| | RBE3 | cDNA | D16201 | Mizuno et al., 1993 |
| Barley | SBEIIa and SBEIIb | cDNA and genomic | AF064563 (SBEIIb gene) AF064561 (SBEIIb cDNA) AF064562 (SBEIIa gene) AF064560 (SBEIIa cDNA) | Sun et al., 1998 |

Starch is widely used in the food, paper and chemical industries. The physical structure of starch can have an important impact on the nutritional and handling properties of starch for food or non-food or industrial products. Certain characteristics can be taken as an indication of starch structure including the distribution of amylopectin chain length, the degree and type of crystallinity, and properties such as gelatinisation temperature, viscosity and swelling volume. Changes in amylopectin chain length may be an indicator of altered crystallinity, gelatinisation or retrogradation of the amylopectin.

Starch composition, in particular the form called resistant starch which may be associated with high amylose content, has important implications for bowel health, in particular health of the large bowel. Accordingly, high amylose starches have been developed in certain grains such as maize for use in foods as a means of promoting bowel health. The beneficial or rice, in part because the transformation efficiency of wheat has lagged behind that for other cereals, and because of the hexaploid nature of breadwheat. The presence of three genomes in Triticum aestivum has a buffering effect by masking mutations in individual genomes, in contrast to the more readily identified mutations in diploid species. Mutants in SBEIIb, corresponding to the amylose-extender phenotypes in maize or rice, have not been characterized in wheat. The phenotype conferred by SBEIIa or SBEIIb mutations in wheat is unknown. Known mutants are for the waxy gene (GBSS, Zhao and Sharp, 1998) and a mutant entirely lacking the SGP-1 protein (Yamamori et al, 2000) which was produced by crossing lines which were lacking the A, B and D genome specific forms of SGP-1 (SSII) protein as assayed by protein electrophoresis. Examination of the SSII null seeds showed that the mutation resulted in alterations in amylopectin structure, deformed starch granules, and an elevated relative amylose content to about 30-37% of the starch, which was an increase of about 8% over the wild-type level (Yamamori et al., 2000). Amylose was measured by colorimetric measurement, amperometric titration (both for iodine binding) and a concanavalin A method. Starch from the SSII null mutant exhibited a decreased gelatinisation temperature compared to starch from an equivalent, non-mutant plant. Starch content was reduced from 60% in the wild-type to below 50% in the SSII-null grain.

WO99/14314 describes the isolation of an SBEIIa gene from *Aegilops tauschii*, a diploid plant related to wheat, but did not produce wheat with altered starch.

WO 00/15810 describes the cloning of cDNAs for a wheat SBEIIb gene. They did not obtain wheat plants with altered amylose levels and did not teach wheat having starch comprising at least 50% amylose.

WO01/62934 also describes a wheat SBEIIb gene and suggests introducing inhibitors of branching enzyme activity into a wheat plant but does not teach wheat having starch comprising at least 50% amylose.

WO 01/32886 characterized a cDNA encoding a form of SBEI in wheat endosperm. The encoded polypeptide was found to be preferentially associated with A-type starch granules. They did not suppress SBEI activity or show altered starch granule morphology or elevated amylose in wheat.

Therefore, wheat having starch with a proportion of amylose greater than about 50% is unknown. Although high amylose maize and barley varieties are known, products from these cereals have disadvantages compared to a very high amylose wheat for products where wheat is the preferred cereal, for example in bread, pasta or noodles.

Whilst elevated amylose starches of these types are useful, a wheat starch with higher amylose contents is preferred, in particular if associated with improved starch synthesis and other characteristics, for example a reduced need for post-harvest modification. Such starch products are also relatively resistant to digestion and bring a greater health benefit.

General

Bibliographic details of the publications referred to by the inventors in this specification are collected at the end of the description. The references mentioned herein are hereby incorporated by reference in their entirety.

As used herein, the term "derived from" shall be taken to indicate that a particular integer or group of integers has originated from the species specified, but has not necessarily been obtained directly from the specified source.

The designation of nucleotide residues referred to herein are those recommended by the IUPAC-IUB Biochemical Nomenclature Commission, wherein A represents Adenine, C represents Cytosine, G represents Guanine, T represents Thymidine.

SUMMARY OF THE INVENTION

In a first aspect the invention provides a grain obtained from a wheat plant wherein the proportion of amylose in the starch of the grain is at least 50%. The wheat plant may have a reduced level of SBEIIa gene expression SBEIIa enzyme activity or both, preferably a reduced level of both SBEIIa and SBEIIb gene expression, enzyme activity or both. The grain might comprise a genetic variation that is either a mutation of an SBEIIa gene which inhibits SBEIIa gene expression, enzyme activity or both or an introduced nucleic acid which inhibits SBEIIa gene expression, enzyme activity or both. Additionally the grain might comprise similar genetic variation in SBEI. The grain might additionally comprise an altered level of a protein and/or enzyme activity selected from the group consisting of ADP glucose pyrophosphorylase, GBSS, SSI, SSII, SSEIII, a debranching enzyme of an isoamylase type and a debranching enzyme of a pullulanase type. The grain might comprise a transgene and the transgene might encode an antisense, co-suppression, ribozyme or duplex RNA molecule. The transgene preferably leads to a reduced level of expression of an mRNA encoding SBEIIa. The grain might comprise a mutation in an SBEIIa gene and in one form is a null mutation of the SBEIIa gene in at least one genome and may be a null mutation in two or three of the genomes. The proportion of amylose in the starch of the grain might be at least 40%, 50%, 55%, 60%, 70% or 80%. In another form at least 50% of starch granules within the grain appear non-birefringent when observed under polarized light. The grain may be non-shrunken, and might have an average weight of at least 36 mg or 40 mg. In an alternative form the starch content of the grain when naked is at least 25% (w/w) or at least 35% (w/w), and may is at least 90% of the starch content of wild type grain. The grain may be whole grains, hulled grain, milled, cracked, rolled, pearled, ground or par boiled grain.

In another form the first aspect the invention provides a grain obtained from a wheat plant, the grain comprising starch and a genetic variation which leads to a reduction in the level of SBEIIa gene expression, SBEIIa enzyme activity in the endosperm or both relative to wild-type grain, which genetic variation comprises a mutation of an SBEIIa gene or an introduced nucleic acid which encodes an inhibitor of SBEIIa gene expression; wherein the proportion of amylose in the starch of the grain is at least 30%.

In a second aspect the invention provides a milled product derived from grain of the first aspect including but not limited to flour, wholemeal, semolina or starch obtained from the grain of the invention, or food products incorporating such flour, wholemeal, semolina, or starch or rolled, flaked or extruded products of the grain. The product may include flour, wholemeal, semolina, or starch obtained from the grain of the first aspect of the invention blended with flour, wholemeal, semolina, or starch from another source.

In a third aspect the invention provides a starch granules or starch obtained from grain of the wheat plant of the first aspect. In a specific form of the third aspect, the wheat plant additionally has a reduced level of SBEIIa enzyme activity in the endosperm.

In a fourth aspect the invention might be said to reside in a composition comprising the starch according to the third aspect of the invention and a food ingredient or water. This aspect includes foods and non-food compositions and blends of the starch with other starches or starch-containing products.

In a fifth aspect the invention provides a composition comprising starch granules of the fourth aspect of the invention above and another food ingredient or water.

In a sixth aspect the invention provides a wheat plant which may be used to produce the grain or the starch granules or the starch of the previous aspects. The wheat plant may be transgenic or non-transgenic, as may be the grain it produces.

In a seventh aspect the invention provides a method of producing a wheat plant capable of producing grain comprising the steps of i) introducing a genetic variation into a parent wheat plant or seed; and ii) identifying a progeny plant or seed of the parent wheat plant or seed which has a reduced level of SBEIIa gene expression, SBEIIa enzyme activity in the endosperm or both relative to a wild-type plant or seed; wherein the grain comprises starch, wherein the proportion of amylose in the starch of the grain is at least 50%.

In a second form of the seventh aspect the invention provides a method of producing a wheat plant capable of producing grain comprising the steps of i) introducing a genetic variation into a parent wheat plant or seed, wherein the genetic variation comprises a mutation of an SBEIIa gene or an introduced nucleic acid which encodes an inhibitor of SBEIIa gene expression, and ii) identifying a progeny plant or seed of the parent wheat plant or seed which has a reduced level of SBEIIa gene expression, SBEIIa enzyme activity in the endosperm or both relative to wild-type grain; wherein the grain comprises starch and wherein the proportion of amylose in the starch of the grain is at least 30%. The step of introducing the genetic variation may comprise introducing an exogenous nucleic acid expressing an inhibitor of SBEIIa gene expression or may comprise mutagenesis of the parent wheat plant.

In a third form of the seventh aspect the invention provides a method of producing a wheat plant capable of producing grain comprising the steps of i) introducing a genetic variation into a parent wheat plant or seed, wherein the genetic variation comprises a mutation of an SBEIIa gene, and ii) identifying a progeny plant or seed of the parent wheat plant or seed which has a reduced level of SBEIIa gene expression, SBEIIa enzyme activity in the endosperm or both relative to wild-type grain; iii) introducing a genetic variation into a parent wheat plant or seed, wherein the genetic variation comprises a mutation of an SBEIIb gene, and iv) identifying a progeny plant or seed of the parent wheat plant or seed which has a reduced level of SBEIIb gene expression, SBEIIa enzyme activity in the endosperm or both relative to wild-type grain; v) crossing a plant having a reduced level of SBEIIa gene expression, SBEIIa enzyme activity in the endosperm or both, with a plant having a reduced level of SBEIIb gene expression, SBEIIb enzyme activity in the endosperm or both; and identifying a wheat plant having reduced gene expression. enzyme activity or both, of both SBEIIa and SBEIIb.

In a fourth form of the seventh aspect the invention provides a method of producing a wheat plant having a relative amylose content in starch of its grain of at least 50%, preferably having reduced activity of SBEIIa enzyme activity in the endosperm, which method comprises: a) identifying a wheat plant or grain having reduced SBEIIa activity expressed from the A, B or D genome of wheat; and b) crossing said wheat plant or a wheat plant produced from the grain of step a) with a second wheat plant having reduced SBEIIa activity; or c) crossing a plant having reduced SBEIIa enzyme activity with a plant having reduced SBEIIb enzyme activity; and identifying a wheat plant having reduced activity of both SBEIIa and SBEIIb. Preferably the plant of the seventh aspect is *Triticuin aestivum* ssp. *aestivum*.

In an eight aspect, the invention provides a method of making altered starch, comprising altering a plant by the methods defined above and extracting the starch having altered properties.

In a ninth aspect the invention provides a method of identifying a wheat plant or seed for a mutation in an SBEIIa gene, or an SBEIIb gene, comprising the steps of screening a population of wheat plants or seed with a molecular marker that is linked to the SBEIIb gene, or SBEIIa gene, respectively, of wheat; and identifying the plant or seed on the basis of the presence or absence of the linked molecular marker.

In a second form of the ninth aspect, the invention provides a method of identifying a wheat plant or seed for a mutation in an SBEIIa gene, or an SBEIIb gene, comprising the steps of screening a population of wheat plants or seed with an antibody that is specific for SBEIIb protein, or SBEIIa protein, respectively, of wheat; and identifying the plant or seed on the basis of the presence or absence of antibody binding. In a tenth aspect, the invention provides grain obtained from a wheat plant, comprising a mutation wherein the SBEIIa gene is absent from the long arm of chromosome 2A or wherein the SBEIIa gene on the long arm of chromosome 2A comprises a mutation which leads to reduced SBEIIa protein, SBEIIa-enzyme activity, or both, in the endosperm of said grain relative to wild-type grain. The mutation may be a null mutation of the SBEIIa gene or may be a deletion of at least part of the SBEIIa gene. The grain may further comprise a mutation wherein the SBEIIb gene is absent from the long arm of chromosome 2A or wherein the SBEIIb gene on the long arm of chromosome 2A comprises a mutation which leads to reduced SBEIIb protein, SBEIIb enzyme activity, or both, in the endosperm of said grain relative to wild-type grain. The deletion may disrupt expression of both the SBEIIa and SBEIIb genes on the long arm of chromosome 2A.

The plant may be a durum wheat plant that may further comprise a genetic variation which leads to reduced starch branching enzyme activity encoded by the SBEIIa gene on the long arm of chromosome 2B relative to wild-type grain. The further genetic variation may comprise an absence of the SBEIIa gene from the long arm of chromosome 2B or a mutation of the SBEIIa gene of the long arm of chromosome 2B which leads to reduced SBEIIa enzyme activity in the endosperm of said grain relative to wild-type grain.

The plant may be *Triticum aestivum* ssp *aestivum* that perhaps additionally comprises a genetic variation which leads to reduced starch branching enzyme activity encoded by the SBEIIa gene on the long arm(s) of chromosome 2B, chromosome 2D or both chromosomes relative to wild-type grain. The further genetic variation comprises an absence of the SBEIIa gene from at least one of said chromosomes or a mutation of the SBEIIa gene of at least one of said chromosomes which leads to reduced SBEIIa enzyme activity in the endosperm of said grain relative to wild-type grain.

The plant may have introduced nucleic acid which encodes an inhibitor of SBEIIa gene expression, activity or both. The level of SBEIIa enzyme activity may reduced by at least 40% relative to wild-type grain. The proportion of amylose in the starch of the grain may be at least 30% or at least 50%. The grain may be non-shrunken and may have an average weight of at least about 36 mg. At least 50% of starch granules from the grain may appear non-birefringent when observed under polarized light. The starch content of the grain when naked, in one form of the invention, is at least 25% (w/w) or has a starch content that is at least 90% of the starch content of wild-type grain.

The amylopectin of the grain of any of the forms of the present invention may have a reduced proportion of the 4-12 dp chain length fraction relative to the amylopectin of wild-type grain, as measured after isoamylase debranching of the amylopectin.

The grain may further comprising a reduced level of SBEI protein, SBEI enzyme activity or both and may further comprise an altered level of an enzyme relative to wild-type grain, wherein said enzyme is selected from the group consisting of ADP glucose pyrophosphorylase, GBSS, SSI, SSII, SSIII, a debranching enzyme of an isoamylase type, a debranching enzyme of a pullulanase type and any combination of these.

Forms of this tenth aspect of the invention encompass grain, starch granules extracted from the grain, and a product

BRIEF DESCRIPTION OF THE DRAWINGS

FIG. 1. Sequence of the Starch Branching Enzyme IIa gene (wSBE II-D1) [SEQ ID No. 1] from *A. tauschii*, corresponding to the D genome SBEIIa gene of hexaploid wheat (*T. aestivum*).

FIG. 2. Partial wheat SBEIIb gene sequence (wbe2b genomic) [SEQ ID No. 2] from *T. aestivum*.

FIG. 3. Schematic of duplex-RNA constructs. A. The order of the gene elements used were promoter, SBEIIa or SBEIIb gene sequence (exons 1, 2 and 3) in sense orientation, intron (intron 3), SBEIIa or SBEIIb gene sequence (exons 1, 2, 3 and 4) in antisense orientation, and transcription terminator/polyadenylation sequence. B. The transcript of the ds-SBEIIa and ds-SBEIIb genes forms a "hairpin" RNA structure with a double-stranded region formed by hybridization between the sense and antisense sequences. The intron sequence bordered by the GT and AG nucleotides is spliced out.

FIG. 4. Starch granules observed through a light microscope from A) a wheat seed with wild type starch granules from the ds-SBEIIa transgenic line 83.1b, B) a wheat seed with distorted starch granules from the ds-SBEIIa transgenic line 50.1b.

FIG. 5. Birefringence of starch granules from wheat seed as for FIG. 4, visualized under polarized light.

FIG. 6. Comparison of partial wheat SBEIIa cDNA sequences. sbe9 corresponds to part of AF338432.1 Partial sequences of the following are shown Y11282 [SEQ ID No. 3], sr997 [SEQ ID No. 4], sr995 [SEQ ID No. 5], sbe9 [SEQ ID No. 6].

FIG. 8. Comparison of the deduced amino acid sequences of the D-genome polypeptide (sr854) [SEQ ID No. 7] with the product from the A or B genome (y11282) [SEQ ID No. 8]. The transit sequence (positions 1-54) is italicized.

FIG. 13. A) FISH using a wSBEII-DA1 probe and a repetitive DNA sequence probe (pSc 119.2) to *A. tauschii* chromosomes (main photograph and lower insert) and wheat chromosomes (upper insert). B) FISH of SBEIIb probe to wheat chromosomes.

FIG. 20. Sepharose CL 2B gel chromatogram of starch from wheat lines a)Acc144008 and b) Acc144087, assayed using starch assay kit (Sigma).

DETAILED DESCRIPTION OF THE INVENTION

Alteration of SBEIIa in Wheat

Figure 7:
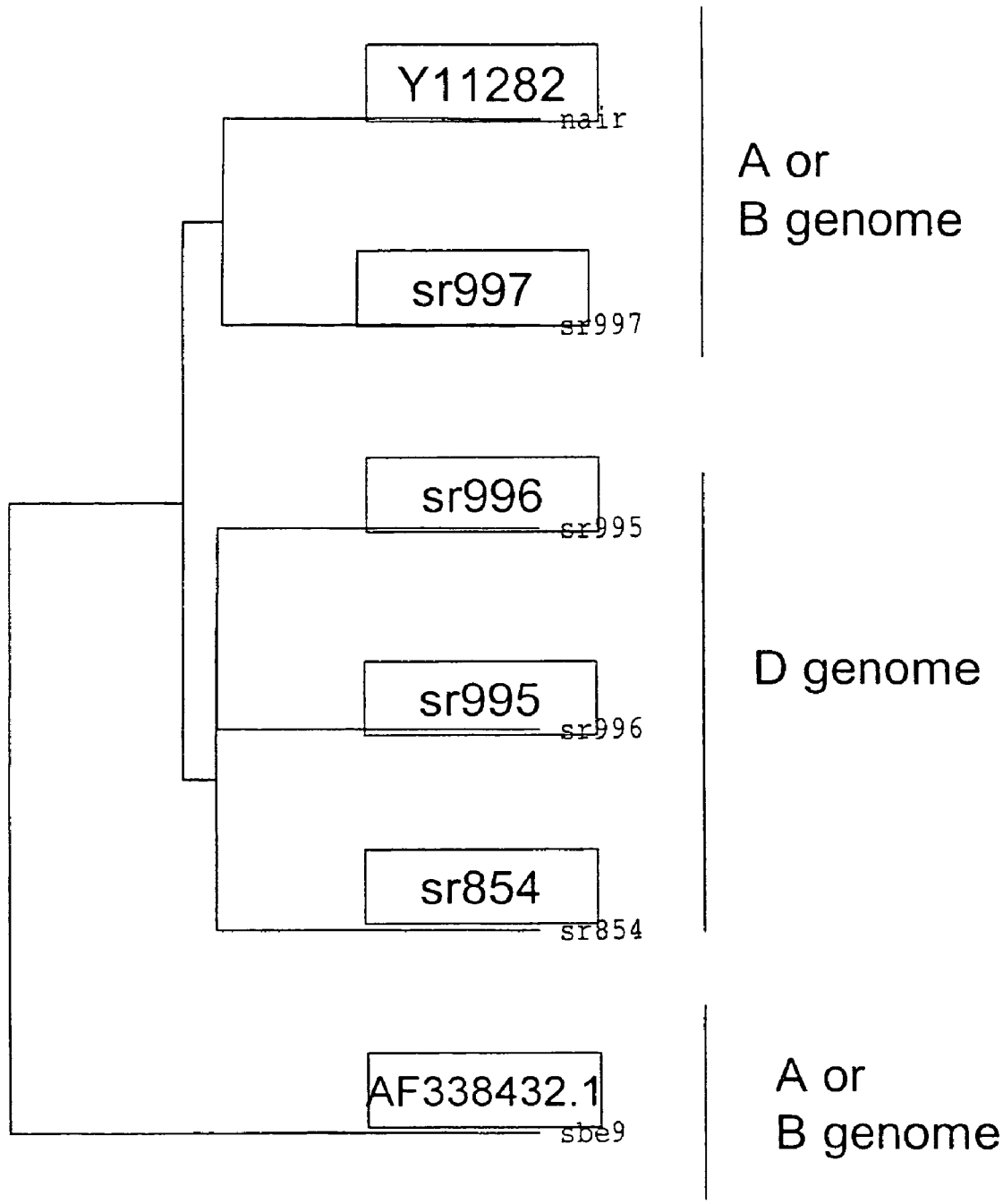
FIG. 7. PILEUP comparison of partial wheat SBEIIa sequences based on the first 63 amino acids. The probable genome location of the genes corresponding to the clones is indicated.

The invention is based on the finding that a reduction in SBEIIa activity in wheat endosperm results in modified starch production, particularly high relative amylose levels in the wheat grain. This unexpected result is in contrast to the findings in maize and rice where mutation in SBEIIa did not alter the amylopectin/amylose profile (Blauth et al., 2001, Nakamura, 2002). In a further embodiment, there is an alteration in one or more additional starch biosynthetic enzyme activities, such as a reduction in SBEIIb as well as SBEIIa activity. Mutation in the genes encoding these two activities is aided by the surprising finding that SBEIIa and SBEIIb are closely linked in wheat, in contrast to non-linkage in maize and rice. We have also found, unexpectedly, that grain of the wheat plant which has reduced levels of SBEIIa and SBEIIb activity is non-shrunken.

Method of Producing a Wheat Plant

In one aspect, the invention provides a method of producing a wheat plant having altered starch in its grain, in particular of increasing the proportion of amylose in the starch to at least 30%. Ordinarily in hexaploid and durum wheats, the proportion of amylose in starch ranges from about 18 to about 30%, in certain mutants (SGP-1 deficient) up to about 35%. In one embodiment, the method of the invention comprises the step of introducing a genetic variation into a parent wheat plant or seed, to provide wheat plants that produce grain having starch comprising at least 30% amylose. The proportion of amylose in the starch as defined herein is on a weight/weight (w/w) basis, i.e. the weight of amylose as a percentage of the weight of starch from the grain. In further embodiments, the proportion of amylose in the starch is at least 40%, at least 50%, at least 55%, at least 60%, at least 65%, at least 70% or at least 75% (each w/w). In further embodiments of the invention, the method provides for a proportion of amylose of at least 80% or at least 90% (w/w).

In a further embodiment, the method includes altering, preferably reducing, the level of starch branching enzyme IIIa (SBEIIa) protein, enzyme activity or both in the endosperm of wheat. That is, a genetic variation that is introduced into the wheat plant leads, directly or indirectly, to the change in the level of SBEIIa and consequently to the starch modifications described herein. In a further embodiment which is not mutually exclusive with the previous embodiment, the method comprises the alteration, preferably reduction, of the level of expression of the SBEIIa gene in the endosperm of wheat, or it comprises the mutation of an SBEIIa gene in wheat, whereby the SBEIIa activity in endosperm is reduced. A reduction in the level of SBEIIa gene expression or of other genes may be achieved by the introduction of a nucleic acid, for example a transgene, which encodes an inhibitory molecule. Examples of inhibitory molecules include antisense, co-suppression, ribozyme or duplex RNA molecules. As used herein, the terms "altering", "increasing", "increased", "reducing", "reduced", "inhibited" or the like are considered relative terms, i.e. in comparison with the wild-type or unaltered state. The "level of a protein" refers to the amount of a particular protein, for example SBEIIa, which may be measured by any means known in the art such as, for example, Western blot analysis or other immunological means. The "level of an enzyme activity" refers to the amount of a particular enzyme measured in an enzyme assay. It would be appreciated that the level of activity of an enzyme might be altered in a mutant but not the expression level (amount) of the protein itself. Conversely, the amount of protein might be altered but the activity remain the same if a more or less active protein is produced. Reductions in both amount and activity are also possible such as, for example, when a gene encoding the enzyme is inactivated. In certain embodiments, the reduction in the level of protein or activity is by at least 40% or by at least 60% compared to the level of protein or activity in the endosperm of unmodified wheat, or by at least 75%, at least 90% or at least 95%. The reduction in the level of the protein or enzyme activity or gene expression may occur at any stage in the development of the grain, particularly during the grain filling stage while starch is being synthesized in the developing endosperm, or at all stages of grain development through to maturity.

"Starch" is defined herein as polysaccharide made up essentially of α-glucopyranose units. Starch is the major storage carbohydrate in wheat, is synthesized in the amyloplasts and formed and stored in granules. It includes amylose, an essentially linear α-1,4-D-glucopyranose polymer and amylopectin, which has short chains of α-D-glucopyranose units primarily linked by α-1,4 bonds with α-1,6 linked branches. Wheat starch from wild-type plants comprises up to about 20%-30% of amylose and about 70%-80% of amylopectin. A further significant difference between the two molecules is their molecular weight. Amylose has a helical conformation with a molecular weight of $10^4$-$10^6$ while amylopectin has a molecular weight of about $10^7$ to $10^8$ daltons. Recent studies have shown up to about 0.1% of α-1,6-glycosidic branching sites may occur in amylose, therefore it is described as "essentially linear". "Amylose" is defined herein as including essentially linear molecules composed of α-1,4 linked glucosidic (glucopyranose) units and amylose-like long-chain amylopectin (sometimes referred to as "intermediate material" or "amylose-like amylopectin", Takeda et al., 1993b; Fergason, 1994). Amylose content may be determined by any of the methods known in the art including size exclusion HPLC, for example in 90% (w/v) DMSO, concanavalin A methods (Megazyme Int, Ireland), or preferably by iodometric methods, for example as described in Example 1. The HPLC method may involve debranching of the starch (Batey and Curtin, 1996) or not involve debranching. From the grain weight and amylose content, the amount of amylose deposited per grain can be calculated and compared for transgenic and control lines.

In another embodiment, the method comprises the step of determining the amount or the activity of SBEIIa in wheat endosperm using any method known in the art. In a certain embodiment, the level of the protein is measured, for example by immunodetection methods such as Western blotting or ELISA assays, or the level of its corresponding mRNA is measured by methods well known in the art such as Northern blot hybridization analysis or reverse transcription polymerase chain reaction (RT-PCR). In another embodiment, the method comprises the step of selecting or screening for a wheat plant or grain having an altered level of SBEIIa protein or enzyme activity in its endosperm. The selection step may be based on a reduced level of the SBEIIa activity or protein, or it may be based on the phenotype of the grain of the wheat plant such as an increased proportion of amylose or decreased proportion of amylopectin, or a visual phenotype, for example shrunken grain or altered starch granule properties.

It would be appreciated that the invention includes a method of identifying a wheat plant with the altered starch properties in its grain using any of the methods as described herein, either directly determining the starch properties or indirectly, for example, detecting the presence of a genetic variation in the plant or its grain. The plant may be a plant in a population of wheat plants, such as, for example, in wheat breeding.

SBE activity may be measured directly by enzyme assay, for example by the phosphorylase stimulation assay (Boyer and Preiss, 1978). This assay measures the stimulation by SBE of the incorporation of glucose 1-phosphate into methanol-insoluble polymer (α-D-glucan) by phosphorylase a. SBE activity can be measured by the iodine stain assay, which measures the decrease in the absorbance of a glucan-polyiodine complex resulting from branching of glucan polymers. SBE activity can also be assayed by the branch linkage assay which measures the generation of reducing ends from reduced amylose as substrate, following isoamylase digestion (Takeda et al., 1993a). Preferably, the activity is measured in the absence of SBEI or SBEIIb activity. Isoforms of SBE show different substrate specificities, for example SBEI exhibits higher activity in branching amylose, while SBEIIa and SBEIIb show higher rates of branching with an amylopectin substrate. The isoforms may also be distinguished on the basis of the length of the glucan chain that is transferred. SBE protein may also be measured by using specific antibodies such as those described herein. The SBEII activity may be measured during grain development in the developing endosperm, or alternatively in the mature grain where the protein is still present in equivalent, but unaltered, grain and can be assayed by immunological methods.

In a further aspect, the invention provides a method of altering, preferably reducing, the activity of multiple starch biosynthesis enzymes in wheat endosperm, wherein one of the enzymes is SBEIIa, such that the proportion of amylose in the starch of the grain is at least 50%. In certain embodiments, the levels of both SBEIIa and SBEIIb proteins or enzyme activities are reduced or the levels of all three of SBEIIa, SBEIIb and SBEI are reduced. Other starch biosynthesis enzymes that may be altered in combination with SBEIIa are: SSI, SSII, SSIII. Starch debranching enzymes may also be altered, for example the activity of isoamylase or pullulanase. Any combination of the above enzymes is also provided, so long as SBEIIa is altered. In a further embodiment, the activity of one or more starch biosynthesis enzyme is altered in the plant in tissues other than endosperm, for example the activity of SBEI or SBEII may be increased in leaves to compensate for some loss of activity caused by a transgene encoding an SBEIIa-inhibitory molecule intended primarily for expression in the endosperm. The alteration may be an increase or reduction in amount or an alteration in the timing of expression, for example. Alternatively, starch synthesis may be further improved by the overexpression of one or more starch biosynthetic enzymes in combination with a reduction in SBEIIa. Genes encoding such enzymes may be from any of a variety of sources, for example from bacterial or other sources other than wheat, and may be modified to alter the catalytic properties, for example alteration of the temperature dependence of the enzymes (for example, see WO94/09144).

The high amylose phenotype may be achieved by partial or full inhibition of the expression of the SBEIIa gene, or the SBEIIa and SBEIIb genes. The extent to which the gene or genes are inhibited will in some degree determine the characteristics of the starch made in the wheat grain. Any of a range of gel electrophoresis techniques carried out on the proteins extracted from the modified wheat endosperm will reveal the nature and extent of modification to the SBEIIa and/or SBEIIb activity. Modification may occur as a reduction in SBEIIa and/or SBEIIb activity, complete abolition of enzyme activity, or an alteration in the distribution of the SBEIIb or other enzymes within the endosperm. To carry out these tests, starch may be extracted from the wheat endosperm and the proteins therein analyzed, for example as outlined in Rahman et al, 1995. Techniques well known in the art such as SDS-PAGE and immunoblotting are carried out on the soluble and the starch granule fractions and the results used to identify the plants or grain where modifications have occurred to the SBEIIa and/or SBEIIb enzymes.

Wheat Plants

In a further aspect, the invention provides a wheat plant capable of producing grain having a proportion of amylose in the starch of at least 30%. In further embodiments, the proportion of amylose is at least 40%, at least 50%, at least 55%, at least 60%, at least 65%, at least 70% or at least 80%. In another embodiment, the wheat plant whose grain comprises any of these levels of amylose in its starch, comprises a genetic variation which leads to a reduction in the level of SBEIIa gene expression, SBEIIa enzyme activity in the endosperm, or both, relative to wild-type grain. In a preferred embodiment, the genetic variation comprises a mutation of an SBEIIa gene or an introduced nucleic acid which encodes an inhibitor of SBEIIa gene expression. The inhibitor may comprise an antisense, co-suppression, ribozyme, or duplex RNA or similar molecule that inhibits SBEIIa expression and/or activity.

A wheat plant is defined herein as any plant of a species of the genus *Triticum*, which species is commercially cultivated, including, for example, *Triticum aestivum* L. ssp. *aestivum* (common or bread wheat), other subspecies of *Triticum aestivum*, *Triticum turgidum* L. ssp. *durum* (durum wheat, also known as macaroni or hard wheat), *Triticuni monococcum* L. ssp. *monococcum* (cultivated einkorn or small spelt), *Triticum timopheevi* ssp. *timopheevi*, *Triticum turgigum* L. ssp. *dicoccon* (cultivated emmer), and other subspecies of *Triticum turgidum* (Feldman). The wheat may be hexaploid wheat having an AABBDD type genome, or tetraploid wheat having an AABB type genome. Since genetic variation in wheat according to the invention can be transferred to certain related species including rye and barley by hybridization, the invention also includes the hybrid species thus formed, including triticale that is a hybrid between bread wheat and rye. In a particular embodiment, the wheat plant is of the species *Triticum aestivum*, and preferably of the subspecies *aestivum*. Alternatively, since mutations or transgenes can be readily transferred from *Triticum aestivum* to durum wheat, the wheat is preferably *Triticum turgidum* L. ssp. *durum*.

The invention also provides wheat plants with a reduced level of SBEIIa protein, enzyme activity in the endosperm, or both, the wheat plant being capable of producing grain having starch comprising an increased proportion of amylose compared to starch extracted from wild-type plants. The reduced level of SBEIIa may occur during at least part of the development process of the grain, or throughout the process to maturity. In a further embodiment, the level of SBEIIa is reduced in the endosperm by at least 50%, at least 75%, at least 90% or at least 95% compared to the wild-type. The term "wild-type" has its normal meaning in the field of genetics and includes wheat cultivars or genotypes which are not modified as taught herein.

The invention also provides progeny plants and grain which have the desired characteristics of the parent wheat plants, in genotype and/or phenotype. The invention also extends to any propagating material of the wheat plants that can be used to produce the plants with the desired characteristics, such as cultured tissue or cells.

The invention also encompasses wheat plants that have altered, preferably reduced, SBEIIb or other starch biosynthetic enzymes in addition to reduced SBEIIa activity. Plants having reduced SBEIIa and SBEIIb activities may be produced by crossing a plant reduced for SBEIIa with a plant reduced for SBEIIb, or by introducing a transgene encoding a molecule that inhibits expression of both SBEIIa and SBEIIb genes. Because of the close linkage of the SBEIIa and SBEIIb genes in wheat as revealed herein, plants reduced for both activities may also be produced by identifying varieties lacking the SBEIIa and SBEIIb isoforms encoded by one of the genomes of wheat, and crossing such varieties to produce a plant reduced for the isoforms encoded by at least two genomes.

The invention also encompasses the genetic variations(s) or mutations in other genetic backgrounds or other species which can be hybridised with the wheat plant as described above. The altered (mutant) plants may be crossed with plants containing a more desirable genetic background. After the initial crossing, a suitable number of backcrosses may be carried out to remove the less desirable background. The desired genetic background may include a suitable combination of genes providing commercial yield and other characteristics such as agronomic performance or abiotic stress resistance. The genetic background might also include other altered starch biosynthesis or modification genes, for example genes from other wheat lines that have a shrunken endosperm where the causal gene is not known.

The plants may be transgenic or non-transgenic.

The invention also provides wheat plants comprising a mutation wherein the SBEIIa gene is absent from the long arm of chromosome 2A (2AL) or wherein the SBEIIa gene on the long arm of chromosome 2A comprises a mutation which leads to reduced level of SBEIIa enzyme activity in the endosperm of said grain relative to wild-type grain. Despite an extensive screen of 2400 wheat accessions, the inventors did not find such plants that were naturally occurring, suggesting that selection for retention of the functional SBEIIa gene on 2AL might be happening in nature. However, such plants could be produced and identified after mutagenesis. These plants are non-transgenic which is desirable in some markets. These plants may be bread wheat, durum wheat or other wheat. In a preferred embodiment, the wheat plant comprises a deletion of at least part of the SBEIIa gene, which may extend to at least part of the SBEIIb gene, on the 2AL chromosome. As is understood in the art, hexaploid wheats such as bread wheat comprise three genomes which are commonly designated the A, B and D genomes, while tetrapolid wheats such as durum wheat comprise two genomes commonly designated the A and B genomes. Each genome comprises 7 pairs of chromosomes which may be observed by cytological methods during meiosis. The chromosomes are commonly designated in order according to their size from largest to smallest, chromosome 2 therefore being the second largest chromosome in each genome. Each chromosome has a centromere, which on chromosome 2 is positioned asymmetrically; therefore the two arms of chromosome 2 are designated "short" and "long". The "long arm of chromosome 2A" is defined herein as the region of that chromosome between the centromere and tip along the long arm, in accord with the standard meaning of the term. The terms "long arm of chromosome 2B" and the "long arm of chromosome 2D" are defined in the same way except that they relate to chromosome 2 of the B or D genomes of wheat, respectively.

We have found that the SBEIIa and SBEIIb genes are closely linked on chromosome 2 in wheat. In a particular embodiment, the wheat plant comprises the majority (>50%) of 2AL, which chromosome arm comprises a mutation of at least the SBEIIa gene. That is, chromosome 2AL is essentially present, comprising a mutation in at least the SBEIIa gene of the A genome. The presence of 2AL may be determined by cytological techniques such as, for example, in situ hybridization techniques (see Example 9) or by using 2AL specific molecular markers. In a preferred embodiment, the wheat plant is homozygous for said mutation. The mutation may be a null mutation. The mutation may be a deletion.

In a particular embodiment, the deletion allele is derived from the MLT2B8 or MLT2D1 plants. As the mutant SBEIIa alleles in these plants occur on the 2AL chromosome, these alleles can be introduced into varieties of bread wheat or durum wheat by crossing, and the invention therefore includes such plants, and grain and starch products obtained therefrom. These alleles may be combined with other useful starch biosynthesis genes or alleles, or other useful genetic traits.

The invention clearly extends to methods of producing or identifying such wheat plants or the grain produced by such plants.

Grain

The invention also provides wheat grain comprising an altered starch compared to starch extracted from wild-type wheat grain. Grain is defined herein as essentially mature grain. This includes grain as harvested in a commercial setting. In one embodiment, the altered starch is at least partly a consequence of reduced SBEIIa activity during development of the endosperm of the wheat grain. In a further embodiment, which is not mutually exclusive with the previous embodiment, the grain comprises an increased proportion of amylose (as a percentage of total starch). This may be determined as a reduced proportion of amylopectin in the starch compared to grain from a wild-type plant. Wild-type wheat starch has approximately 20-30% amylose and 70-80% amylopectin. The grain of the invention comprises starch preferably comprising at least 50% (w/w) amylose. In a further embodiment, both SBEIIa and SBEIIb activities are reduced during development of the endosperm. In a further embodiment, the activity of SBEI is also reduced. In further embodiments, the proportion of amylose, as measured by methods well understood in the art, is at least 55%, at least 60%, at least 65%, at least 70%, at least 75%, at least 80% or at least 90% (each w/w) of the starch of the grain. Increased amylose levels may be evidenced by abnormal starch granule morphology or loss of birefringence of the granules when observed under a light microscope or other methods known in the art. In a particular embodiment, the proportion of amylose is measured by an iodometric method, which may be a spectrophotometric method such as, for example, the method of Morrison and Laignelet (1983), or by high-performance liquid chromatography (HPLC, for example, Batey and Curtin, 1996).

In further embodiments, the wheat grain comprises starch that has altered physical characteristics such as, for example, an increased or reduced gelatinisation temperature, altered swelling characteristics during or following gelatinisation, altered viscosity, an altered chain length distribution in the amylopectin, or any combination of these. The increased or reduced gelatinisation temperature may be for the first peak of gelatinisation, the second peak, or both. One or more properties of the starch such as, for example, the enthalpy of gelatinisation, may be unaltered. The temperature of the first peak (apex) of gelatinisation as measured by differential scanning calorimetry may be increased by at least 3° C. or 5° C., preferably by at least 7° C. or 8° C. and more preferably by at least 10° C. compared to the temperature of the first peak for the corresponding starch from wild-type grain. In a particular embodiment, the increase is in the range of 3° C. to 12° C.

The grain may be shrunken or non-shrunken, preferably having a non-shrunken phenotype. "Non-shrunken" as used herein is defined as where the majority of grains, preferably at least 90% of the individual grains, show a plump or fully-filled phenotype. This is usually associated with a normal or near normal level of starch accumulation. In contrast, a "shrunken" phenotype as used herein refers to the majority of grains, particularly at least 90% of the grains, having reduced starch accumulation. Slightly shrunken grain refers to a reduction in average starch content of at least 30%, moderately shrunken grain refers to a reduction in average starch content of at least 50%, and highly shrunken grain refers to a reduction in average starch content of at least 70%, each relative to wild-type grain. Shrunkenness may also be measured by the relative starch content, as a percentage of mature grain weight. Unaltered field-grown wheat grain has a starch content of about 65%, while in shrunken grain this is reduced to less than 50%.

In further embodiments, the grain has an average weight of at least 36 mg or 40 mg. The average weight of the grain is determined by measuring the weight of a known number of grains, being a representative sample of the batch of grain, and dividing the total weight by the number of grains. It would be appreciated that characteristics of the grain such as starch content, average weight and a non-shrunken phenotype that are near wild-type levels are desirable for commercial production of the grain.

The invention also provides flour, meal, dough or other products produced from the grain or using the grain. These may be unprocessed or processed, for example by fractionation or bleaching. The invention further provides wheat grain useful for food production obtained from the wheat plant of the invention. Additionally the invention encompasses grain that has been processed in other ways, so that the grain may have been milled, ground, rolled, pearled, kibbled or cracked, or par boiled (polenta), for example as cous cous.

Starch

In another aspect, the invention provides starch obtained from the grain of the wheat plants as described herein, the starch having an increased proportion of amylose and a reduced proportion of amylopectin. In a preferred embodiment, the starch is obtained from grain of a wheat plant which has a reduced level of SBEIIa protein, SBEIIa enzyme activity in the endosperm, or both, relative to wild-type wheat. In a further embodiment, both SBEIIa and SBEIIb activities are reduced, or all three of SBEIIa, SBEIIb and SBEI are reduced relative to wild-type wheat.

In a further aspect, the invention provides starch obtained from the grain of the wheat plants as described herein, comprising at least 50%, at least 55%, at least 60%, at least 65%, at least 70%, at least 75%, at least 80% or at least 90% amylose. The starch is at least partly purified, i.e. it has been separated from at least one other component of the grain. Purified starch may be obtained from grain by a milling process, for example a wet milling process, which involves the separation of the starch from protein, oil and fibre. The initial product of the milling process is a mixture or composition of starch granules, and the invention therefore encompasses such granules, comprising the modified starch as described herein.

The starch may have an increased or reduced gelatinisation temperature, preferably an increased gelatinisation temperature. In particular embodiments, at least one of the temperature of onset of the first peak or the temperature for the apex of the first peak is increased by at least 3° C., at least 5° C., at least 7° C. or at least 10° C. as measured by DSC compared to starch extracted from wild-type wheat grain. In a particular embodiment, the increase is in the range of 3° C. to 12° C. Of particular note, the gelatinisation temperature may have a decreased temperature of onset of the first peak combined with an increased temperature of the peak apex. In another embodiment which is not mutually exclusive with the previous, the starch has an altered gelatinisation temperature for the first peak but exhibits a substantially unaltered temperature for the second peak, which corresponds to amylose-lipid dissociation, as determined by DSC. In a further embodiment, the starch exhibits a decreased enthalpy during gelatinisation, such as, for example, a decrease by at least 25% or at least 40% compared to that of corresponding wild-type wheat starch.

In another embodiment, the starch comprises an elevated level of resistant starch, with an altered structure indicated by specific physical characteristics. Such characteristics may include physical inaccessibility to digestive enzymes which may be by reason of having altered starch granule morphology, the presence of appreciable starch associated lipid, altered crystallinity, altered amylopectin chain length distribution, or any combination of these. The high proportion of amylose also contributes to the level of resistant starch.

The invention also provides starch from grain of the exemplified wheat plant comprising increased amounts of dietary fibre, preferably in combination with an elevated level of resistant starch. This increase is also at least in part a result of the high relative level of amylose.

The invention clearly extends to methods of producing the wheat starch described herein. In one embodiment, the method comprises the steps of obtaining wheat grain as described herein and extracting the starch from the grain. The wheat grain may be obtained by growing the wheat plants described herein and harvesting the grain, or from a producer of the grain or importer of the grain.

Methods of Reducing Gene Activity

The expression and/or activity of SBEIIa, SBEIIb or other starch biosynthesis or modification genes may be altered by introducing one or more genetic variations into the wheat plant. As used herein, a "genetic variation" means any heritable alteration in the genome of the wheat plant which, in this context, affects the expression or activity of the gene of interest. Genetic variations include mutations such as point mutations, insertions, substitutions, inversions, duplications, translocations and preferably deletions, and the introduction of one or more transgenes into the genome.

The phrases "nucleic acid molecule" and "nucleic acid sequence" as used herein refer to a polymer of nucleotides, which may be single-stranded or double-stranded. It may comprise DNA such as, for example, genomic DNA or cDNA, or RNA, mRNA or any combinations of these. For introduction into wheat cells, a nucleic acid molecule may be chemically modified for improved delivery or stability, or protected as part of a vector such as a viral vector. The nucleic acid molecule may be obtained by cloning techniques or synthesized by techniques well known in the art. The nucleic acid molecule may comprise a coding strand or non-coding strand (antisense) or a combination of these such as, for example, in inverted repeat constructs. In reference to nucleic acid sequences which "correspond" to a gene, the term "correspond" refers to a nucleotide sequence relationship, such that the nucleotide sequence has a nucleotide sequence which is the same as the reference gene or an indicated portion thereof, or has a nucleotide sequence which is exactly complementary in normal Watson-Crick base pairing, or is an RNA equivalent of such a sequence, for example, an mRNA, or is a cDNA derived from an mRNA of the gene.

Nucleotide sequences are presented herein by a single strand sequence in the 5' to 3' direction, using the standard one letter nucleotide abbreviations. "Complementary" describes the relationship between two single-stranded nucleic acid molecules or sequences that anneal by base-pairing. For example, 5'-GACT-3' pairs with its complement, 5'-AGTC-3'. "Homology" or "homologous" refers to sequence similarity or identity between two or more nucleotide sequences or two or more polypeptide sequences, according to the context. The term "percent identity" as applied to nucleotide sequences refers to the percentage of nucleotide matches between two nucleotide sequences aligned using a standardized algorithm such as, for example, the CLUSTAL V algorithm or the Blastn or BLAST 2 Sequences programs available from the National Center for Biotechnology Information, available on the Internet at ncbi.nlm.nih.gov/BLAST/, and preferably set at default parameters. In similar fashion, "percent identity" may refer to polypeptide sequences.

Reference herein to a "gene" including an SBEIIa, SBEIIb or other starch biosynthetic gene, or genes encoding antisense, co-suppression, ribozyme, duplex RNA molecules or the like, is to be taken in its broadest context and includes a classical genomic gene having a transcribed region associated with regulatory regions such as promoters and transcription terminators-polyadenylation sequences. The transcribed region includes transcribed but not translated sequences (untranslated sequences, UTR) and optionally may include a protein coding region or introns, which are spliced out to form a mature RNA, or any combination of these. A "gene" includes forms obtained from cDNA, corresponding to the exons, and RNA genes such as those found on RNA genomes. The term "gene" is also used to describe synthetic or fusion molecules encoding all or part of a functional product.

When present in a cell, preferably a wheat cell, a "gene" directs the "expression" of a "biologically active" molecule or "gene product", which may be RNA or a polypeptide. This process is most commonly by transcription to produce RNA and translation to produce protein. Such a product may be subsequently modified in the cell. RNA may be modified by, for example, polyadenylation, splicing, capping, dicing into 21-23 nucleotide fragments, or export from the nucleus or by covalent or noncovalent interactions with proteins. Proteins may be modified by, for example, phosphorylation, glycosylation or lipidation. All of these processes are encompassed by the term "expression of a gene" or the like as used herein.

As used herein, the terms "wheat SBEIIa gene" and "wheat SBEIIb gene" and related terms refer to the genes that have been identified from wheat that encode SBEIIa or SBEIIb enzymes, respectively, and homologous genes present in other wheat varieties. These include, but are not limited to, the gene sequences listed in Table 1. It would be understood that there is natural variation in the sequences of SBEIIa and SBEIIb genes from different wheat varieties. The homologous genes are readily recognizable by the skilled artisan. The degree of sequence identity between homologous SBEIIa genes or the proteins is thought to be at least 90%, similarly for SBEIIb genes or proteins.

The genes for use in the invention may be derived from a naturally occurring SBEIIa, SBEIIB or other starch biosynthetic gene by standard recombinant techniques. A "recombinant nucleic acid molecule" or like term as used herein refers to a sequence that is not naturally occurring or has a sequence that is made by an artificial combination of two or more otherwise separated segments of sequence. This artificial combination may be formed by chemical synthesis or, more commonly, by the artificial manipulation of isolated segments of nucleic acids, for example by genetic engineering techniques well known in the art. The term "recombinant" includes nucleic acids that have been altered solely by addition, substitution, or deletion of a portion of the nucleic acid. Frequently, a recombinant nucleic acid may include a nucleic acid sequence operably linked to a promoter sequence. Such a recombinant nucleic acid may be part of a vector that is used, for example, to transform a cell.

Generally, a gene may be subjected to mutagenesis to produce single or multiple nucleotide substitutions, deletions and/or additions such as, for example, codon modification. Nucleotide insertional derivatives of such genes include 5' and 3' terminal fusions as well as intra-sequence insertions of single or multiple nucleotides. Insertional nucleotide sequence variants are those in which one or more nucleotides are introduced into a predetermined site in the nucleotide sequence, although random insertion is also possible with suitable screening of the resulting product. Deletional variants are characterised by the removal of one or more nucleotides from the sequence. Substitutional nucleotide variants are those in which at least one nucleotide in the sequence has been removed and a different nucleotide inserted in its place. Such a substitution may be "silent" in that the substitution does not change the amino acid defined by the codon. Alternatively, conservative substituents are designed to alter one amino acid for another similar acting amino acid. Typical substitutions are those made in accordance with the following:

Suitable residues for conservative amino acid substitutions

| Original Residue | Exemplary Substitutions |
|---|---|
| Ala | Ser |
| Arg | Lys |
| Asn | Gln; His |
| Asp | Glu |
| Cys | Ser |
| Gln | Asn |
| Glu | Asp |
| Gly | Ala |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Transgenes

The expression and/or activity of SBEIIa, SBEIIb or other starch biosynthesis or modification genes may be altered by introducing one or more transgenes into the wheat plant. A "transgene" as referred to herein has the normal meaning in the art of biotechnology and includes a genetic sequence which has been produced or altered by recombinant DNA or RNA technology and which has been introduced into the organism or cell, preferably wheat cell, of interest. The transgene may include genetic sequences derived from the organism or cell, for example an antisense sequence. The transgene typically includes an exogenous nucleic acid which is not derived from said organism or cell. "Transgenic" refers to the organism or cell containing a transgene. "Non-transgenic" refers to the absence of any transgene in the genome. A transgene is preferably integrated into the genome of the organism or cell, for stable inheritance.

Those skilled in the art will be aware that expression of an gene, or a complementary sequence thereto, in a cell, requires said gene to be placed in operable connection with a promoter sequence. The choice of promoter for the present purpose may vary depending upon the level of expression required and/or the tissue, organ and species in which expression is to occur, particularly endosperm specific promoters.

Placing a nucleic acid molecule under the regulatory control of a promoter sequence means positioning said molecule such that expression is controlled by the promoter sequence. A promoter is usually, but not necessarily, positioned upstream, or at the 5'-end, of the nucleic acid molecule it regulates. Furthermore, the regulatory elements comprising a promoter are usually positioned within 2 kb of the start site of transcription of the gene. In the construction of heterologous promoter/structural gene combinations, it is generally preferred to position the promoter at a distance from the gene transcription start site that is approximately the same as the distance between that promoter and the gene it controls in its natural setting (i.e., the gene from which the promoter is derived). As is known in the art, some variation in this distance can be accommodated without loss of promoter function. Similarly, the preferred positioning of a regulatory sequence element with respect to a heterologous gene to be placed under its control is defined by the positioning of the element in its natural setting (i.e., the gene from which it is derived). Again, as is known in the art, some variation in this distance can also occur.

Examples of promoters suitable for use in gene constructs of the present invention include promoters derived from the genes of viruses, yeast, moulds, bacteria, insects, birds, mammals and plants, preferably those capable of functioning in plant cells, more preferably those capable of being expressed in the endosperm of wheat. The promoter may regulate expression constitutively, or differentially, with respect to the tissue in which expression occurs. Alternatively, expression may be differential with respect to the developmental stage at which expression occurs, or in response to external stimuli such as physiological stresses, or temperature.

The method of reducing SBEIIa or other starch biosynthetic gene activity may comprise the step of introducing a transgene into a regenerable cell of wheat and regenerating a transgenic wheat plant from the transformed cell. The branching enzymes involved in synthesis of amylopectin include SBEI, SBEIIa and SBEIIb and the invention encompasses a reduced expression of SBEIIa alone or in combination with alteration of SBEIIb or SBEI expression. Therefore, the transgene(s) may inactivate more than one of these genes. Moreover, the inactivation of SBEIIB and/or SBEI may be direct, in that the transgene (e.g. encoding duplex RNA, antisense, or ribozyme RNA, see below) directly targets the SBEIIb or SBEI gene expression, or it may indirectly result in the alteration in the expression of SBEIIb or SBEI. For example, the transgene RNA may target only the SBEIIa gene/RNA in terms of sequence identity or basepairing but also result in reduction of SBEIIb or SBEI activity by altering protein stability or distribution in the endosperm. Additionally forms of the present invention reside in the combination of an altered activity of SBEIIa and an alteration of one or more other amylopectin synthesis enzymes, which enzymes may include SSI, SSII, SSIII, and debranching enzymes such as isoamylase or pullulanase. Expression of any or all of these may be altered by introduction of a transgene.

Several DNA sequences are known for amylopectin synthesis genes in wheat, any of which can be the basis for designing transgenes for inactivation of the genes in wheat. These include SBEIIa (GenBank accession numbers Y11282, AF338431 and AF338432) and SBEIIb (WO 00/15810, WO 01/62934). The SBEI gene of wheat is described in Rahman et al., (1997) and Rahman et al., (1999). The *Triticum tauschii* sequence for SBEI, which is highly homologous to the wheat D genome SBEI gene, can be found in published Patent specification WO 99/14314. A cDNA sequence for SBEI of wheat can be accessed in the GenBank database under accession number AF076679. Homologues of other amylopectin synthesising genes from barley or other closely related species can also be used to modify gene expression levels in wheat. Such genes or fragments thereof can be obtained by methods well known in the art, including PCR amplification or hybridization to labeled probes.

"Stringent hybridization conditions" as used herein means that hybridization will generally occur if there is at least 90% and preferably at least 95% sequence identity between the probe and the target sequence. Examples of stringent hybridization conditions are overnight incubation in a solution comprising 50% formamide, 5×SSC (1×SSC=150 mM NaCl, 15 mM trisodium citrate), 50 mM sodium phosphate (pH 7.6), 5× Denhardt's solution, 10% dextran sulfate, and 20 µg/ml denatured sheared carrier DNA such as salmon sperm DNA, followed by washing the hybridization support in 0.1×SSC at approximately 65° C. Other hybridization and wash conditions are well known and are exemplified in Sambrook et al, Molecular Cloning: A Laboratory Manual, Second Edition, Cold Spring Harbor, N.Y. (1989), particularly Chapter 11.

The region(s) of the homologues used in preparing the transgene construct should have at least 85% identity to the corresponding wheat gene, preferably at least 90% and even more preferably 95-100% identity in the appropriate region. It is also preferred that the transgene specifically target the amylopectin synthesis genes expressed in the endosperm of wheat and have less or minimal effect on amylopectin synthesis elsewhere in the plant. This may be achieved by use of suitable regulatory sequences such as endosperm-specific promoters in the transgene.

Antisense

Genetic engineering approaches to altering, in particular specifically reducing, gene activity in plants such as wheat are well known in the art. These methods include the introduction of gene constructs for expression of a suitable antisense molecule that is complementary to the RNA of the target gene and can hybridize with it. Antisense molecules are thought to interfere with the translation or processing or stability of the mRNA of the target gene, thereby inactivating expression of the gene. Methods of devising antisense sequences are well known in the art and examples of these can be found in U.S. Pat. No. 5,190,131, European patent specification 0467349-A1, European patent specification 0223399-A1 and European patent specification 0240208, which are incorporated herein by reference. The use of antisense methods in plants has been reviewed by Bourque (1995) and Senior (1998). Bourque lists a large number of examples of gene inactivation using antisense sequences in plant systems. She also states that attaining 100% inhibition of an enzyme activity may not be necessary as partial inhibition will more than likely result in measurable change in the system. Senior (1998) states that antisense methods are now a very well established technique for manipulating gene expression in plants.

Antisense molecules for wheat SBEIIa, SBEIIb, SBEI or other starch biosynthesis or modification genes can be based on the wheat mRNA sequences or derived from homologous DNA or mRNA sequences obtained from other species, for example barley. The antisense sequences may correspond to all or part of the transcripts of any of these genes or for sequences that effect control over their expression, for example their splicing. The antisense sequence may correspond to the targeted coding region of the wheat SBEIIa or other gene, or the 5'-untranslated region (UTR) or the 3'-UTR or combination of these. It may be complementary in part to intron sequences, which may be spliced out during or after transcription, preferably only to exon sequences of the target gene. In view of the generally greater divergence of the UTRs, targeting these regions provides greater specificity of gene inhibition. In particular embodiments, the length of the antisense sequence is at least 19 contiguous nucleotides, at least 50, at least 100, at least 200, at least 500 or at least 1000 nucleotides corresponding to the complement of the gene RNA sequence. The full-length sequence complementary to the entire gene transcript may be used. In a particular embodiment, the length of the antisense sequence is 100-2000 nucleotides. In further embodiments, the degree of sequence identity of the antisense sequence to the complement of the targeted transcript is at least 85%, at least 90% or 95-100%. The antisense RNA molecule may of course comprise unrelated sequences which may function to stabilize the molecule.

Cosuppression

Another molecular biological approach that may be used is co-suppression. The mechanism of co-suppression is not well understood but is thought to involve post-transcriptional gene silencing (PTGS) and in that regard may be very similar to many examples of antisense suppression. It involves introducing an extra copy of a gene or a fragment thereof into a plant in the sense orientation with respect to a promoter for its expression. The size of the sense fragment, its correspondence to target gene regions, and its degree of sequence identity to the target gene are as for the antisense sequences described above. In some instances the additional copy of the gene sequence interferes with the expression of the target plant gene. Reference is made to Patent specification WO 97/20936 and European patent specification 0465572 for methods of implementing co-suppression approaches.

Double Stranded RNA-mediated Gene Silencing

A further method that might be employed to introduce genetic variation into the wheat plant is duplex or double stranded RNA mediated gene silencing. This method also involves PTGS. In this method a DNA is introduced that directs the synthesis of an at least partly double stranded RNA product(s) with homology to the target gene to be inactivated. The DNA therefore comprises both sense and antisense sequences that, when transcribed into RNA, can hybridize to form the double-stranded RINA region.

In a preferred embodiment, the sense and antisense sequences are separated by a spacer region that comprises an intron which, when transcribed into RNA, is spliced out. This arrangement has been shown to result in a higher efficiency of gene silencing. The double-stranded region may comprise one or two RNA molecules, transcribed from either one DNA region or two. The presence of the double stranded molecule triggers a response from an endogenous plant system that destroys both the double stranded RNA and also the homologous RNA transcript from the target plant gene, efficiently reducing or eliminating the activity of the target gene. Reference is made to Australian Patent specification 99/29514-A and Patent specification WO 99/53050 for methods of implementing this technique. In particular embodiments, the length of the sense and antisense sequences that hybridise are at least 19 contiguous nucleotides, at least 30, at least 50, at least 100, at least 200, at least 500 or at least 1000 nucleotides. The full-length sequence corresponding to the entire gene transcript may be used. In a particular embodiment, the lengths are in the range 100-2000 nucleotides. In further embodiments, the degree of sequence identity of the sense and antisense sequences to the targeted transcript is at least 85%, at least 90% or 95-100%. The RNA molecule may of course comprise unrelated sequences which may function to stabilize the molecule. The RNA molecule may be expressed under the control of a RNA polymerase II or RNA polymerase III promoter. Examples of the latter include tRNA or snRNA promoters. The double-stranded RNA molecule may also comprise sequences from more than one gene, joined together, and thereby target multiple genes.

Ribozymes

The genetic variation responsible for the desired inactivation of gene expression in wheat may comprise a nucleic acid molecule encoding one or more ribozymes. Ribozymes are RNA molecules with enzymatic or catalytic function that can cleave other RNA molecules at specific sites defined by one or often two hybridizing sequences. The cleavage of the RNA inactivates the expression of the target gene. The ribozymes may also act as an antisense molecule, which may contribute to the gene inactivation. The ribozymes contain one or more catalytic domains, preferably of the hammerhead or hairpin type, between the hybridizing sequences. Other ribozyme motifs may be used including RNAseP, Group I or II introns, and hepatitis delta virus types. Reference is made to European patent specification 0321201 and U.S. Pat. No. 6,221,661. The use of ribozymes to inactivate genes in transgenic plants has been demonstrated, for example by Wegener et al (1994).

Genetic Constructs/Vectors

The invention also provides isolated nucleic acid molecules comprising RNA or DNA, preferably DNA, which encode the gene-inhibiting molecule. In certain embodiments, the nucleic acid molecules encode antisense, sense (co-suppression), double-stranded RNA or ribozyme molecules which target the wheat SBEIIa gene sequence and which inactivate its expression in endosperm of wheat grain. The invention also provides genetic constructs comprising or encoding the isolated nucleic acid molecule, comprising one or more regulatory elements such as promoters, enhancers and transcription termination or polyadenylation sequences. Such elements are well known in the art. The genetic constructs may also comprise intron sequences that aid expression of the transgene in plants, particularly in monocotyledonous plants such as wheat. The term "intron" is used in its normal sense as meaning a genetic segment that is transcribed but does not encode protein and which is spliced out of an RNA before translation. Introns may be incorporated in a 5'-UTR or a coding region if the transgene encodes a translated product, or anywhere in the transcribed region if it does not.

The invention further provides vectors, for example plasmid vectors, comprising the genetic constructs. The term "vector" includes an expression vector, being capable of in vitro or in vivo expression, and a transformation vector, capable of being transferred from one cell or organism to another. The vectors comprise sequences that provide for replication in cells, for example in prokaryotic cells such as *E. coli* or *Agrobacterium*. In a particular embodiment, the vector is a binary vector comprising a T-DNA sequence, defined by at least one T-DNA border sequence, that can be introduced into wheat cells. The invention further provides cells comprising the vectors, for example *Agrobacterium* or wheat cells which may be regenerable cells such as the cells of the scutellum of immature embryos. Alternatively, the cells may be transformed wheat cells comprising the transgene.

Promoters/Terminators

In another embodiment, the transgene or other genetic construct of the invention includes a transcriptional initiation region (promoter) that may provide for regulated or constitutive expression in the endosperm of wheat. The promoter may be tissue specific, conferring expression selectively or exclusively in the endosperm. The promoter may be selected from either endosperm-specific (such as High Molecular Weight Glutenin promoter, the wheat SSI promoter, wheat SBEII promoter, wheat GBSS promoter) or promoters not specific for the endosperm (such as ubiquitin promoter or CaMV35S or enhanced 35S promoters). The promoter may be modulated by factors such as temperature, light or stress. Ordinarily, the promoter would be provided 5' of the genetic sequence to be expressed. The construct may also contain other elements that enhance transcription such as the nos 3' or the ocs 3' polyadenylation regions or transcription terminators. The regions of DNA illustrated will be incorporated into vectors containing suitable selectable marker gene sequences and other elements, or into vectors that are co-transformed with vectors containing these sequences.

Transformation Methods for Wheat

Methods for transformation of monocotyledonous plants such as wheat, that is for introducing genetic variation into the plant by introduction of an exogenous nucleic acid, and for regeneration of plants from protoplasts or immature plant embryos are well known in the art, see for example, Becker et al 1994, Cheng et al 1997, He et al 1994, Hess et al 1990, Nehra et al 1994, Vasil et al 1992, Vasil et al 1993, Weeks et al 1993, Weir et al 2001, Australian Patent Application No. 75460/94, European Patent Application No. 709462, International Patent Publication Nos. WO93/04178, WO89/12012, WO94/13822 and WO99/14314. Vectors carrying the desired nucleotide sequence or genetic construct and a selectable marker may be introduced into regenerable wheat cells of tissue cultured plants or explants, or suitable plant systems such as protoplasts. The selectable marker gene may provide antibiotic or herbicide resistance to the wheat cells, or allow the utilization of substrates such as mannose. The selectable marker preferably confers asulam, geneticin or hygromycin resistance to the wheat cells. The regenerable wheat cells are preferably from the scutellum of immature embryos, mature embryos, callus derived from these, or the meristematic tissue.

The transformed plant may contain a selectable marker gene, or such gene may be removed during or after regeneration, for example by excision of the selectable marker gene out of the genome or by segregation of the selectable marker gene away from the SBEIIa-inhibiting transgene.

Plants where the transgene or mutation has been integrated into a chromosome can be screened for by, for example, using a suitable nucleic acid probe specific for the transgene or phenotypic observation. Any of several methods may be employed to determine the presence of a transformed plant. For example, polymerase chain reaction (PCR) may be used to amplify sequences that are unique to the transformed plant, with detection of the amplified products by gel electrophoresis or other methods. DNA may be extracted from the plants using conventional methods and the PCR reaction carried out using primers that will distinguish the transformed and non-transformed plants. For example, primers may be designed that will amplify a region of DNA from the transformation vector reading into the construct and the reverse primer designed from the gene of interest. These primers will only amplify a fragment if the plant has been successfully transformed. An alternative method to confirm a positive transformant is by Southern blot hybridization, well known in the art. Plants which are transformed or mutant may also be identified i.e. distinguished from non-transformed or wild-type plants by their phenotype, for example conferred by the presence of a selectable marker gene, or the presence of a particular protein by immunological methods, or by the absence of a protein, for example that absence of the SBEIIa protein in the endosperm as detected by ELISA assay or Western blot analysis. An indication used in screening such plants might also be by observation of the phenotypic traits of the grain, for example by visual inspection or measurement of shrunken grain, or testing for elevated amylose content, or checking microscopically for the presence of birefringence.

Mutation

Introduction of the genetic variation leading to reduced activity of the SBEIIa enzyme or other starch biosynthetic enzyme in the wheat endosperm may also be achieved by the appropriate mutations within the respective gene or regulatory sequences of the gene. In the context of this application, an "induced mutation" is an artificially induced genetic variation which may be the result of chemical, radiation or biologically-based mutagenesis, for example transposon or T-DNA insertion. The extent to which the gene is inhibited will to some degree determine the characteristics of the starch made. The mutations may be truncation or null mutations and these are known to have a significant impact on the nature of the starch, however an altered starch structure will also result from a leaky mutation that sufficiently reduces amylopectin synthesis enzyme activity to provide the characteristic of interest in the starch or grain of wheat. Other chromosomal rearrangements may also be effective and these might include insertions, deletions, inversions, duplication or point mutations. A "null mutation" as used herein refers to a mutation which results in the complete or near complete loss of activity of the gene of interest such as, for example, where the gene activity can no longer be detected.

The SBEIIa gene is located on the long arm of chromosome 2. It is preferred that mutations to the gene or other genes, particularly deletion mutations, are localised to the gene of interest, for example the SBEIIa gene or perhaps extended to the linked SBEIIb gene in the case of a double mutant. A gene in this context includes the promoter region and transcription termination/polyadenylation signals as well as the transcribed region. The transcribed region includes the protein coding region(s) and the 5' untranslated and 3' untranslated regions of the mRNA as well any intron regions that may be present. Mutations to a gene may be in any region of the gene or a combination of regions and might extend from altering only one nucleotide, for example a frameshift mutation in the coding region, to deletion of the entire gene. Plants which are homozygous for the genetic variation are preferred.

Deletions may be restricted in size in the order of one or a few hundred, perhaps 500, kilobases. In certain embodiments, the deletion extends to less than a few thousand kilobases, or less than 5 thousand kilobases. Whilst the invention may encompass larger deletions including much of the long arm of chromosome 2 of the respective genome these are not preferred because the long arm of chromosome 2 has a number of other genes localised thereon that impact on the vigour of the wheat plant. Accordingly, where large deletions occur, these impact adversely on the vigour of the plant and hence on its commercial viability, and it is desired that at least a majority of the long arm of chromosome 2 is present. In a preferred embodiment, the majority of the long arm of chromosome 2A is present.

Mutagenesis can be achieved by chemical or radiation means, for example EMS or sodium azide (Zwar and Chandler, 1995) treatment of seed, or gamma irradiation. Isolation of mutants may be achieved by screening mutagenised plants or seed. For example, a mutagenized population of wheat may be screened for high amylose content in the grain and/or longer than normal amylopectin chain length distribution, or loss of the SBEIIa protein by ELISA, or for altered grain morphology (Green et al., 1997). Screening is preferably done in a wheat genotype that already lacks one of the SBE activities, for example in a SBEIIb-negative background. Such mutations may then be introduced into desirable genetic backgrounds by crossing the mutant with a plant of the desired genetic background and performing a suitable number of backcrosses to cross out the originally undesired parent background.

In another embodiment, the mutation affects the expression or activity of both SBEIIa and SBEIIb genes in wheat. Identifying such a mutation is aided by the unexpected finding that the two genes are closely linked in wheat, in contrast to maize or rice. Deletions in one gene may readily extend to the other gene, providing a null allele (null mutation) for both genes. This knowledge also aids the screening of natural variants that are mutant in both genes on at least one genome of wheat, and more readily allows screening to produce wheat with combined mutations in both genes in two or three genomes. Such wheat provides a high amylose, non-transgenic source of wheat grain and products therefrom.

Mutations in the genes encoding the SBEIIa or other enzymes involved in amylopectin synthesis will generally cause an increased proportion of amylose content. The amount of amylose per individual grain may be increased as a consequence of diverted carbon flow from amylopectin to amylose, or it may be decreased if there is a significant decrease in starch production per grain. In either case, the relative level of amylose as a percentage of starch increases.

Seed with starch granules having a distorted shape have been reported in high amylose barley (Morell et al, 2003) and in low amylopectin (LAPS) maize having about 90% amylose in starch (Sidebottom et al., 1998).

Birefringence is the ability of a substance to refract light in two directions; this produces a dark cross called a "maltese cross" on each starch granule when viewed with a polarizing microscope. Birefringence is an indicator of the degree of ordered structural organization of the polymers within the granules (Thomas and Atwell, 1999). Loss of birefringence in starch granules is generally well correlated with increased amylose content.

Suitable for Food Production

In another aspect, the invention provides wheat that is useful for food production, the grain having starch comprising a high relative amylose content and a reduced amylopectin content. Preferably the wheat plant from which the grain is obtained has a reduced level of SBEIIa activity in the endosperm during development. The wheat plant of the present invention is useful for food production and in particular for commercial food production. Such food production might include the making of flour, dough or other products that might be an ingredient in commercial food production.

The desired genetic background of the wheat will include considerations of agronomic yield and other characteristics. Such characteristics might include whether it is desired to have a winter or spring type of wheat, agronomic performance, disease resistance and abiotic stress resistance. In Australia one might want to cross the altered starch trait into wheat cultivars such as Baxter, Kennedy, Janz, Frame, Rosella, Cadoux, Diamondbird or other commonly grown varieties. The examples provided are specific for an Australian production region, and other varieties will be suited for other growing regions. It is preferred that the wheat variety of the invention provide a yield not less than 80% of the corresponding wild-type variety in at least some growing regions, more preferably not less than 90% and even more preferably not less than 95%. The yield can readily be measured in controlled field trials.

In further embodiments, the starch content of the grain is at least about 25%, 35%, 45%, or 55% to 65% (w/w). Wild-type wheat grown commercially has a starch content usually in the range 55-65%, depending somewhat on the cultivar grown. Alternatively, the grain of the invention has a starch content of at least 90% that of grain from an equivalent, but unaltered, wheat. Lower starch contents than wild-type are likely a consequence of reduced amylopectin levels. Even with lower starch contents, the grain may still be useful for commercial food production because of the relatively high value of the high amylose products. Other desirable characteristics include the capacity to mill the grain, in particular the grain hardness. Another aspect that might make a wheat plant of higher value is the degree of starch extraction from the grain, the higher extraction rates being more useful. Grain shape is also another feature that can impact on the commercial usefulness of a plant, thus grain shape can have an impact on the ease or otherwise with which the grain can be milled. For example, an elongated grain morphology may make it difficult to mill and process.

A fuller grain may be desirable in terms of achieving greater yields and certain benefits of the invention might be achieved, such as the production of starch with high levels of amylose, or in the alternative starch with altered chain length distributions. Thus the grain preferably has a non-shrunken phenotype. Other aspects of the invention may, however, be better achieved by a grain that is less filled. Thus the proportion of aleurone layer or germ or protein to starch may be higher in less filled grain, thereby providing for a wheat flour or other product that is higher in the beneficial constituents of the aleurone layer or protein. The high aleurone layer product might thus be higher in certain vitamins such as folate, or it might be higher in certain minerals such as calcium, and that combined with higher resistant starch levels might provide synergistic effects such as providing for enhanced uptake of minerals in the large bowel.

Starch is readily isolated from wheat grain using standard methods, for example the method of Schulman et al. (1991). On an industrial scale, wet or dry milling can be used. Starch granule size is important in the starch processing industry where there is separation of the larger A granules from the smaller B granules. The starch obtained from the grain of wheat plant of the invention has a high relative amylose content.

Physical Characteristics of the Altered Starch

Gelatinisation is the heat-driven collapse (disruption) of molecular order within the starch granule in excess water, with concomitant and irreversible changes in properties such as granular swelling, crystallite melting, loss of birefringence, viscosity development and starch solubilisation. High amylose starch from ae (amylose extender) mutants of maize showed a higher gelatinisation temperature than normal maize (Fuwa et al., 1999, Krueger et al., 1987). On the other hand, starch from barley sex6 mutants that lack starch synthase Ia activity had lower gelatinisation temperatures and the enthalpy for the gelatinisation peak was reduced when compared to that from control plants (Morell et al., 2003).

In another aspect of the invention, the starch has an altered gelatinisation temperature as measured by differential scanning calorimetry. This may be either increased or reduced compared to starch from wild-type plants. The altered gelatinisation temperature may be in addition to the relatively high amylose content. The gelatinisation temperature of wild-type wheat starch is typically about 61° C. (Rahman et al, 2000) for the temperature of the first peak, defined as the onset temperature, as measured by differential scanning calorimetry.

The starch may also be characterized by its swelling rate in heated excess water compared to wild-type starch. Swelling volume is typically measured by mixing either a starch or flour with excess water and heating to elevated temperatures, typically greater than 90° C. The sample is then collected by centrifugation and the swelling volume is expressed as the mass of the sedimented material divided by the dry weight of the sample. A low swelling characteristic is useful where it is desired to increase the starch content of a food preparation, in particular a hydrated food preparation.

The starch structure of the wheat of selected forms of the present invention may also differ in that the degree of crystallinity is reduced compared to normal starch isolated from wheat. The reduced crystallinity of a starch is also thought to be associated with enhance organoleptic properties and contributes to a smoother mouth feel. Thus the starch may additionally exhibit reduced crystallinity resulting from reduced levels of activity of one or more amylopectin synthesis enzymes. Crystallinity is typically investigated by X-ray crystallography.

One measure of an altered amylopectin structure is the distribution of chain lengths, or the degree of polymerization, of the starch. The chain length distribution may be determined by using fluorophore-assisted carbohydrate electrophoresis (FACE) following isoamylase de-branching. The amylopectin of the starch of the invention may have a distribution of chain length in the range from 5 to 60 that is greater than the distribution of starch from wild-type plants upon debranching. Starch with longer chain lengths will also have a commensurate decrease in frequency of branching. Thus the starch may also have a distribution of longer amylopectin chain lengths in the amylopectin still present.

Food Characteristics

Starch is the major source of carbohydrate in the human diet, and the grain of the invention and products derived from it can be used to prepare food. The food may be consumed by man or animals, for example in livestock production or in pet-food. The grain derived from the altered wheat plant can readily be used in food processing procedures, and therefore the invention includes milled, ground, kibbled, pearled or rolled grain or products obtained from the processed or whole grain of the wheat plant referred to above, including flour. These products may be then used in various food products, for example farinaceous products such as breads, cakes, biscuits and the like, or food additives such as thickeners or binding agents, or to make drinks, noodles, pasta or quick soups. The grain or products derived from the grain of the invention are particularly desired in breakfast cereals or as extruded products. The high amylose starches of the invention can also be used to form high strength gels that are useful in the confectionery industry, or allow lower molding and curing times. They may also be used as a coating, for example to reduce oil absorption in deep-fried potato or other foods.

Dietary Fibre

Dietary fibre, in this specification, is the carbohydrate and carbohydrate digestion products that are not absorbed in the small intestine of healthy humans but enter the large bowel. This includes resistant starch, β-glucan and other soluble and insoluble carbohydrate polymers. It is intended to comprise that portion of carbohydrates that are fermentable, at least partially, in the large bowel by the resident microflora.

The starch of the invention preferably contains relatively high levels of dietary fibre, more particularly amylose. The dietary fibre content of the grain of the present invention may or may not result solely from the increased relative endospermal amylose content.

Aspects of this invention might also arise from the combination of aleurone layer and germ in combination with high levels of dietary fibre. Specifically, this may arise where higher relative levels of aleurone or germ are present in the grain. Where the wheat grain is slightly shrunken the endosperm is present in reduced amounts and the aleurone layer and the germ are present in relatively elevated amounts. Thus the wheat has a relatively high level of certain beneficial elements or vitamins in combination with elevated resistant starch, such elements include divalent cations, bioavailable $Ca^{++}$ and vitamins such as folate or antioxidants such as tocopherols or tocotrienols. One specific form of milled product might be one where the aleurone layer is included in the milled product. Particular milling process might be undertaken to enhance the amount of aleurone layer in the milled product. Thus any product derived from grain milled or otherwise processed to include aleurone layer and germ will have the additional nutritional benefits, without the requirement of adding these elements from separate sources.

Resistant Starch

Resistant starch is defined as the sum of starch and products of starch digestion not absorbed in the small intestine of healthy humans but entering into the large bowel. Thus, resistant starch excludes products digested and absorbed in the small intestine. Resistant starches include physically inaccessible starch (RS1 form), resistant granules (RS2), retrograded starches (RS3), and chemically modified starches (RS4). The altered starch structure and in particular the high amylose levels of the starch of the invention give rise to an increase in resistant starch when consumed in food. The starch may be in an RS1 form, being somewhat inaccessible to digestion. Starch-lipid association as measured by V-complex crystallinity is also likely to contribute to the level of resistant starch It will be understood that one benefit of the present invention is that it provides for products that are of particular nutritional benefit, and moreover it does so without the need to modify the starch or other constituents of the wheat grain. However it may be desired to make modifications to the starch or other constituent of the grain, and the invention encompasses such a modified constituent. Methods of modification are well known and include the extraction of the starch or other constituent by conventional methods and modification of the starches to increase the resistant form. The starch may be modified by treatment with heat and/or moisture, physically (for example ball milling), enzymatically (using for example α- or β-amylase, pullalanase or the like), chemical hydrolysis (wet or dry using liquid or gaseous reagents), oxidation, cross bonding with difunctional reagents (for example sodium trimetaphosphate, phosphorous oxychloride), or carboxymethylation.

Glycemic Index

Glycaemic Index (GI) relates to the rate of digestion of foods comprising the starch, and is a comparison of the effect of a test food with the effect of white bread or glucose on excursions in blood glucose concentration. The Glycaemic Index is a measure of the likely effect of the food concerned on post prandial serum glucose concentration and demand for insulin for blood glucose homeostasis. One important characteristic provided by foods of the invention is a reduced glycaemic index. Furthermore, the foods may have a low level of final digestion and consequently be relatively low-calorie. A low calorific product might be based on inclusion of flour produced from milled wheat grain. Such foods may have the effect of being filling, enhancing bowel health, reducing the post-prandial serum glucose and lipid concentration as well as providing for a low calorific food product.

Non-food Applications

The present invention provides modified or improved starches having elevated levels of amylose or reduced levels of amylopectin whose properties satisfy any of various industrial requirements. Starch is widely used in non-food industries, including the film, paper, textile, corrugating and adhesive industries (Young, 1984), for example as a sizing agent. Wheat starch may be used as a substrate for the production of glucose syrups or for ethanol production. The physical properties of unmodified starch limits its usefulness in some applications and often imposes a requirement for chemical modification that can be expensive or have other disadvantages. The invention provides starch for which less post-harvest modification may be required, in particular due to the reduced amylopectin content in combination with other physical properties. For example, the pasting temperature, resistance to shearing stresses, film strength and/or water resistance of starches and product made from the grain of this invention may be altered. The starch may also be used to prepare a biodegradable loose-fill packing material that can be used as a replacement for polystyrene or other packing material.

It will be understood that whilst various indications have been given as to aspects of the present invention, the invention may reside in combinations of two or more aspects of the present invention.

EXAMPLES

Example 1

Materials and Methods

Carbohydrate Determination and Analysis

Starch was isolated from wheat grain using the method of Schulman et al. (1991). Starch content was determined using the total starch analysis kit supplied by Megazyme (Bray, Co Wicklow, Republic of Ireland). The starch content is then compared to control plants. Subtraction of the starch weight from the total grain weight to give a total non-starch content of the grain determines whether the reduction in total weight is due to a reduction in starch content.

The amylose content of starch samples was determined by the calorimetric (iodometric) method of Morrison and Laignelet (1983) with slight modifications as follows. Approximately 2 mg of starch was weighed accurately (accurate to 0.1 mg) into a 2 ml screw-capped tube fitted with a rubber washer in the lid. To remove lipid, 1 ml of 85% (v/v) methanol was mixed with the starch and the tube heated in a 65° C. water bath for 1 hour with occasional vortexing. After centrifugation at 13,000 g for 5 min, the supernatant was carefully removed and the extraction steps repeated. The starch was then dried at 65° C. for 1 hour and dissolved in urea-dimethyl sulphoxide solution (UDMSO; 9 volumes of dimethyl sulphoxide to 1 volume of 6 M urea), using 1 ml of UDMSO per 2 mg of starch (weighed as above). The mixture was immediately vortexed vigorously and incubated in a 95° C. water bath for 1 hour with intermittent vortexing for complete dissolution of the starch. An aliquot of the starch-UDMSO solution (50 µl) was treated with 20 µl of $I_2$-KI reagent that contained 2 mg iodine and 20 mg potassium iodide per ml of water. The mixture was made up to 1 ml with water. The absorbance of the mixture at 650 nm was measured by transferring 200 µl to microplate and reading the absorbance using an Emax Precision Microplate Reader (Molecular Devices, USA). Standard samples containing from 0 to 100% amylose and 100% to 0% amylopectin were made from potato amylose and corn (or potato) amylopectin (Sigma) and treated as for the test samples. The amylose content (percentage amylose) was determined from the absorbance values using a regression equation derived from the absorbances for the standard samples. Analysis of the amylose/amylopectin ratio of non-debranched starches may also be carried out according to Case et al., (1998) or by an HPLC method for separating debranched starches as described by Batey and Curtin (1996).

The distribution of chain lengths in the starch may be analysed by fluorophore assisted carbohydrate electrophoresis (FACE) using a capillary electrophoresis unit according to Morell et al (1998), after debranching of the starch samples. The gelatinisation temperature profiles of starch samples may be measured in a Pyris 1 differential scanning calorimeter (Perkin. Elmer, Norwalk Conn., USA). The viscosity of starch solutions may be measured on a Rapid-Visco-Analyser (RVA, Newport Scientific Pty Ltd, Warriewood, Sydney), for example using conditions as reported by Batey et al., 1997. The parameters that may be measured include peak viscosity (the maximum hot paste viscosity), holding strength, final viscosity and pasting temperature. The swelling volume of flour or starch may be determined according to the method of Konik-Rose et al (2001). The uptake of water is measured by weighing the sample prior to and after mixing the flour or starch sample in water at defined temperatures and following collection of the gelatinized material.

β-Glucan levels may be determined using the kit supplied by Megazyme (Bray, Co Wicklow, Republic of Ireland).

Analysis of Protein Expression in Endosperm.

Specific protein expression in endosperm was analyzed by Western blot procedures. Endosperm was dissected away from all maternal tissues and samples of approximately 0.2 mg were homogenized in 600 µl of 50 mM KPi buffer (42 mM $K_2HPO_4$ and 8 mM $KH_2PO_4$), pH 7.5, containing 5 mM EDTA, 20% glycerol, 5 mM DTT and 1 mM Pefabloc. The ground samples were centrifuged for 10 min at 13,000 g and the supernatant aliquoted and frozen at −80° C. until use. For total protein estimation, a BSA standard curve was set up using 0, 20, 40, 60, 80 and 100 µl aliquots of 0.25 mg/ml BSA standard. The samples (3 µl) were made up to 100 µl with distilled water and 1 ml of Coomassie Plus Protein reagent was added to each. The absorbance was read after 5 min at 595 nm, using the zero BSA sample from the standard curve as the blank, and the protein levels in the samples determined. Samples containing 20 µg total protein from each endosperm were run on an 8% non denaturing polyacrylamide gel containing 0.34 M Tris-HCl (pH 8.8), acrylamide (8.0%), ammonium persulphate (0.06%) and TEMED (0.1%). Following electrophoresis, the proteins were transferred to a nitrocellulose membrane according to Morell et al., (1997) and immunoreacted with SBEIIa or SBEIIb specific antibodies.

Example 2

Genetic Constructs for the Alteration of Wheat SBEIIa and SBEIIb Expression

Duplex-RNA (dsRNA) constructs were made to reduce the expression of either the SBEIIa or SBEIIB genes of wheat. In such constructs, the desired nucleic acid sequence corresponding to part of the SBEIIa or SBEIIb genes occurred in both the sense and antisense orientations relative to the promoter so that the expressed RNA comprised complementary regions that were able to basepair and form a duplex or double-stranded RNA. A spacer region between the sense and antisense sequences comprised an intron sequence which, when transcribed as part of the RNA in the transformed plant, would be spliced out to form a tight "hairpin" duplex structure. The inclusion of an intron has been found to increase the efficiency of gene silencing conferred by duplex-RNA constructs (Smith et al, 2000). The desired nucleic acid was linked to a high molecular weight glutenin (HMWG) promoter sequence (promoter of the Dx5 subunit gene, Accession No. X12928, Anderson et al., 1989) and terminator sequence from the nopaline synthase gene from *Agrobacterium* (nos3'). This provided endosperm specific expression of the dsRNA sequences.

The SBEIIa duplex-RNA construct contained 1536 bp of nucleotide sequence amplified by PCR from the wheat SBEIIa gene (GenBank Accession number AF338431, see FIG. 1). This included; a 468 bp sequence that comprises the whole of exons 1 and 2 and part of exon 3 (nucleotide positions 1058 to 1336, 1664 to 1761 and 2038 to 2219 in FIG. 1), with EcoRI and KpnI restriction sites on either side (fragment 1), a 512 bp sequence consisting of part of exons 3 and 4 and the whole of intron 3 of SBEIIa (nucleotide positions 2220 to 2731 in FIG. 1) with KpnI and SacI sites on either side (fragment 2) and a 528bp fragment consisting of the complete exons 1, 2 and 3 of SBEIIa (nucleotide positions 1058 to 1336, 1664 to 1761 and 2038 to 2279 in FIG. 1) with BamHI and SacI sites on either side (fragment 3). Fragments 1, 2 and 3 were then ligated so that the sequence of fragment 3 was ligated to fragment 2 in the antisense orientation relative to fragment 1. The duplex-RNA constructs were initially generated in the vector pDVO3000 which contains the HMWG promoter sequence and nos3' terminator. The gene construct in the vector pDVO3000 was designated pDVO3-IIa and the duplex-RNA gene designated ds-SBEIIa.

The strategy for the SBEIIb duplex-RNA construct was similar. The SBEIIb construct contained a fragment of 1607bp amplified by PCR from the wheat SBEIIb gene (sequence is outlined in FIG. 2). This included a 471bp sequence that comprised the whole of exons 1 and 2 and part of exon 3 (nucleotide positions 489 to 640, 789 to 934 and 1598 to 1769 in FIG. 2), with EcoR1 and KpnI restriction sites on either side (fragment 1), a 589bp sequence consisting of part of exons 3 and 4 and the whole of intron 3 of SBEIIb (nucleotide positions 1770 to 2364 in FIG. 2) with KpnI and SacI sites on either side (fragment 2) and a 528bp fragment consisting of the complete exons 1, 2 and 3 of SBEIIb (nucleotide positions 489 to 640, 789 to 934 and 1598 to 1827 in FIG. 2) with BamHI and SacI sites on either side (fragment 3). Fragments 1, 2 and 3 were then ligated so that the sequence of fragment 3 was ligated to fragment 2 in the antisense orientation relative to fragment 1. The SBEIIb duplex-RNA gene construct in the vector pDVO3000 was designated pDVO3-IIb and the duplex-RNA gene designated ds-SBEIIb. The constructs are shown schematically in FIG. 3.

Each of the ds-RNA expression cassettes was then cut out with the restriction enzyme XhoI and inserted into the binary transformation vectors pGB53 and pBIOS340. pGB53 was created from pSB11 (Komari et al., 1996) by the introduction of the gene encoding asulam resistance (sul) driven by the rice actin promoter, leaving a unique XhoI site adjacent to the right T-DNA border for the introduction of a gene of interest. Similarly, pBIOS340 was created from pSB11 (Komari et al., 1996) by the introduction of an nptII gene encoding kanamycin and geneticin resistance, driven by the rice actin promoter, again leaving a unique XhoI site adjacent to the right border. The SBEIIa constructs in pGB53 and pBIOS340 were designated pCL51 and pCL59, respectively, and the SBEIIb constructs in pGB53 and pBIOS340 were designated pCL54 and pCL60, respectively.

Example 3

Transformation of Wheat

Genetic constructs for transformation of wheat were introduced by electroporation into the disarmed *Agrobacterium tumefaciens* strain LBA4404 carrying the vir plasmid pAL4404 and pSB1, with subsequent selection on media with spectinomycin. Transformed *Agrobacterium* strains were incubated on solidified YEP media at 27° C. for 2 days. Bacteria were then collected and re-suspended in TSIM1 (MS media with 100 mg/l myo-inositol, 10 g/l glucose, 50 mg/l MES buffer pH5.5) containing 400 mM acetosyringone to an optical density of 2.4 at 650 nm for wheat inoculation. Wheat plants (variety NB 1, a Spring wheat variety obtained from Nickerson Seeds Ltd, Rothwell, Lincs.) were grown in a glasshouse at 22/15° C. day/night temperature with supplemented light to give a 16 hour day. Tillers were harvested approximately 14 days post-anthesis (embryos approximately 1 mm in length) to include 50 cm tiller stem. All leaves were then removed from the tillers except the flag leaf, which was cleaned to remove contaminating fungal spores. The glumes of each spikelet and the lemma from the first two florets were then carefully removed to expose the immature seed. Generally, only these two seed in each spikelet were uncovered. This procedure was carried out along the entire length of the inflorescence. The ears were then sprayed with 70% IMS as a brief surface sterilization.

*Agrobacterium* suspensions (1 µl) were inoculated using a 10 µl Hamilton syringe into the immature seed approximately at the position of the scutellum:endosperm interface so that all exposed seed were inoculated. The tillers were then placed in water, covered with a translucent plastic bag to prevent seed dehydration, and placed in a lit incubator for 3 days at 23° C., 16 hr day, 45 µEm$^{-2}$s$^{-1}$PAR. After 3 days of co-cultivation, the inoculated immature seed were removed and surface sterilized with 70% ethanol (30 sec), then 20% bleach (Domestos, 20 min), followed by thorough washing in sterile distilled water. Immature embryos were aseptically isolated and placed on W3 media (MS supplemented with 20 g/l sucrose and 2 mg/l 2,4-D and solidified with 6 g/l Type I agarose, Sigma) with the addition of 150 mg/l Timentin (W3T) and with the scutellum uppermost (20 embryos per plate). Cultures were placed at 25° C. in the light (16 hour day, 80 µEm$^{-2}$s$^{-1}$PAR). The development of the embryonic axis on the embryos was assessed about 5 days after isolation and the axis was removed where necessary to improve callus production. The embryos were maintained on W3T for 4 weeks, with a transfer to fresh media at 2 weeks post-isolation and assessed for embryogenic capacity.

After 4 weeks growth, callus derived from the inoculated embryos was very similar to control callus obtained from uninoculated embryos plated on W3T medium. Presence of the bacteria did not appear to have substantially reduced the embryogenic capacity of the callus derived from the inoculated embryos. Embryogenic calli were transferred to W3 media with 2 mg/l Asulam (where pGB53 derivatives were used) or geneticin at 25 mg/l (pBIOS340 derivatives) and 150 mg/l Timentin (W32AT). Calli were maintained on this media for a further 2 weeks and then each callus was divided into 2 mm-sized pieces and re-plated onto W32AT. Control embryos derived from inoculations with the LBA4404 without binary vector constructs did not produce transformed callus on selection media.

After a further 2 weeks culture, all tissue was assessed for development of embryogenic callus: any callus showing signs of continued development after 4 weeks on selection was transferred to regeneration media (RMT-MS with 40 g/l maltose and 150 mg/l Timentin, pH 5.8, solidified with 6 g/l agarose, Sigma type 1). Shoots were regenerated within 4 weeks on this media and then transferred to MS30 with 150 mg/l Timentin for shoot elongation and rooting. Juvenile plants were then transferred to soil mixture and kept on a misting bench for two weeks and finally transferred to a glasshouse.

A total of 3217 embryos using pCL54 or pCL60 (ds-SBEIIb) and 2010 embryos using pCL51 or pCL59 (ds-SBEIIa) were treated by this method and 61 plants were regenerated from calli for the IIb transformation and 31 plants regenerated from calli for the IIa transformation. Survival on selection medium suggested that they were successfully transformed with the gene construct. A large majority, but not all, of the plants that were transformed with the selectable marker gene would be expected to integrate the SBEIIa or SBEIIb inhibitory gene; these could readily be distinguished as described in the following examples.

The recovery of multiple, stable integration events with good regeneration potential from the experiments indicated that the seed inoculation transformation method used here was as efficient as other reported methods for wheat. Alternative *Agrobacterium* strains such as strain AGLI or selectable markers such as genes encoding hygromycin resistance can also be used in the method.

Example 4

Analysis of Wheat Transformants

Transformation was determined by one or more of the following methods: PCR analysis for one or more of the transgenes. PCR analysis was performed on genomic DNA extracted from 1-2 $cm^2$ of fresh leaf material using the miniprep method described by Stacey and Isaac (1994). PCR reactions were performed, for example, using the primers SBEIIa-For: 5'-CCCGCTGCTTTCGCTCATTTTG-3' [SEQ ID No. 9] and SBEIIa-Rev: 5'-GACTACCGGAGCTC-CCACCTTC-3' [SEQ ID No. 10] designed to amplify a fragment (462bp) from the SBEIIa gene, or SBEIIb-DupFor 5'-AGATGTGAATGGCTGCTTGCTG-3' [SEQ ID No. 11] and SBEIIb-DupRev 5'-CAGGTCGACCATATGG-GAGAGC-3' [SEQ ID No. 12] for SBEIIb (505bp). Reaction conditions were as follows: "hot start" (94° C., 3 min) followed by 30 cycles of denaturation (95° C., 30 sec), annealing (55° C., 30 sec), extension (73° C., 2 min) followed by 1 cycle at 73° C. (5 min).

Southern blot hybridization analysis is performed on DNA from a larger scale (9 ml) extraction from lyophilized ground tissue (Stacey and Isaac, 1994). DNA samples are adjusted to 0.2 mg/ml and digested with restriction enzymes such as HindIII, EcoRI and KpnI. Restriction enzyme digestion, gel electrophoresis and vacuum blotting are carried out as described by Stacey and Isaac (1994). Digoxygenin-labelled probes including the intron 3 region of the ds-SBEII constructs are produced by PCR according to the method of McCreery and Helentjaris (1994). Hybridization of the probes to the Southern blot and detection by chemiluminescence are performed according to the method of McCreery and Helentjaris (1994).

The results of the PCR analyses are summarized in Table 2. Plants that were positive for the transgenes as demonstrated by PCR included 27 independent transformation events for ds-SBEIIa and 61 independent events for ds-SBEIIb.

TABLE 2

Transformation of wheat with SBEIIa and SBEIIb RNA duplex constructs.

| Experiment No. | No. of embryos inoculated | No. of lines regenerated | PCR positive lines |
|---|---|---|---|
| ds-SBEIIa construct | | | |
| 44 | 242 | 1 | 1 |
| 50 | 169 | 3 | 3 |
| 52 | 158 | 3 | 3 |
| 58 | 163 | 2 | 2 |
| 61 | 195 | 1 | 1 |
| 72 | 185 | 1 | 0 |
| 83 | 241 | 1 | 1 |
| 84 | 242 | 1 | 1 |
| 85 | 153 | 5 | 5 |
| 109 | 262 | 13 | 10 |
| Total | 2010 | 31 | 27 |
| ds-SBEIIb construct | | | |
| 48 | 291 | 1 | 1 |
| 51 | 166 | 1 | 0 |
| 53 | 194 | 1 | 0 |
| 55 | 261 | 1 | 1 |
| 59 | 253 | 1 | 0 |
| 60 | 175 | 4 | 2 |
| 62 | 199 | 1 | 0 |
| 70 | 152 | 1 | 0 |
| 73 | 238 | 2 | 2 |
| 75 | 151 | 2 | 2 |
| 76 | 150 | 1 | 0 |
| 77 | 150 | 2 | 2 |
| 81 | 134 | 1 | 1 |
| 87 | 230 | 5 | 3 |
| 92 | 233 | 8 | 5 |
| 110 | 240 | 29 | 16 |
| Total | 3217 | 61 | 35 |

Example 5

Analysis of Grain from Plants Transformed with Duplex-RNA Constructs

Starch Granule Morphology

The morphology of starch granules from mature T1 seed obtained from the T0 transformed wheat plants was observed by light microscopy. Ten individual grains from each of 25 T0 plants independently transformed with ds-SBEIIa and 12 plants independently transformed with ds-SBEIIb were analysed. Each endosperm was gently crushed to release the starch granules, which were dispersed in water and visualized under a light microscope. Of the 25 ds-SBEIIa lines analysed, 12 had grains with distorted granules (for example, see FIG. 4) although the visual observation revealed varying levels of distortion in different seeds. In contrast, none of the 12 ds-SBEIIb lines showed significant starch granule distortion in the endosperm when observed under light microscopy, The results are summarized in Tables 3 and 4.

TABLE 3

Starch granule morphology of T1 seeds of ds-SBEIIa transgenic wheat lines.

| Slide No. | Line No | Granule Morphology* |
|---|---|---|
| 1 | 44.1a | + |
| 2 | 50.1b | − |
| 3 | 50.2b | + |
| 4 | 50.3x | − |
| 5 | 52.1a | + |
| 6 | 52.2a | + |
| 7 | 52.3a | +/− |
| 8 | 58.1a | − |
| 9 | 58.2a | − |
| 10 | 61.2a | − |
| 11 | 83.1b | + |
| 12 | 84.1a | +/− |
| 13 | 85.1a | +/− |
| 14 | 85.2c | − |
| 15 | 85.3a | − |
| 16 | 85.4b | + |
| 17 | 85.5a | − |
| 18 | 109.1a | − |
| 19 | 109.2c | + |
| 20 | 109.3b | + |
| 21 | 109.4e | − |
| 22 | 109.7b | − |
| 23 | 109.8c | − |
| 24 | 109.10a | + |
| 25 | 109.11x | + |

*Starch granule morphology of 10 seeds from each line was observed.
Morphology is indicated as + if all the ten seeds had normal granule morphology, − if there were seeds which were severely distorted, and +/− for some abnormality, i.e. at least some seeds with some distortion but none with severe distortion.

TABLE 4

Starch granule morphology of T1 seeds of ds-SBEIIb transgenic wheat lines.

| Slide No | Lines | Granule Morphology |
|---|---|---|
| 1 | 48.1a | + |
| 2 | 55.1a | + |
| 3 | 60.1a | + |
| 4 | 60.4a | + |
| 5 | 73.1f | + |
| 6 | 75.1c | + |
| 7 | 75.3x | + |
| 8 | 77.1c | + |
| 9 | 77.2c | + |
| 26 | 110.16b | + |
| 27 | 110.17b | + |
| 28 | 110.18a | + |

+ indicates that all the ten seeds from each line had normal starch granule morphology Observing the starch granules under polarized light revealed that there was a significant reduction in birefringence for distorted granules (FIG. 5) for the ds-SBEIIa grain. Loss of birefringence was observed for 94% of the granules in seeds from the line 50.1b, correlating with their distorted phenotype, while normal granules from another seed of the same line showed full birefringence (Table 5). The seed with normal granules is presumed to be a segregant lacking the transgene and therefore phenotypically normal.

TABLE 5

Birefringence of starch granules from T1 seeds of the ds-SBEIIa transgenic wheat line 50.1b

| Seed from the line 50.1b | Microscopic field | No. of granules showing no BF | No. of granules showing partial BF | No. of granules showing full BF |
|---|---|---|---|---|
| Seed with distorted granules | 1 | 55 | 2 | 1 |
| | 2 | 73 | 1 | 0 |
| | 3 | 44 | 1 | 0 |
| | 4 | 92 | 3 | 2 |
| | 5 | 46 | 2 | 7 |
| | 6 | 46 | 2 | 3 |
| Total | | 356 (93.7%) | 11 (2.9%) | 13 (3.4%) |
| Seed with normal granules | 1 | 1 | 3 | 110 |
| | 2 | 1 | 1 | 38 |
| | 3 | 3 | 4 | 90 |
| | 4 | 0 | 3 | 61 |
| | 5 | 3 | 3 | 59 |
| | 6 | 1 | 0 | 30 |
| Total | | 9 (2.2%) | 14 (3.4%) | 388 (94.4%) |

Light microscopy results are confirmed by scanning electron microscopy (SEM) of the starch granules. To do this, purified starch is sputtered with gold and scanned at 15 kV at room temperature.

Grain Weight

Individual grains from ds-BEIIa transformed plants, grown under equivalent conditions in the greenhouse, were weighed (Table 6). Grains having severely distorted granules 50.1b 58.2a, 61.2a and 109 were not significantly reduced in average weight compared to grains of wild-type plants grown under the same conditions. Therefore, starch production did not appear to be substantially reduced even in the seeds with highly distorted starch granules. This data also suggests that the yield of field-grown wheat with reduced SBEIIa activity in the endosperm is about normal.

TABLE 6

Grain weight of T1 seeds from the ds-SBEIIa transgenic wheat lines

| Transgenic Line | Seed No | Seed weight (mg) | Starch granule morphology* |
|---|---|---|---|
| 50.1b | 1 | 16.9 | + |
| | 2 | 49.8 | + |
| | 3 | 46.9 | − |
| | 4 | 50.0 | − |
| | 5 | 45.4 | − |
| | 6 | 42.6 | − |
| | 7 | 39.9 | +/− |
| | 8 | 41.0 | + |
| | 9 | 39.5 | − |
| | 10 | 37.0 | +/− |
| 58.2a | 1 | 44.0 | − |
| | 2 | 37.4 | + |
| | 3 | 48.8 | − |
| | 4 | 43.2 | + |
| | 5 | 46.2 | − |
| | 6 | 42.1 | + |
| | 7 | 43.5 | +/− |
| | 8 | 45.7 | − |
| | 9 | 38.8 | − |
| | 10 | 38.1 | +/− |

TABLE 6-continued

Grain weight of T1 seeds from the ds-SBEIIa transgenic wheat lines

| Transgenic Line | Seed No | Seed weight (mg) | Starch granule morphology* |
|---|---|---|---|
| 61.2a | 1 | 50.7 | + |
|  | 2 | 49.0 | +/− |
|  | 3 | 49.8 | − |
|  | 4 | 47.0 | − |
|  | 5 | 48.6 | − |
|  | 6 | 46.2 | − |
|  | 7 | 42.2 | + |
|  | 8 | 50.4 | − |
|  | 9 | 39.7 | − |
|  | 10 | 46.3 | − |
| 109.7b | 1 | 40.1 | − |
|  | 2 | 34.6 | − |
|  | 3 | 43.7 | − |
|  | 4 | 38.8 | − |
|  | 5 | 33.8 | +/− |
|  | 6 | 31.1 | +/− |
|  | 7 | 35.9 | + |
|  | 8 | 44.3 | +/− |
|  | 9 | 37.7 | − |
|  | 10 | 41.4 | − |

+ normal starch granules,
− severely distorted granules,
+/− mild distortion of granules Analysis of SBEIIa and SBEIIb Proteins in T2 Transgenic Wheat Endosperm.

Seed (T2) from 13 ds-SBEIIa transformed T1 plants, representing 5 independently transformed lines, and from 9 ds-SBEIIa transformed plants, representing 3 independently transformed lines, were analysed for SBEIIa and SBEIIb protein expression in endosperm by non denaturing PAGE and Western blotting. The ds-SBEIIa plants were all from lines having abnormal starch granule morphology, while the ds-SBEIIb lines all had normal granule morphology, as described above. The antibody used for detection of SBEIIa was 3KLH, from rabbits, which had been raised against the synthetic peptide having the amino acid sequence AASPGKVLVPDESDDLGC [SEQ ID No. 13], corresponding to the sequence from the N-terminus of mature SBEIIa, and was diluted 1:5000 for use. The antibody used for detection of SBEIIb was R6, raised against the synthetic peptide having the amino acid sequence AGGPSGEVMIGC [SEQ ID No. 14], corresponding to the deduced sequence from the N-terminus of mature SBEIIb and diluted 1:6000 before use. The secondary antibody used was GAR-Horseradish Peroxidase conjugate (1:3000 dilution). Immunoreactive bands were revealed using an Amersham ECL-detection system.

Endosperms from each of seven developing grains (15 days post anthesis) from each of the 22 T1 plants were analysed as it was expected that some of the plants would be heterozygous for the transgene. Twelve of the 13 ds-SBEIIa plants produced T2 progeny showing reduced levels of SBEIIa protein in the endosperm. All seven seeds from one line (50.3×0.9) appeared to lack SBEIIa entirely, while all seven seeds from four other plants showed obviously reduced expression of SBEIIa (Table 7). These could represent lines that are homozygous for the transgene. Seven lines were segregating for the absence of SBEIIa or reduced levels of SBEIIa, or in some cases no apparent reduction of the protein, and these lines probably represent heterozygotes for the transgene. The thirteenth line (50.3×0.6) was homozygous for wild type expression (Table 7).

TABLE 7

Western blot analysis of endosperm proteins from T2 ds-SBEIIa transgenic wheat lines

| Transgenic line | Gene targeted | T1 granule morphology | Segregation of SBEII protein band in T2 grains |
|---|---|---|---|
| 50.3x.6 | SBEIIa | + | Uniform for wild type expression (+) |
| 58.1a.3 | " | − | Segregating for +/− and − |
| 58.1a.7 | " | − | Segregating for +, +/− and − |
| 58.1a.9 | " | − | Segregating for +, +/− and − |
| 50.1b.3 | " | − | Uniform for +/− |
| 50.1b.4 | " | − | Segregating for +/− and − |
| 50.1b.5 | " | − | Uniform for +/− |
| 50.1b.9 | " | − | Segregating for + and +/− |
| 50.3x.9 | " | − | Uniform for − |
| 61.2a.8 | " | − | Uniform for +/− |
| 61.2a.9 | " | − | Segregating for +/− and − |
| 61.2a.10 | " | − | Uniform for +/− |
| 85.2c.2 | " | − | Segregating for +/− and − |
| 110.16b.14 | SBEIIb | + | Uniform for wild type expression (+) |
| 110.16b.2 | " | + | Uniform for − |
| 110.16b.17 | " | + | Uniform for + |
| 110.16b.5 | " | + | Uniform for − |
| 110.16b.19 | " | + | Uniform for − |
| 110.17b.3 | " | + | Segregating for +/− and − |
| 110.17b.6 | " | + | Segregating for + and +/− |
| 110.18a.9 | " | + | Segregating for +/− and − |
| 110.18a.17 | " | + | Segregating for +, +/− and − |

Of the nine ds-SBEIIb transgenic lines tested, three (110.16b.2, 110.16b.5 and 110.16b.19) uniformly showed no SBEIIb expression in each of seven progeny seeds, while two were uniform for wild type expression and the remaining four were segregating for no expression, reduced expression or wild-type (Table 7). Embryos from the seeds may be grown (embryo rescue) to produce T2 plants and T3 seed which are screened by PCR and protein expression analysis to confirm the genetic status of the T2 seed with respect to the transgene.

These data indicate that the duplex-RNA constructs are effective in reducing the expression of the SBEIIa and SBEIIb genes in endosperm of wheat. The data also indicate that reduction of SBEIIb expression alone did not substantially alter starch granule morphology.

The expression of the SBEIIb gene in transgenic seeds containing the ds-SBEIIa transgene and lacking SBEIIa protein, and the expression of the SBEIIa gene in seeds containing the ds-SBEIIb were also analyzed by the Western blot method. Unexpectedly, transgenic seeds comprising ds-SBEIIa were much reduced for SBEIIb. However, the converse effect was not observed in seeds transgenic for ds-SBEIIb. The SBEIIa expression was unaltered in the seeds in which SBEIIb was completely silenced by ds-SBEIIb. It is possible that expression of SBEIIb was suppressed by the ds-SBEIIa construct due to sequence homology between the genes in the region used for the duplex construct, it is also possible that the activity of SBEIIb was reduced by the ds-SBEIIa transgene by some other mechanism.

The expression levels of the SBEIIa and SBEIIb genes can also be specifically determined at the mRNA levels through standard techniques such as Northern hybridisation or RT-PCR methods, for example by using probes from non conserved regions or primer pairs which hybridize to unique sites in one of the genes but not the other, for example in the 3' untranslated regions. Such regions or sites can readily be identified by comparison of the two gene sequences.

Example 6

Starch Analysis of Transformed Wheat

Amylose and Amylopectin Levels in Transgenic Wheat Grain.

The amylose content of starches from six pooled TI seed samples was determined as described in Example 1. The pooled seed samples were obtained from the transgenic wheat lines as follows:

Pool 1—seed that had distorted starch granules from the ds-SBEIIa transgenic line 85.2c Pool 2—seed that had normal granules from the ds-SBEIIa transgenic line 85.1a Pool 3—seed that had normal granules from the ds-SBEIIb transgenic line 110.18a Pool 4—seed that had distorted granules from the ds-SBEIIa transgenic lines 58.1a, 58.2a and 61.2a, pooled together Pool 5—seed that had normal granules from the ds-SBEIIa transgenic line 83.1b Pool 6—seed that had normal granules from the ds-SBEIIb transgenic line 75.3x.

Each analysis was done using four replicates of the starch samples. The regression equation used to convert the absorbance to amylose content for these analyses was Y=57.548x−8.793, where Y was the amylose content (%) and x was the absorbance.

The results are given in Table 8. The presence of distorted starch granules was clearly associated with increased amylose contents. Starch from grains with distorted granules from the ds-SBEIIa transgenic lines (pools 1 and 4) had an amylose content of greater than 50% while the other starch pools, derived from grain with normal starch granules, had amylose contents in the range 21-26%. This included starch from line IIb 110.18a which had reduced expression of SBEIIb (Table 8), which suggests that inactivation of SBEIIb alone in wheat does not substantially increase amylose levels in grain starch.

TABLE 8

Amylose content estimated by iodometric method of the transgenic wheat lines

| Starch sample | Transgenic line | Amylose content (%) | | | |
|---|---|---|---|---|---|
| | | Replication 1 | Replication 2 | Replication 3 | Mean |
| Pool 1 | 85.2c | 65.7 | 54.2 | 53.2 | 57.7 |
| Pool 2 | 85.1a | 23.7 | 22.5 | 26.7 | 24.3 |
| Pool 3 | 110.18a | 22.3 | 21.0 | 21.5 | 21.6 |
| Pool 4 | 58.1, 58.2a, 61.2a | 53.9 | 52.8 | 58.5 | 55.1 |
| Pool 5 | 83.1b | 26.5 | 25.3 | 24.8 | 25.6 |
| Pool 6 | 75.3x | 24.3 | 20.6 | 19.5 | 21.5 |

A second set of analyses was done by the iodometric method using a sample from Pool 4 and starch from wheat that is defective in SSII (Yamamori et al. 2000) and from barley line M292 which is mutant in SSIIa. The amylose content determined for starch from Pool 4 wheat seeds (ds-SBEIIa transgenic lines) was considerably higher than that of starch from the SSII mutants of wheat and barley.

This implies that the amylopectin content in the starch of these grains is considerably reduced, from about 75% in wild-type to less than 50% or even less than 20%.

Lines containing both ds-SBEIIa and ds-SBEIIb transgenes are generated by crossing the transgenic plants described above. Amylose contents in the grain starch of such progeny are elevated above that for starch from plants containing only ds-SBEIIa, for example to 75 or 80%, showing that inhibition of SBEIIb in addition to SBEIIa further elevates amylose levels.

Example 7

Comparison of SBEIIa from A, B and D Genomes

Construction of Wheat cDNA and Genomic Libraries.

Wheat endosperm cDNA and genomic libraries were made by standard methods in phage vectors (Sambrook et al, 1989). Two cDNA libraries were made, one from RNA from the cultivar Rosella (Rahman et al., 1999) and the other from cultivar Wyuna (Rahman et al. 2001). The Rosella library was in the vector ZAPII and used EcoRI and NotI primers while the Wyuna library was in the ZipLox vector (Life Technology) according to the protocols supplied with the reagents. The titres of the libraries were $2 \times 10^6$ pfu tested with Y1090 (ZL) strain of *E. coli*. A genomic library was made from DNA from *A. tauschii* variety 10097. The DNA was digested with Sau3A and ligated to partially filled lambdaGEM12 vector (Promega). Cloned fragments could be released with SacI or XhoI digestion. Genomic libraries of *T. aestivum* DNA were as described by Turner et al. (1999).

Isolation of SBEIIa cDNA Sequences.

Using a wheat SBEI gene sequence probe at low stringency (Rahman et al. 2001), cDNAs were isolated from the library prepared from the cultivar Rosella. The longest clone obtained, designated sbe9 was sequenced and seen to encode a SBEIIa type of sequence (Genbank AF338432.1). Subsequently, three clones were isolated from the endosperm cDNA library prepared from the cultivar Wyuna (Rahman et al. 2001) using a probe corresponding to positions 536 to 890 of sbe9. Conditions for library screening were hybridisation at 25% formamide, 5×SSC, 0.1% SDS, 10× Denhardts solution, 100 µg/ml salmon sperm DNA at 42° C. for 16 hr, followed by washing with 2×SSC, 0.1% SDS at 65° C. for 3×1 hr (medium stringency). Three different sequences were obtained by sequencing the clones and these are represented below by sr995 and sr997 (FIG. 6).

Investigation of these cDNA sequences indicated that different sequences were expressed in the wheat endosperm and these are likely to correspond to SBEIIa transcripts from the different wheat genomes. A PILEUP comparison of the sequences with other known wheat SBEIIa cDNA sequences showed that sr995 and sr996 sequences clustered with the mRNA sequence derived from the D-genome sequence wSBE-D1 (sr854) (FIG. 7), suggesting that sr995 and sr996 represent transcripts from the D genome SBEIIa. Sr997 clustered with the Y11282 sequence (Nair et al., 1997) indicating that they are probably from the same genome, either the A or B genome. The previously described sbe9 (AF338432.1) is probably from the same genome as Y11282 but represents an alternative splicing event, consistent with one exon near the 5' end being spliced out.

Distinguishing SBEIIa Genes from the A, B and D Genomes of Wheat *T. aestivum*.

Differences in the gene or RNA transcript sequences may used as a basis of designing A, B and D genome specific primers for mutational screening either at the gene level or at the RNA level. For example, FIG. 6 compares SBEIIa nucleotide sequences from cDNAs including Genbank accession Y11282, and partial sequences of cDNAs sbe9 (AF338432.1), sr997 and sr995. Genomic sequences are available for SBEIIa genes from *T. aestivum*, for example see Table 1. Genomic sequences have been ascribed to the A, B and D genomes. Comparison shows polymorphisms, any of which can be used to distinguish the sequences by molecular means.

A forward primer based on a region of exon 5 (5'-ATCACT-TACCGAGAATGGG-3') [SEQ ID No. 15] and a reverse primer based on a sequence in exon 6 (5'-CTGCATTTGGAT-TCCAATTG-3') [SEQ ID No. 16] have been used to distinguish between products from the A, B and D genomes. Such primers may be used in PCR reactions to screen for what varieties or accessions that are mutant in one or more of the SBEIIa genes from the A, B or D genomes (see below).

PCR based markers have also been developed to distinguish the SBEIIb genes from the A, B and D genomes of wheat. For example, PCR reactions with the primer pair ARA19F (5'-CACCCATTGTAATTGGGTACACTG-3') [SEQ ID No. 17] and ARA15R (5'-TCCATGCCTCCT-TCGTGTTCATCA-3') [SEQ ID No. 18] followed by digestion of the amplification products with the restriction enzyme RsaI could distinguish the SBEIIb genes from the three genomes.

The differences in cDNA sequence are reflected in the deduced protein sequences. For example, the deduced full-length amino acid sequences for the D genome (sr854) and A or B genome (Y11282) polypeptides are compared in FIG. 8. Significant differences are evident at regions 688-698 and 735-6 which could be used for producing genome-specific antibodies to the SBEIIa proteins, in order to screen for wheat varieties lacking one or more genome-specific activities. Other differences occur in the transit peptide sequences which correspond to amino acid positions 1-54 of FIG. 8.

Example 8

Identification of Wheat Varieties Mutant in One or More SBEII Genes

Identification of SBEIIb Null Mutations in B and D Genomes

Figure 9:
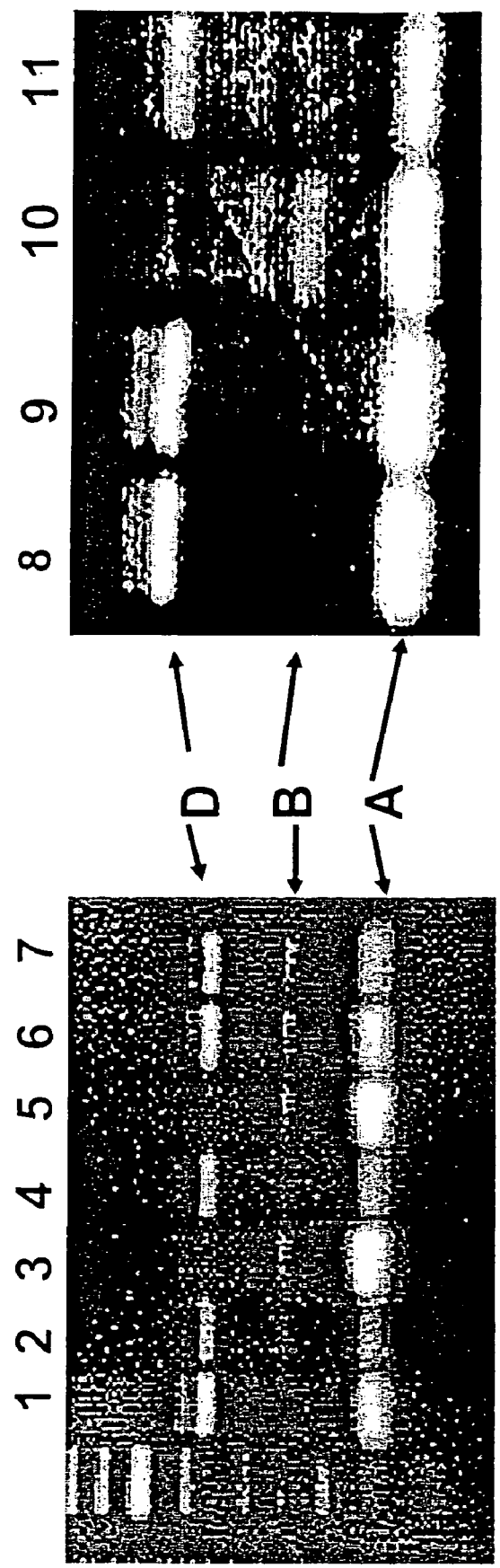
FIG. 9. PCR amplification of an intron 3 region of SBEIIb gene from various wheat accessions (Lanes 1 to 11) using the primers ARA19F and ARA23R followed by digestion with Rsa1. Bands corresponding to the A, B and D genomes are arrowed. Lane 3 (Aus17340) and Lane 5 (Aus10103) lack the D genome specific marker; while lane 8 (Aus12509) and lane 9 (Aus12565) lack the B genome marker.

A total of 1500 wheat accessions including 300 Australian wheat varieties, 900 wheat accessions from the Australian Winter Cereal Collection (AWCC, Tamworth, NSW Australia) and 300 wheat land races were screened by PCR amplification of an SBEIIb marker, corresponding to a polymorphic intron 3 region, using the primers ARA19F (see above) and ARA23R (5'-CTGCGCATAAATCCAAACTTCTCG-3') [SEQ ID No. 19]. PCR amplification used conditions as described above. Amplification products were digested with the restriction enzyme RsaI and electrophoresed on polyacrylamide gels. Three lines (Aus12745, Aus17340 and Aus10103) lacked the D genome marker and two lines (Aus12509 and Aus12565) lacked the B genome marker (FIG. 9). These lines represent presumed null mutants in the SBEIIb genes for the B or the D genomes.

Figure 10:
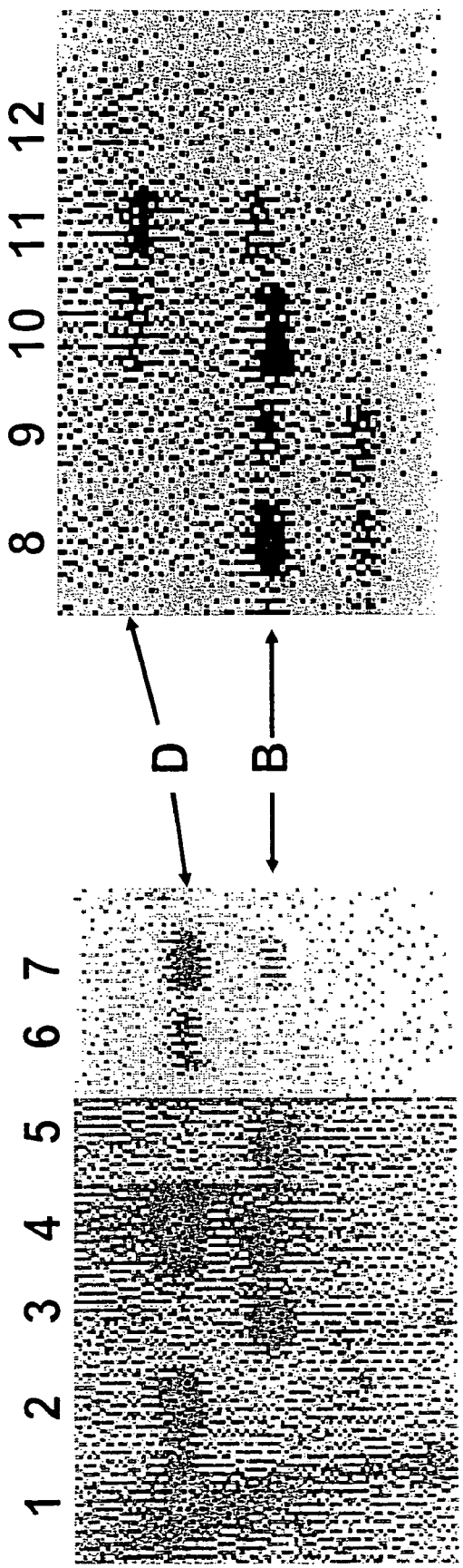
FIG. 10. Southern hybridization of HindIII digested DNA from wheat accessions using a probe from the intron 3 region of SBEIIb. Lanes correspond to: 1) Aus12565, 2) Aus12509, 3) Aus10103, 4) CSDT2DL-4, 5) Aus12530 (durum wheat), 6) CSDT2BL-9, 7) Aus6323 8) CSDT2DS, 9) Aus17340, 10) Aus12745, 11) CSDT2DL-4 12) *Aegilops tauschii*.

Southern blot hybridization analysis was carried out on DNA from the null mutant lines to confirm the PCR results. HindIII digested DNA, prepared from the plants by standard methods, was electrophoresed on 1% agarose gels and blotted on to Hybond N+ nylon membrane (Amersham). Radio-labelled probes were generated from the intron 3 region of SBEIIb (positions 2019 to 2391, see FIG. 2) gene using the Megaprime DNA labelling system (Amersham Pharmacia Biotech UK Ltd) and used for hybridization under stringent conditions. Aus17340 and Aus10103 were missing the ~4.8 kB band from the D genome and Aus12509 and Aus12565 were missing the ~3.4 kB band from the B genome (FIG. 10). These lines are therefore confirmed to be null mutants for the D or B genome SBEIIb genes, respectively.

Generation of B+D Double Null Mutants.

The following crosses were carried out:

Aus17340a×Aus 12509

Aus17340b×Aus12509

Aus17340a×Aus 12565

Aus17340b×Aus12565

Aus12745×Aus12509

Aus12745×Aus12565

Figure 11:
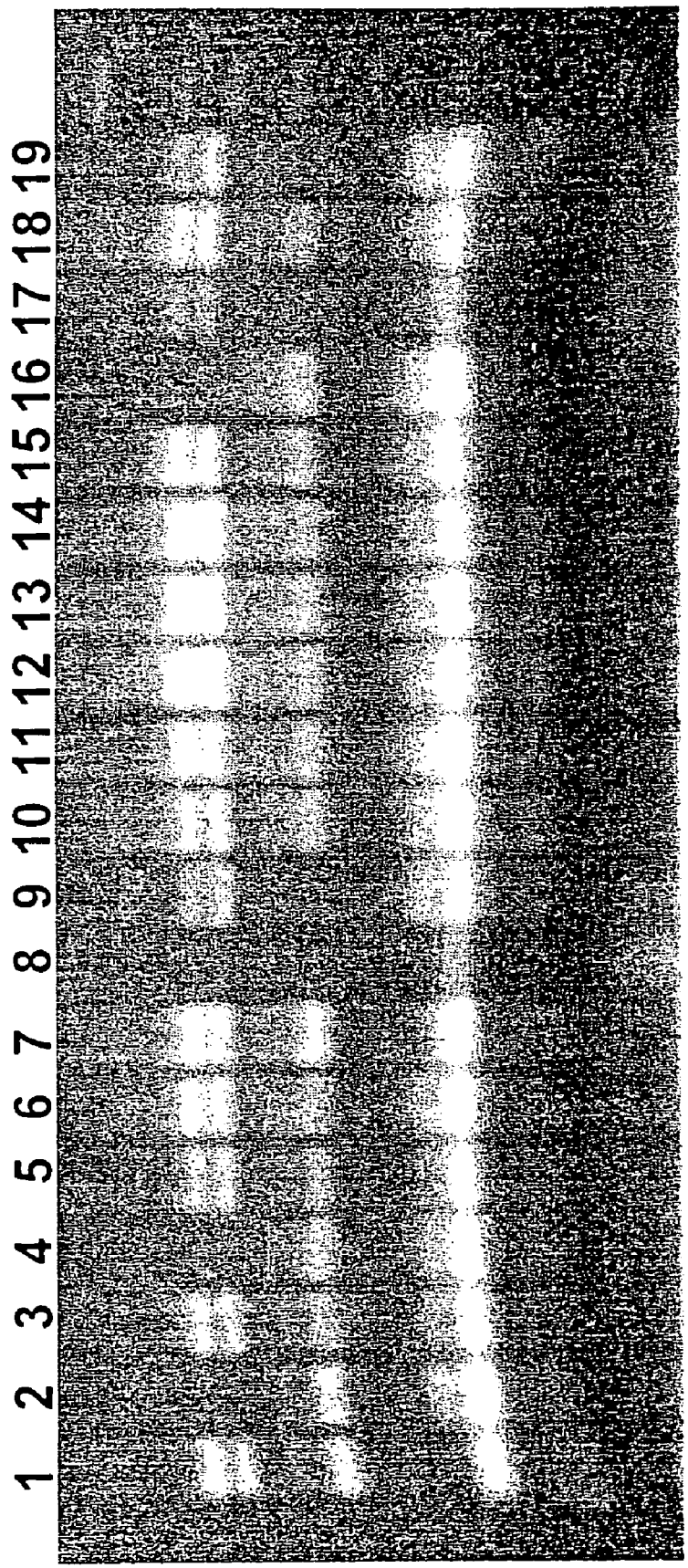
FIG. 11. Screening of F2 population of the cross Aus17340a X Aus12509 by PCR amplification of the intron 3 region of SBEIIb using the primers AR219cF and AR2b23cR followed by RsaI digestion. Lane 8 lacks both the B and D genome markers, so line BD54 represents a BD double null line.

Aus17340a and Aus17340b are two different biotypes of the same Aus17340 cultivar; both were confirmed to be null for the D genome SBEIIb gene marker. The F1 plants were selfed and the F2 progeny screened by the PCR method for plants that were mutant in both the B and D genome SBEIIb genes (double null mutants). Segregation of the SBEIIb mutations was observed by PCR amplification using the primer pairs AR2b19cF (5'-CTATGCCAATTGAACAACAATGC-3') [SEQ ID No. 20] and AR2b23cR (5'-CGTGTTCAT-CAATGTCTGAACG-3') [SEQ ID No. 21] (which amplifies the same region as ARA19F/ARA 23R) followed by digestion with the restriction enzyme Rsa 1. A typical segregation pattern is shown in FIG. 11. Chi square analysis revealed that the segregation pattern of the crosses Aus17340a×Aus12509 and Aus17340a×Aus12565 fitted in the expected ratio of 9:3:3:1 (Table 9). The segregation was highly distorted in the other crosses.

TABLE 9

Chi square analysis of F2 population of crosses between SBEIIb null mutants in the B and D subgenomes

| Cross/ Phenotypes | 17340a × 12509 | 17340b × 12509 | 1734a × 12565 | 17340 × 12565 | 12745 × 12509 | 12745 × 12565 |
|---|---|---|---|---|---|---|
| Normal | 85 | 63 | 56 | 72 | 95 | 21 |
| B null | 38 | 39 | 25 | 35 | 11 | 2 |
| D null | 23 | 29 | 11 | 11 | 57 | 16 |
| BD null | 6 | 10 | 4 | 6 | 3 | 0 |
| Total | 152 | 141 | 96 | 124 | 166 | 39 |
| $\chi^2_{(9:3:3:1)}$ | 5.52 | 9.73 | 6.19 | 12.91 | 39.79 | 16.66 |

Tabled value of $\chi^2_{(9:3:3:1)}$ (0.05), df 3 = 7.81

Albino plants were detected in all of the crosses irrespective of the parental lines, indicating that a mutant chlorophyll-related gene was also segregating in the populations. Of 24 albino plants analysed, 23 were B+D double null mutants and one appeared to be wild-type. Five normal looking green plants with B+D double null mutations were identified from 718 lines tested. Three of them were from the cross Aus17340b×Aus12509 (BD219, BD303, BD341), one from the cross Aus17340a×Aus12509 (BD54) and one from Aus17340b×Aus12565 (BD636). The results revealed that the mutations in the B and D genome SBEIIb genes were closely linked to a mutation in a chlorophyll-related gene which was giving the albino phenotype when two mutated loci came together. However, recombination events between the SBEIIb gene and the chlorophyll-related gene were identified, giving rise to normal B+D double null mutant lines, although at a very low frequency. This indicates that the two genes are closely linked but can be separated.

Example 9

SBEIIa and SBEIIb are Linked in Wheat

Isolation of BAC Clones

Figure 12:
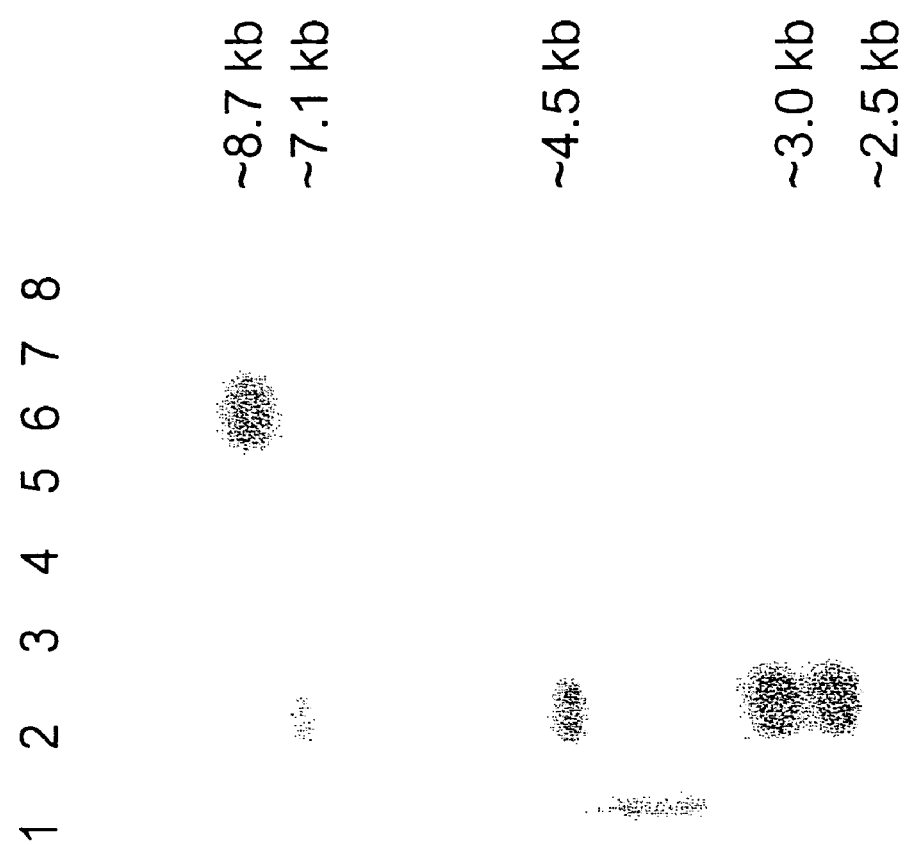
FIG. 12. Southern hybridization of HindIII (lanes 1 to 4) and EcoR1 (lane 5 to 8) digested BAC clones using a probe from the intron 3 region of SBEIIb. Lanes correspond to: 1) BAC 4, 2) BAC 5, 3) BAC 9, 4) BAC 12, 5) BAC 4, 6) BAC 5, 7) BAC 9, 8) BAC 12.

A large-insert cosmid binary cosmid (BAC) library constructed from *A. tauschii* variety *meyeri* (Moullet et al., 1999) was probed with the intron 3 region of SBEIIb gene (positions 2019 to 2391, FIG. 2) to isolate BACs containing the SBEIIb gene. Four positive clones were isolated and designated BAC-4, -5, -9 and -12. To confirm that they contained the SBEIIb gene, DNA from these clones was extracted, digested with HindIII or EcoR1 and a Southern blot hybridisation carried out using the same probe (FIG. 12). The clone BAC-5 showed one strong hybridising band of size ~7.5 kB with EcoR1 and four bands of sizes ~6.1, 3.6, 2.3 and 1.7 with HindIII (FIG. 12). This demonstrated the presence of SBEIIb on BAC-5. To test for the presence of the 3' region of the gene on BAC-5, PCR amplifications were carried out on this clone using specific primers designed to amplify exons 17 (AR2b3pr2F, 5'-GGATATGTATGATTTCATGG-3' [SEQ ID No. 22], and AR2b3pr2R, 5'-CCATAAAGTTAAGATAACCC-3') [SEQ ID No. 23] and 20 (AR2b3pr1F, 5'-GACATCAGACCAC-CAGTACG-3' [SEQ ID No. 24], and AR2b3pr1R, 5'-CTTC-CCAGGCTTTAAACAGC-3') [SEQ ID No. 25], based on SBEIIb cDNA sequence. Both sets of primers amplified the expected products of sizes 128 bp for exon 17 and 145bp for exon 20 indicating that BAC-5 contained the 3' end of SBEIIb. This was further confirmed by sequencing the PCR product from exon 20.

BAC-5 was also tested for the presence of the SBEIIa gene in addition to SBEIIb. Nucleotide sequencing reactions using the primer AR2akpnIF 5'-GGTACCGCAGAAAATATAC-GAGATTGACCC-3' [SEQ ID No. 26] yielded the sequence corresponding to the intron 3 region of the SBEIIa gene, being the same as the sequence from positions 2265 to 2478 (FIG. 1) of wSBE II-D1. This result suggested that SBEIIa was also present on BAC-5, and meant that SBEIIa and SBEIIb were probably closely linked in wheat.

Fluorescence In Situ Hybridization (FISH).

In situ hybridization with the wSBE II-D1 genomic clone F2 (Rahman et al., 2001) and a wSBE II-D2 clone (Rahman et al., 2001) was performed on chromosome squashes from *Aegilops tauschii* and wheat as described by Turner et al., (1999). The identity of the hybridized chromosome was verified by double labeling with pSc119.2, a repetitive sequence used for chromosome identification (Mukai et al., 1990). Both of the wSBEII clones hybridized to the proximal region of chromosome 2 (FIG. 13), indicating the proximity of the two SBEII genes in wheat.

Wheat SBEIIb Null Mutants are also Mutant for SBEIIa

The SBEIIb null mutants identified as described above were screened for mutations in the SBEIIa gene using the primers Sr913F (5'-ATCACTTACCGAGAATGGG-3') [SEQ ID No. 27] and E6R (5'-CTGCATTTGGATTCCAATTG-3') [SEQ ID No. 28]. These primers were designed to amplify the intron 5 region of wSBE II-D1 and distinguish the SBEIIa genes on the A, B and D genomes.

The SBEIIb B genome null mutants Aus12565 and Aus12509 were found to be also B genome null mutants of the SBEIIa gene. Similarly, the D genome null mutants of SBEIIb, Aus17340 and Aus10103, were also D genome null mutants of SBEIIa. Furthermore, the B+D genome double mutant lines of SBEIIb, BD341 and BD636, were also B+D genome double null mutants of the SBEIIa gene. The data proves that SBEIIa and SBEIIb are closely linked in wheat, in contrast to rice and maize, and indicate that the mutations for the B and D genome copies of these genes described above represent deletion mutations.

Triple Null SBEIIa Wheat Mutants.

The methods described above may be used to isolate A genome mutants of SBEIIa and/or SBEIIB. For example, regions of BAC-5 closely linked to SBEIIa and/or SBEIIb are used as probes or for the design of PCR primers to screen for A-genome mutations in the genes. A-genome mutants are crossed with the B+D double null lines to produce a A+B+D triple null line. Alternatively, mutagenesis of the B+D genome double null mutants is carried out by irradiation or other means and a triple null mutant entirely lacking SBEIIa activity and optionally SBEIIb activity is identified. A non-transgenic wheat variety with very high amylose levels is thereby provided.

Example 10

Mutation of SBEIIa Gene in Wheat

Mutation of the SBEIIa gene in wheat leading to reduced activity of SBEIIa can be achieved through either gamma ray irradiation or chemical mutagenesis, for example with ethyl methane sulfonate (EMS). For gamma ray induced mutation, seeds are irradiated at a dose of 20-50 kR from a $^{60}$Co source (Zikiryaeva and Kasimov, 1972). EMS mutagenesis is performed by treating the seeds with EMS (0.03%, v/v) as per Mullins et al., (1999). In a B+D double null background, mutant grains are identified on the basis of increased amylose content or altered starch grain morphology and confirmed by the methods described above. Mutants in SBEIIa that retain SBEIIb activity can be re-mutagenized and the progeny screened for loss of SBEIIb activity in addition to SBEIIa, or the SBEIIa mutant can be crossed with an SBEIIb mutant to combine the mutations and produce a non-transgenic variety of wheat substantially lacking SBEII activity in the endosperm.

Example 11

SGP-1 Wheat Mutants are Reduced in SBEIIa and SBEIIb Activity

The genes for starch synthase II (SSII) from the A, B and D genomes of wheat (*Triticum aestivum*) encode polypeptides of 100-105 kDa that are also known as Starch Granule Proteins-1 (SGP-1). SSII (SGP-1) consists of three polypeptides of approximate molecular masses of 100, 104 and 105 kDa which are encoded by a homeologous set of genes on the short arm of chromosomes 7B, 7A and 7D respectively (Denyer et al., 1995; Yamamori and Endo, 1996). Yamamori et al. (2000) produced an SGP-1 null wheat by crossing lines which were lacking the A, B and D genome specific forms of SGP-1 protein as assayed by protein electrophoresis. Examination of the SGP-1 null seeds showed that the mutation resulted in alterations in amylopectin structure, elevated amylose content and deformed starch granules (Yamamori et al., 2000). In addition, electrophoretic experiments on mature grain revealed that the levels of granule-bound SBEII (SGP-2) and SSI (SGP-3) decreased considerably. The molecular basis of the mutation(s) leading to the SGP-1 null line was not known.

We undertook experiments to further characterize a wheat line completely lacking SGP-1 in starch granules from mature grain. To determine whether the SSII genes are present in each of the A, B and D genomes of SGP-1 null wheat, DNA was extracted from the SGP-1 null wheat and wild-type (control) cv Chinese Spring wheat and analysed by PCR using the primer combinations ssl[a (5'-CCAAGTAC-CAGTGGTGAACGC-3') [SEQ ID No. 29] and ssIIb (5'-CGGTGGGATCCAACGGCCC-3') [SEQ ID No. 30] for B genome or ssIIa and ssIIc (5'-CATGT-GAGCTAGCTTTCGCCC-3') [SEQ ID No. 31] for the A and D genomes. The amplified region was between positions 2472-2821 bp of wSSIIA (GenBank accession no. AF155217) or the corresponding regions of wSSIIB or wSSIID. The amplified region constituted a part of exon 8 and was chosen because it allowed the clear discrimination of the A, B and D genome products. Amplification was performed using 35 cycles at 94° C. for 30 sec, 60° C. for 1 min and 72° C. for 2 min. The PCR fragments produced from A, B and D genomes of SGP-1 null wheat were the same size as the corresponding fragments produced from Chinese Spring. PCR amplification of gene segments of the isoamylase and SSI genes, which are the most closely located starch biosynthetic genes to SSII and positioned on either side of SSII (Li et al., 2002), showed that these genes could be amplified from each of the A, B and D genomes of SGP-1 null wheat. Therefore, the SGP-1 null phenotype was not caused by the deletion of any of these genes on the short arm of chromosome 7.

When examined by scanning electron microscopy, starch granules from SGP-1 null developing seed, from 10 days post anthesis to maturity, were clearly deformed. The chain length distribution of debranched starch in the mutant showing an increase in the ratio of shorter chains (up to DP 8) and a decrease in the ratio of DP 9-22 when examined by capillary electrophoresis.

Expression of Starch Synthases and Branching Enzymes in SGP-1 Endosperin.

Figure 14:
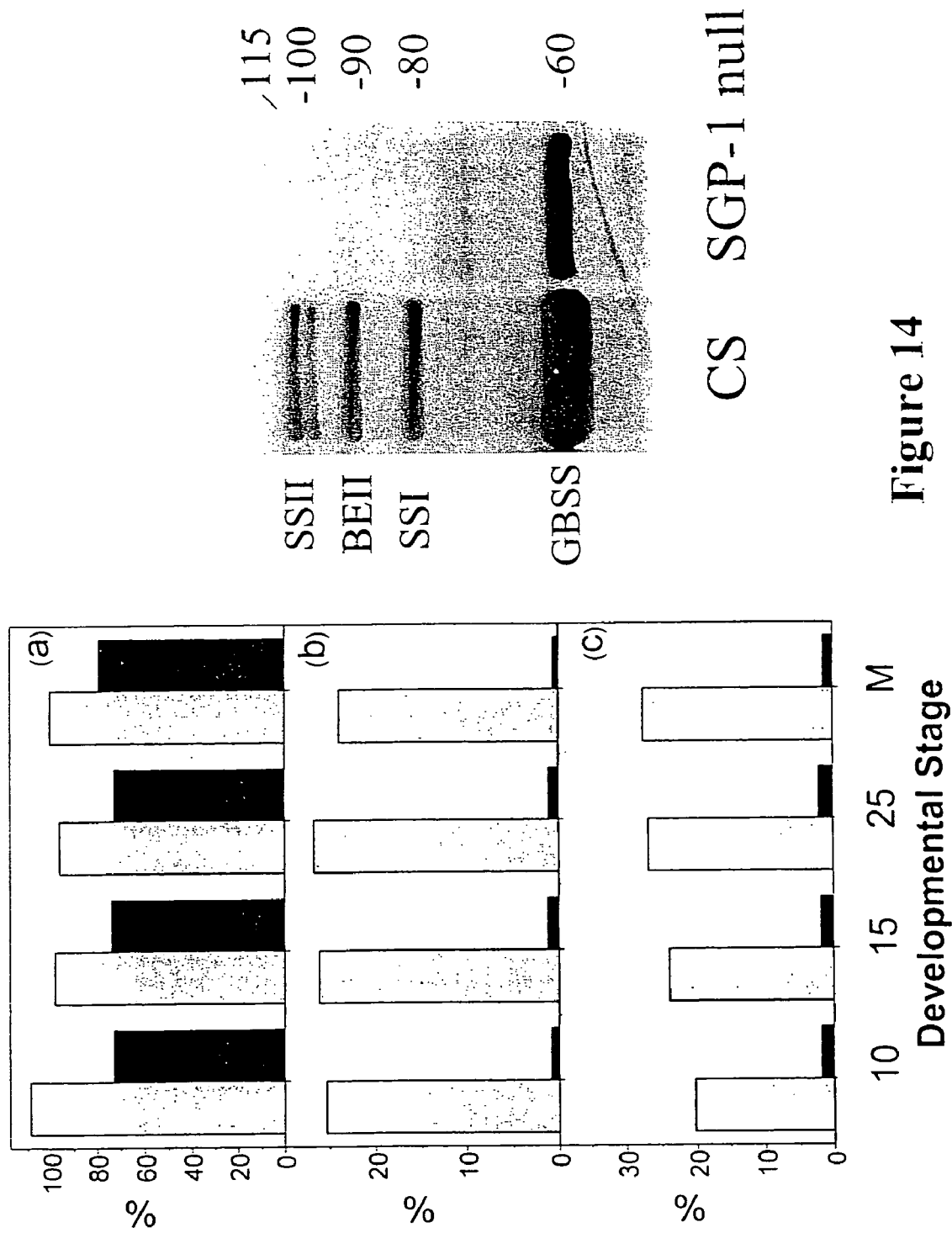
FIG. 14. SDS-PAGE analysis of granule bound proteins in wild-type Chinese Spring (CS) and SGP-1 null wheat lines at several stages of seed development (10, 15, 25 days after anthesis, M=mature) as indicated. The protein band intensity of the image of the silver stained gel was measured. The band intensity of GBSS in mature CS seed was normalized to 100 and the amount of other enzymes at indicated developmental stage is expressed as percentage of GBSS in mature CS. a) GBSS, b) SSI, c) SBEII. Black bars refer to SGP-1 null. An exemplary gel electrophoretogram for granule bound proteins from CS and the SGP-1 null line is shown.

The expression of starch synthases and branching enzymes in the starch granules was investigated in the SGP-I null and compared to those in wild-type cultivar Chinese Spring. Regardless of the stage of seed development, there was significant reduction of approximately 90%-96% in the amounts of SBEII and SSI in the granules in the SGP-1 null line, in addition to the absence of SSII (FIG. 14). Use of specific antibodies showed that the SBEII band obtained from the granules was composed of SBEIIa and SBEIIb in the approximate ratio of 1:3 in Chinese Spring. In the SGP-1 null mutant, the amount was so low that the relative proportions could not be determined using the antibodies. There was also a decrease in the GBSS I level from an early stage of grain development. It is clear that in the SGP-1 mutant there is a reduced level of starch granule-associated polypeptides including SBEIIa and SBEIIb. The reduction in starch-granule associated polypeptides (SBEII and SSI) was not observed in the grains of the wheat lines used to produce the SGP-1 null (Yamamori et al., 2000) and suggests that the effect is specifically caused by the absence of SSII.

Figure 15:
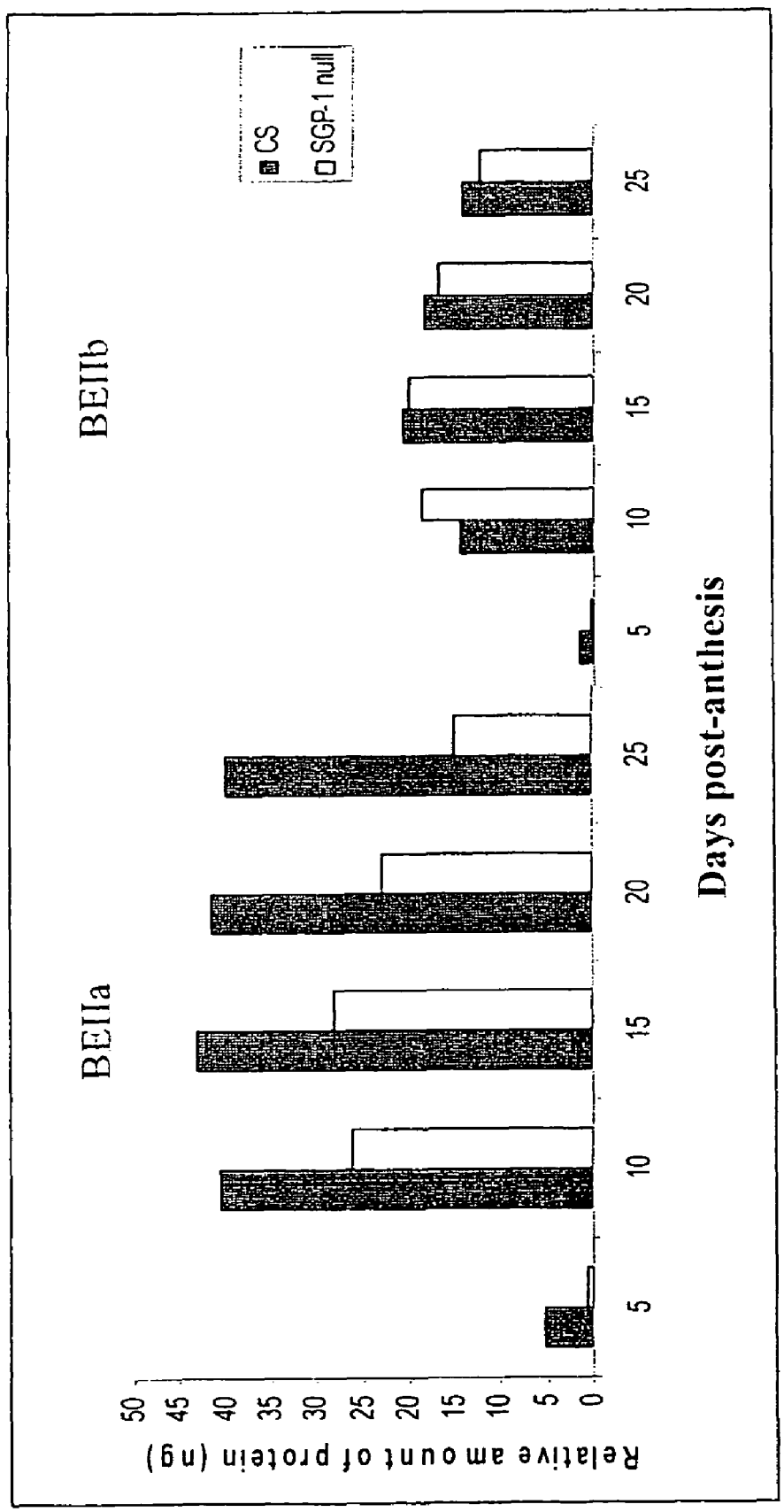
FIG. 15. Relative amounts of SBEIIa and SBEIIb in the soluble fraction. Immunoblots of the SDS-PAGE were scanned and the protein band intensity of the images were measured. The amounts of proteins were estimated from SBEIIa- and SBEIIb-fusion proteins used on the gels as standard.

Branching enzymes and starch synthases were also analysed in the soluble phase of developing endosperm. While the relative amount of soluble SBEIIb was similar in Chinese Spring and the SGP-1 null line, there was a reduction in the amount of SBEIIa in the soluble phase of the mutant (FIG. 15). However, this may have been due in part to the genealogy of the SGP-1 null line.

These data demonstrate that SBEIIa activity can be decreased pleiotropically by mutation in the SSII gene. Although mutation in SSII alone led to relative amylose levels in the starch of less than 50%, it suggests that mutations in genes other than SBEIIa can be combined with SBEII mutations to increase amylose levels and produce altered starches.

Example 12

Knockout of SBEI-Multiple Isoforms

Figure 16:
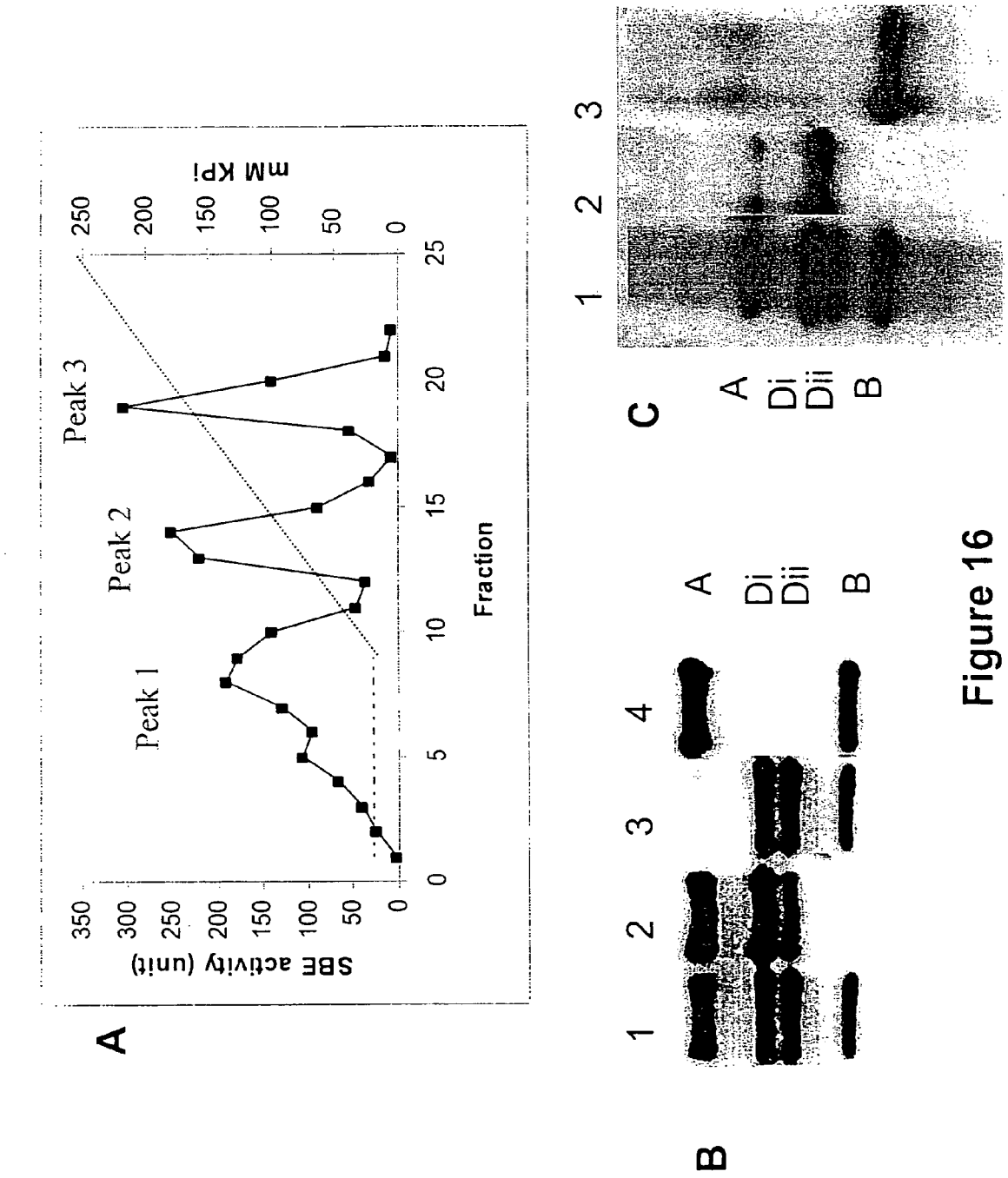
FIG. 16. A. Anion-exchange chromatography of wheat (cv Rosella) endosperm branching enzyme activities. Endosperm-soluble proteins were fractionated with ammonium sulphate and chromatographed on a Sephacryl S-200 column prior to application to a Resource Q anion exchange column. B) Immuno-detection analysis using anti-WBE1 antibody of wheat endosperm SBEI separated on a non-denaturing PAGE. The SBEI protein bands labelled as A and B are products from the A and B genomes respectively and Di and Dii are products from the D genome. Lanes correspond to extracts from: 1. CS, lane 2. N7BT7A, lane 3. N7AT7B, lane 4. N7DT7A. C) Immuno-detection analysis of purified fractions representing active peaks in the anion-exchange chromatogram using anti-WBE 1 antibody. Lane 1. endosperm crude soluble extract, lane 2. fractions representing peak 1, lane 3. fraction representing peak 2.

Purification of wheat starch branching enzymes through anion exchange chromatography resolved three peaks of activity (FIG. 16, Morell et al., 1997). Endosperm extracts from the cultivar Chinese Spring (CS) revealed the presence of four SBEI polypeptides on a non denaturing PAGE using a polyclonal antibody, anti-WBE-1, raised against a synthetic peptide with the amino acid sequence corresponding to the N-terminal sequence of the protein of peak 1 (FIG. 16B). Analysis of CS nullisomic-tetrasomic lines revealed that these polypeptides were encoded on chromosome 7; the bands on the immunoblot were assigned to the A (A band), B (B band) and D (Di and Dii bands) genomes and the activities were termed the A-major, B-major and D-major activities, respectively. Immunoblot analysis of the purified fractions representing the active peaks obtained by anion exchange chromatography revealed that the first peak contained the SBEI A-major and D-major activities and the second peak contained the SBEI B-major activity (FIG. 16C).

The location of the gene encoding the major SBEI activity on chromosome 7 is consistent with the determined location of three well-characterised and related genes, wSBEI-D2, wSBEI-D3 and wSBEI-D4. The deduced protein sequence of SBEI-major showed that it is encoded by the last of these genes, wSBEI-D4 (Rahman et al., 1997, Suzuki et al., 2003). The presence of a fourth SBEI gene was suggested on the basis of Southern blot hybridization data (Suzuki et al., 2003).

Identification of Null Mutations of SBE I-Major

In order to identify null mutations that lack expression of one or more SBEI isoforms, wheat germplasm collections were screened by immunoblot detection of SBEI-major after non-denaturing gel electrophoresis. The anti-wSBEI antibody described above was used. Of 182 Australian hexaploid wheat accessions analysed, 13 lines were identified that did not express SBEI-D major, 16 that lacked SBEI-B major, 10 that lacked SBEI-A, and two (Bindawarra and Vectis) that lacked both of the A and B isoforms. These lines were considered to have null mutations of the respective genome SBEI genes. The frequency of null mutations in the SBEI-major gene (~23%) was similar to that of the GBSS gene (22%) (Boggini et al., 2001).

Generation of SBE I-Major Triple Null Line

Figure 17:
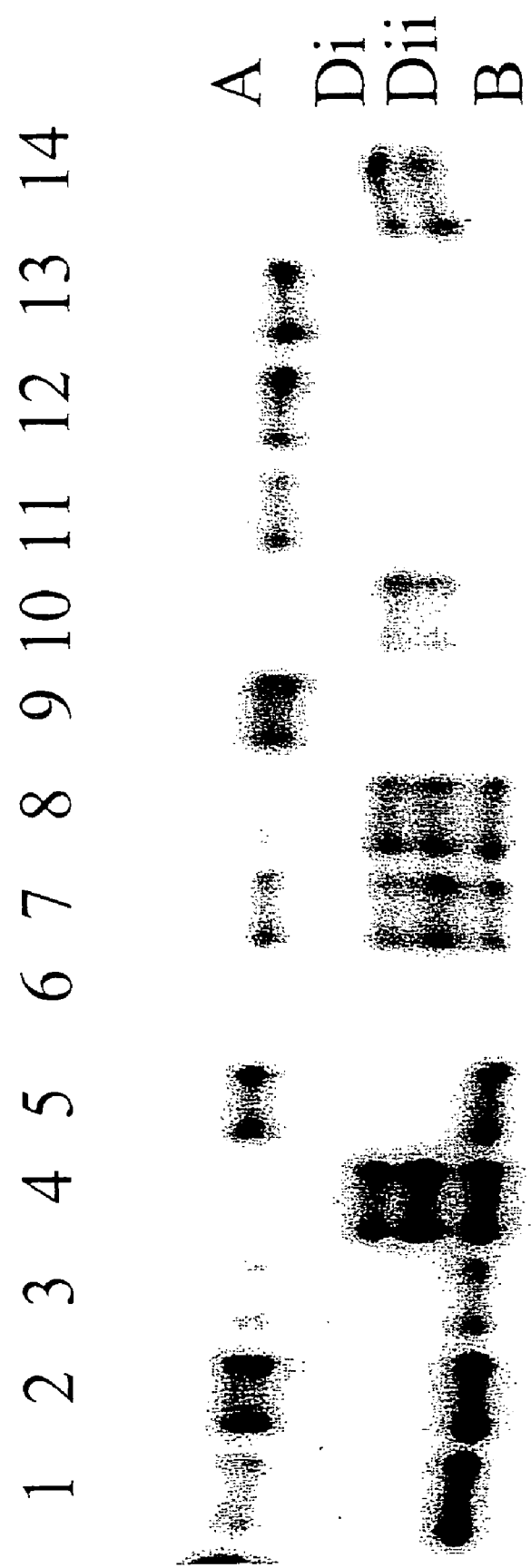
FIG. 17. Screening of doubled haploid progeny of the cross VC3.1.11×CS7AL-15 for segregation of SBEI isoforms by immuno-detection using anti-WBE I antibody. Lanes 1 to 14 correspond to doubled haploid progeny lines. Lane 6 is a triple null SBEI mutant line designated as A113 and lane 7 is a line normal for SBEI isoforms designated as D28.

From the immunoblot analysis, it was clear that cultivars Bindwarra and Vectis were missing the A-major and B-major SBEI activities and the cultivar Cadoux was identified as missing the D-major activity. An F2 progeny population of 185 lines obtained from the cross Vectis×Cadoux were screened by immunoblotting. However, no lines missing all of the three activities were obtained, suggesting that either such progeny had low viability or there was some type of interaction between the genomes. Therefore, the progeny line VC3.1.11 that was missing the B- and D-major activities was crossed with a chromosome engineered Chinese Spring line (CS7AL-15) that was missing the A-major activity. Doubled haploid lines were screened by both PCR using the primers ARBE1CF (5'-GGGCAAACGGAATCTGATCC-3') [SEQ ID No. 32] and ARA9R (5'-CCAGATCGTATATCGGAAG-GTCG-3') [SEQ ID No. 33] and immunoblotting and 2 lines (A113 and D13) out of 160 were that entirely lacked SBEI-major activity as judged by immunoblotting on non-denaturing gels. FIG. 17 shows a representative segregation pattern of doubled haploid lines including A113 (lane 6).

Endosperm of line A 113 was examined for residual SBE activity. A wild-type wheat variety, D28, showed two peaks of SBEI activity. In contrast, A113 extracts gave the first peak but the second peak of activity was completely missing. Amino acid sequences obtained from the purified fraction comprising this activity indicated the presence of a SBEI type of protein in A113. However, this fraction did not show a reaction with anti-WBEI antibody in a non-denaturing gel. The branching activity in A113 corresponded to a ~80 kDa protein which may be of a SBEII type enzyme as it cross-reacted with potato SBE and maize SBEII antibodies.

These data demonstrate that SBEI mutant lines can be generated in wheat. Combination of SBEI mutations with SBEIIa and optionally SBEIIb mutations produces wheat plants having very high amylose levels in the grain starch.

Example 13

Identification of Mutant Wheat Lines Comprising Chromosome 2A with a Mutation in an SBEII Gene In an attempt to identify a wheat line having a mutation in an SBEIIa or SBEIIb gene, 2400 hexaploid wheat accessions were screened for null mutations of SBEIIb in the A, B or D genomes. The primers AR2b19cF/AR2b23cR were used in PCR reactions on genomic DNA samples of wheat plants of each line, followed by digestion of the amplification products with RsaI and gel electrophoresis. This marker amplified the intron 3 region (nucleotide positions 2085 to 2336 in wheat SBEIIb gene, FIG. 2) and was specific for SBEIIb. This screening had resulted in the identification of three D genome SBEII-null mutants and two B genome SBEII-null mutants as described in the Examples above. No mutant lines which lacked the A genome band corresponding to SBEIIb were detected. This suggested that wheat lines comprising chromosome 2A with a mutant SBEIIb gene do not occur naturally.

Figure 18:
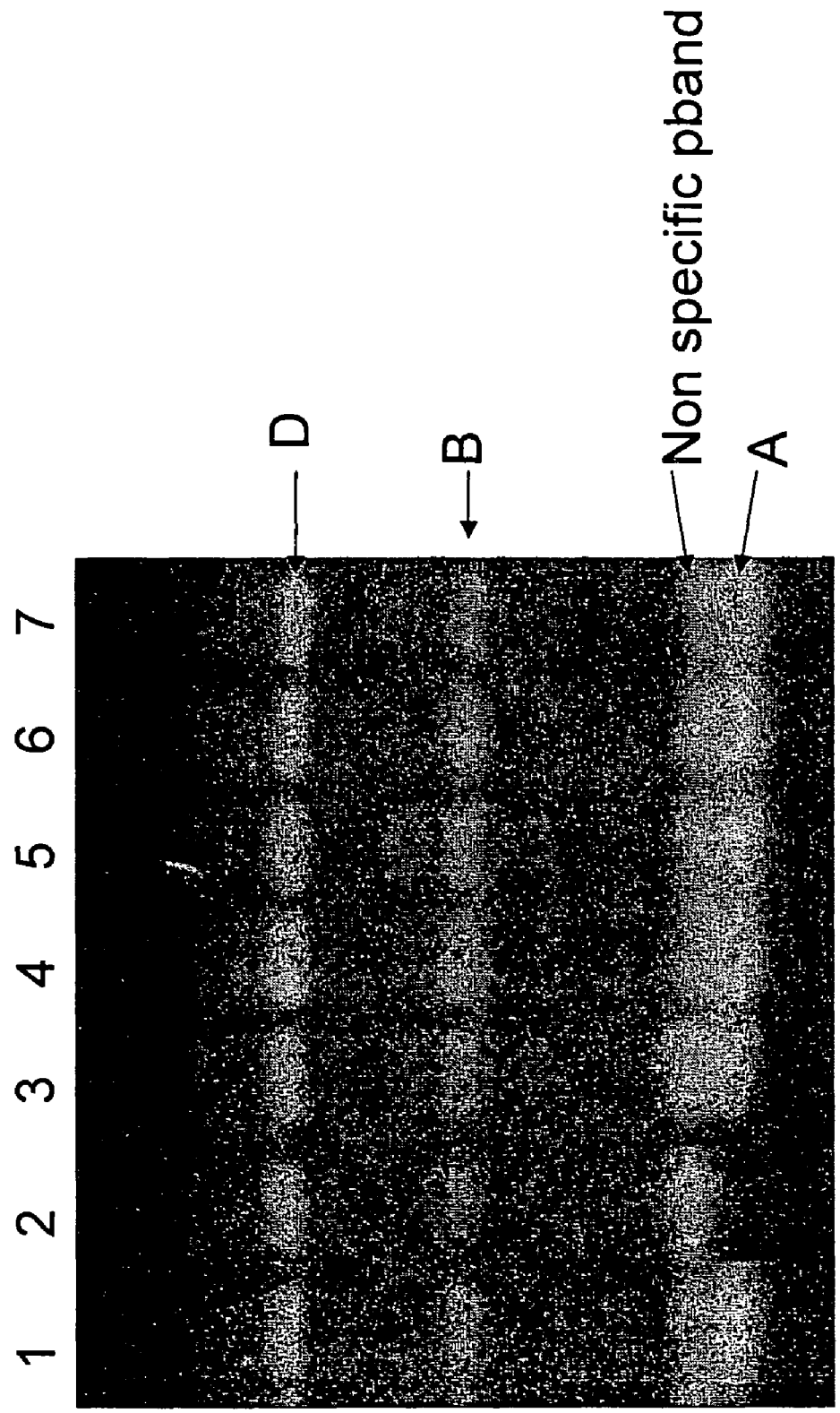
FIG. 18. PCR amplification of DNA from gamma ray induced mutant seeds (Lanes 1 to 6) of the cross Veery 3×Gabo 1BL.1RS using the primers AR2b19cF/AR2b23cR. Lane 2 represents the mutant seed MLT2B8 and Lane 7 represents Chinese Spring.

A gamma ray ($^{60}$Co source) induced mutant wheat population generated by Tony Prior and Rohit Mago (CSIRO) was used to screen for induced mutations in wheat SBEII. The wheat population was generated from the F2 progeny of a cross, Gabo 1BL.1R×Veery 3. A total of 2694 mutant seeds from this population were screened as described above in PCR reactions with the primers AR2b19cF and AR2b23cR. Two seeds, designated MLT2B8 and MLT2D1, that came from one plant, were identified that lacked the SBEIIb A genome allele (FIG. 18). No seeds in the population were identified to contain null mutations of SBEIIb in the B or D genomes.

As shown in the Examples above, SBEIIa and SBEIIb genes were closely linked in wheat on the long arm of chromosome 2. Accordingly, we tested DNA from these seeds for the presence or absence of the A genome SBEIIa gene with PCR reactions using the primers Sr913F/E6R. These primers amplify the intron 5 region of wSBEII-D1 (nucleotide positions 2959 to 3189, FIG. 1 [SEQ ID No. 1]). After amplification, the products were electrophoresed on a 5% sequencing gel (ABI Prism DNA sequencer). Fluorescently labeled products were analysed using the software Genescan. The scan profiles showed that the amplification products for both of the mutant seeds MLT2B8 and MLT2D1 lacked the product corresponding to the A genome SBEIIa gene, indicating that both seeds had null alleles for the A genome SBEIIa in addition to SBEIIb.

Figure 19:
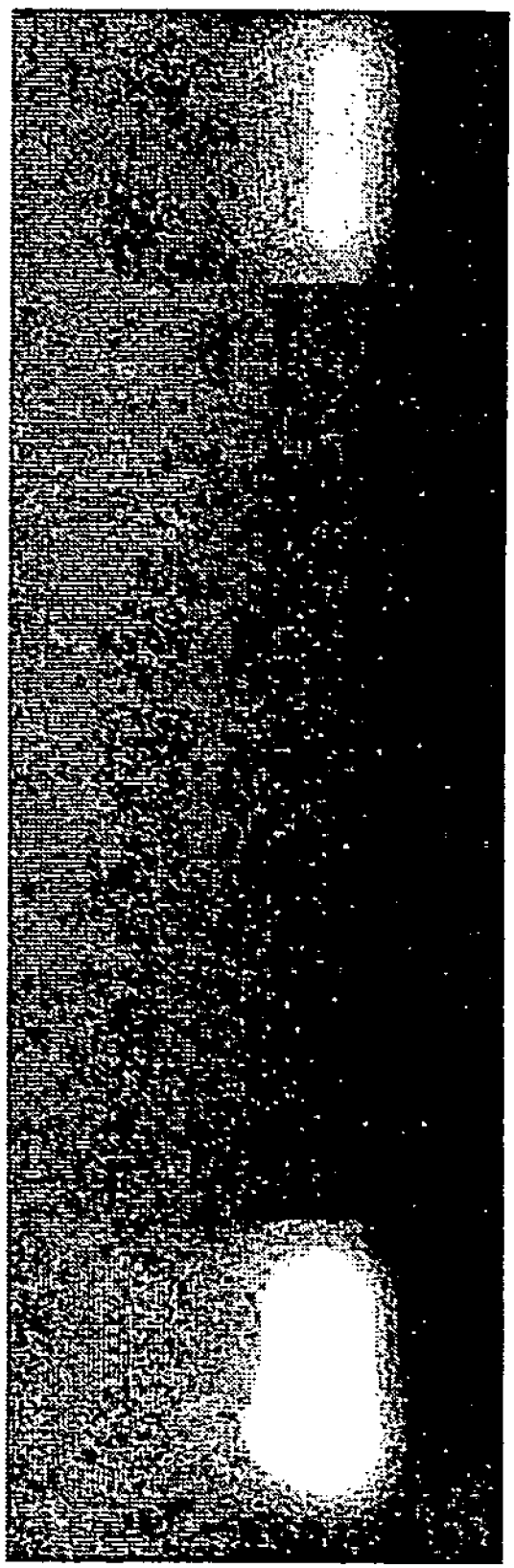
FIG. 19. PCR amplification of DNA from wheat lines using A genome specific primers for wheat SBEIIa gene, ARIIaAF/ARIIaAR. Lanes in the order of 1 to 5 are CS, MLT2B8, MLT2D1, Dt2AS and BD219 (plant that is null mutant for both SBEIIa and SBEIIb plant in both B and D genomes).

The null mutations in these seeds were further confirmed by using an A genome specific marker for SBEIIa, ARIIaAF (5'-GCAAAAGCCAGATCATAAATTTAGAGC-3') [SEQ ID No. 34] and ARIIaAR (5'-CTTCCAATTCATTGT-TAATGGTCACAC-3') [SEQ ID No. 35] that amplify only the product from A genome SBEIIa gene (nucleotide positions 3024 to 3131 of wSBE II-DA1, FIG. 1). While this pair of primers amplified a 110 bp product from plant material from the variety Chinese Spring, this product was clearly missing in the two putative mutant seeds. This was the same as for the negative control dt2AS, which is a chromosome engineered line of Chinese Spring that is missing the long arm of chromosome 2A. Since the SBEIIa and SBEIIb genes are located on the long arm of chromosome 2, this line lacks the A genome allele of both these genes and hence could be used as a negative control (FIG. 19).

The embryos from the mutant seeds MLT2B8 and MLT2D 1, identified to be A genome mutants for SBEIIa and SBEIIb, are grown to produce plants. The starch obtained from seed from these plants is analysed for amylose content, chain length and other properties to determine if the null mutations of both the SBEIIa and SBEIIb on the A genome affect starch properties.

As described above, five lines having mutation in both the B and D genome SBEIIa and SBEIIb genes had been generated. Of these, lines BD 219 and BD 636 are grown in a greenhouse and crossed to the A null mutant lines MLT2B8 and MLT2D1. A doubled haploid population is generated from the F1 seeds of these crosses to provide homozygous triple null mutant plants. Such triple null mutant plants should occur in doubled haploid populations at a frequency of 1 in 8. The A genome null mutations can be combined with either the B genome mutations or the D genome mutations by similar crosses. In further crosses, any of the null alleles can be introduced into any suitable genetic background for agronomic. or other traits.

The following crosses are performed to produce durum wheat (such as, for example, variety Wollaroi) having mutations in the A genome SBEIIa and SBEIIb:

1) Wollaroi×MLT2B8 or MLT2D1, to produce A-genome SBEIIa/SBEIIb null durum in Wollaroi background.
2) A-genome null durum (Wollaroi)×B-genome null SBEIIa/SBEIIb wheat line to produce AB double null SBEIIa/SBEIIb durum (Wollaroi)

Alternatively,

1) Wollaroi×B-genome null wheat line, to produce B-genome null durum (Wollaroi)
2) B-genome null Wollaroi×A null wheat line, to produce AB double null SBEIIa/SBEIIb durum.

These crosses result in the generation of high amylose durum wheat which will have specific end uses with health benefits similar to that of high amylose hexaploid wheat.

Example 14

Confirmation of the High Amylose Content in Grain by Sepharose 2B Column Separation Methods The amylose content of starch in the grain of transgenic wheat plants containing SBEIIa/SBEIIb inhibitory genetic constructs was determined by a Sepharose column separation method. In this method, starch molecules were separated on the column based on their molecular weight. The separated fractions were then assayed using the Starch Assay Kit (Sigma) according to the suppliers instructions.

Approximately 10 mg of starch was dissolved in 3.0 ml of 1N NaOH (de-gased) by incubation at 37° C. for 30 min. The starch solution was centrifuged for 15 min to spin down the undissolved components. The supernatant was loaded on to a Sepharose CL2B column at a pump speed of 1 ml/min. The column was run using 10 mM NaOH as buffer and fifty fractions of 2.5 ml each were collected. The pH of fractions 9 to 50 was adjusted to 4.5 with 35 µl of 1 M HCl. An aliquot (250 µl) of each sample was transferred into a tube followed by the addition of 250 µl of Starch reagent (Starch assay kit, Sigma). The controls included: a starch assay reagent blank containing only starch reagent (250 µl) and water (250 µl), a glucose assay reagent blank containing only 500 µl water, a sample blank containing only 250 µl starch sample and 250 µl water and a sample test containing only 250 µl starch reagent and 250 µl starch sample. The samples and the controls were incubated at 60° C. for 60 min, and then 200 µl of each transferred to a new tube followed by addition of 1 ml of glucose reagent (starch assay kit, Sigma) and incubation at 37° C. for 30 min. The absorbance at 340 nm was used to determine the quantity of starch (mg) in each fraction according to the instructions supplied with the kit.

The chromatogram of starch samples revealed two peaks eluted from the Sepharose column. The amylose content (second peak) of each sample was calculated as a percentage of the total amount of starch within both of the peaks.

Using this method, the amylose content of the ds-SBEIIa transgenic line Acc. 144087, which was shown to be homozygous for the transgene, was calculated to be 78% and that of a ds-SBEIIb transgenic line Acc 144008 (homozygous transgenic line from the event IIb 110.16b) was estimated to be 23% (FIG. 20). In comparison, the iodometric method gave amylose contents for these lines of 88.47% and 27.29%, respectively (Table 10).

Functional properties such as gelatinization temperature, paste viscosity and starch swelling volume are analysed by Differential Scanning Calorimetry (DSC), Rapid Visco Analyser (RVA) and starch swelling power test, respectively. The structure of these starches is analysed by X-ray crystallography and particle size analysis.

TABLE 10

Amylose content of wheat transgenic lines estimated by iodometric method

| Line | Target enzyme | Event No. | Amylose content (%) |
|---|---|---|---|
| NB1 | Non transformed | — | 31.8 |
| 144008 | SBE IIb | IIb 110.16b | 27.3 |
| 144087 | SBE IIa | IIa 85.3a | 88.5 |
| 144025 | SBE IIa | IIa 50.1b | 75.8 |
| LSD | — | — | 7.7 |

Example 15

Chain Length Distribution Analysis

Figure 21:
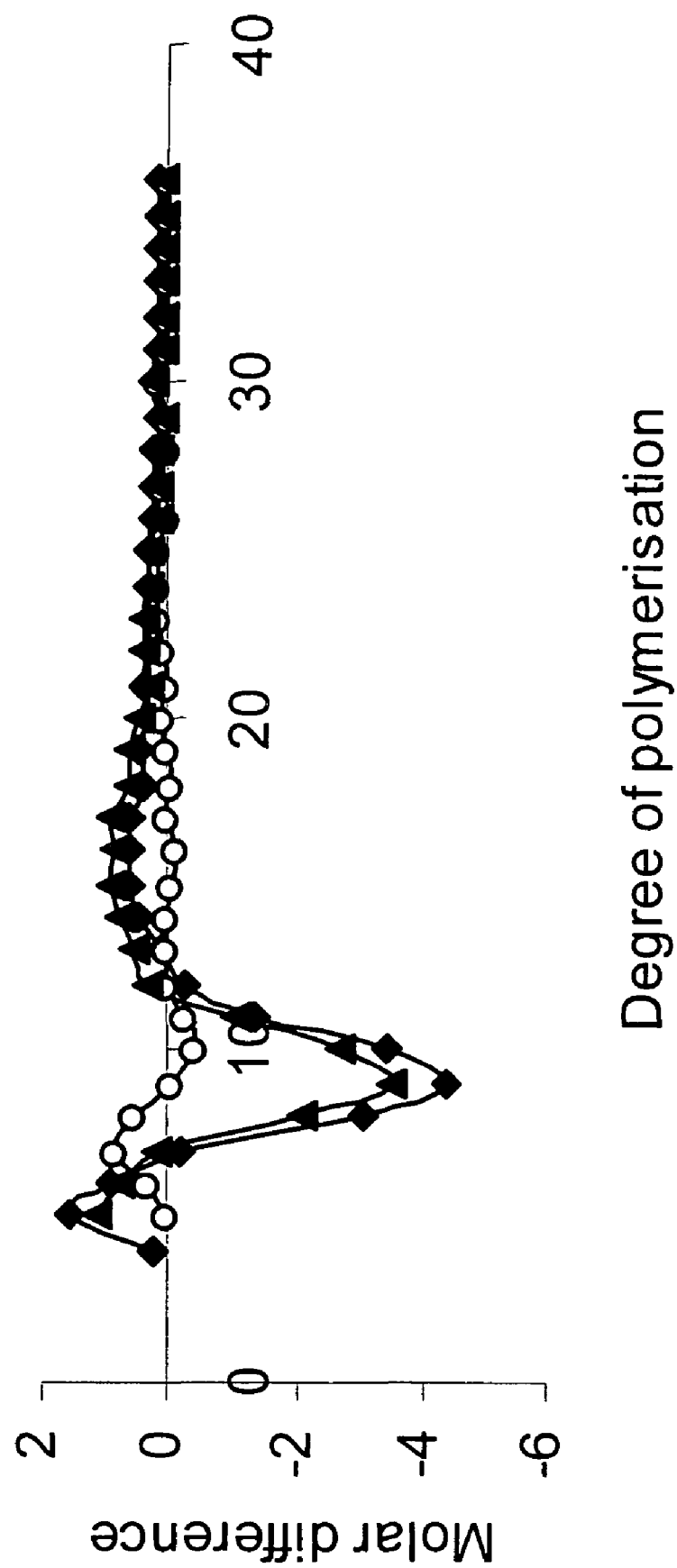
FIG. 21. Chain length profile comparison of starches from wheat transgenic lines with respect to that of non transformed control, NB1 (wheat). The percentage of total mass of individual oligosaccharides from starches from the non transformed control is subtracted from the corresponding values from starches from transgenic lines. Samples are 085 (♦), 025 (▲), 008 (○).

The chain length distribution of starch samples was determined by fluorophore assisted carbohydrate electrophoresis (FACE) after isoamylase de-branching of the starch. The percentages of chain lengths from DP 6-11, DP 12-30 and DP 31-60 in starch from the transgenic seed compared to non-transgenic controls are presented in Table 11. Molar difference plots in which the normalized chain length distributions for starch from high amylose transgenic lines were subtracted from the normalized distribution for starch from the isogenic non transformed controls are given in FIG. 21.

TABLE 11

Chain length distribution of isoamylase debranched starches from wheat transgenic lines

| Line | Targeted gene | Event No | DP4–12 | DP13–24 | DP24–36 | >36 |
|---|---|---|---|---|---|---|
| NB1 | Nontransformed control | — | 57.39 | 37.38 | 3.83 | 1.40 |
| 144087 | SBEIIa | IIa 85.3a | 47.40 | 42.27 | 6.16 | 4.17 |
| 144025 | SBEIIa | IIa 50.1b | 49.99 | 44.40 | 5.60 | — |
| 144008 | SBEIIb | IIb 110.16b | 57.98 | 37.65 | 4.37 | — |

There was a significantly lower proportion of chain lengths of DP 4-12 in starch from ds-SBEIIa transgenic seed compared to starch from untransformed seed or ds-SBEIIb transgenic seed. The proportion of chain lengths of >DP 13 was higher in ds-SBEIIa transgenic seed compared to the others. These results suggest the possibility that SBEIIa is selectively involved in the synthesis of shorter chains of DP 4-12 in wheat starch. In starch from the SSIIa mutant, however, there was an increase in the proportion of shorter chain lengths in the amylose.

Example 16

Properties of Starch from Transgenic Wheat

Physical properties of starch from ds-SBEIIa and ds-SBEIIb transgenic lines including the gelatinisation temperature were analysed using a Perkin Elmer Diamond differential scanning calorimeter. Approximately 20 mg of each starch was mixed with water at a ratio of 1:2 i.e. to a moisture content of 66.7%, and sealed in a DSC pan. A heating rate of 10° C. per minute was used to heat the test and reference samples from 0 to 150° C. Data were analysed using the software available with the instrument.

Two endotherm peaks were observed in the thermogram DSC trace for each starch. The first peak represented the breakdown of crystalline structure during gelatinization of starch. The second peak represented the amylose-lipid dissociation endotherm. The gelatinization peak temperature of starch from ds-SBEIIa transgenic lines showed an increase of approximately 7-10° C. compared to the peak temperature for a non-transformed control starch, and approximately 3 to 7° C. increased compared to starch from a ds-SBEIIb transgenic line.

TABLE 12

Thermal properties of transgenic wheat starch measured by differential scanning calorimeter (DSC).

| Lines | Enzyme targeted | Peak 1 (Gelatinisation) | | | | | Peak 2 (Amylose-lipid dissociation) | | | |
| --- | --- | --- | --- | --- | --- | --- | --- | --- | --- | --- |
| | | Onset | Peak | End | Area | ΔH | Onset | Peak | End | ΔH |
| 008 | SBE IIb | 58.8 | 63.7 | 70.8 | 234.8 | 4.5 | 93.2 | 103.5 | 110.3 | 0.7 |
| 012 | SBE IIb | 59.0 | 64.1 | 70.8 | 262.6 | 4.3 | 94.5 | 103.1 | 109.7 | 0.6 |
| 121 | SBE IIa | 53.7 | 67.5 | 86.9 | 156.4 | 2.6 | 92.4 | 102.9 | 108.9 | 0.7 |
| 087 | SBE IIa | 53.1 | 71.9 | 85.9 | 142.6 | 2.4 | 95.7 | 102.7 | 108.9 | 0.7 |
| 114 | SBE IIa | 53.0 | 68.1 | 88.0 | 125.2 | 2.1 | 92.8 | 102.5 | 109.6 | 0.8 |
| 109c | Control* | 55.9 | 60.7 | 68.8 | 234.3 | 3.9 | 97.2 | 104.6 | 109.9 | 0.4 |

A marked increase in the end temperature of gelatinization (first peak) of approximately 16–19° C. was observed in these lines compared to both non-transformed control and ds-SBEIIb transgenic lines. The temperature of onset of gelatinization appeared to be earlier in ds-SBEIIa transgenic lines than the control or ds-SBEIIb transgenic lines. Ng et al., 1997 reported a gelatinization onset temperature of amyloseextender (ae) maize starch similar to that of normal maize starch, but a significant increase in the peak gelatinization temperature in ae starch compared to normal starch. The gelatinization enthalpy of starch from ds-SBEIIa transgenic lines was significantly lower than that of both the control and ds-SBEIIb lines. This seems to be reflecting the significantly lower gelatinization peak area which represents the reduced amount of amylopectin in ds-SBEIIa transgenic lines. No significant alteration was observed in the amylose-lipid dissociation peak in any of the transgenic lines. We have therefore obtained starch with this novel set of properties.

REFERENCES

Abel et al., (1996). *The Plant Journal* 10, 981-991.
Anderson et al., (1989). *Nucl Acids Res* 17, 461-462.
Baba et al., (1991). *Biochem Biophys Res Commun* 181: 87-94.
Batey and Curtin. (1996). *Starch* 48, 338-344.
Batey et al., (1997). *Cereal Chemistry* 74, 497-501.
Becker et al., (1994). *Plant J.* 5: 299-307.
Blauth et al., (2001). *Plant Physiology* 125, 1396-1405.
Bourque. (1995). *Plant Science* 105, 125-149.
Boyer and Preiss, (1978). *Carbohydrate Research* 61, 321-334.
Boyer and Preiss, (1981). *Plant Physiology* 67, 1141-1145.
Boyer et al., (1980). *Starch* 32, 217-222.
Buleon et al., (1998). *International Journal of Biological Macromolecules* 23, 85-112.
Cao et al., (2000). *Archives. of Biochemistry and Biophysics.* 373, 135-146.
Case et al., (1998). *Journal of Cereal Science* 27, 301-314.
Cheng et al, (1997). *Plant Physiol* 115: 971-980.
Craig et al., (1998). *Plant Cell* 10, 413-426.
Denyer et al., (1995). *Planta* 196: 256-265.
Denyer et al., (1996). *Plant Physiology* 112, 779-785.
Feldman. (***) pp 3-56 in The World Wheat Book, A history of wheat breeding. Eds Bonjean and Angus, Lavoisier Publishing, Paris.
Fergason. 1994. pp 55-77 in "Speciality Corns" eds, CRC Press Inc.
Filpse et al.,(1996). *Planta* 198, 340.
Fisher et al., (1993). *Plant Physiol* 102:1045-1046.
Fisher et al., (1996). *Plant Physiol* 110: 611-619.
Fuwa et al., (1999). *Starch/Starke.* 51, 147-151.
Gao et al., (1997). *Plant Physiol* 114: 69-78.
Gao et al., (1998). *Plant Cell* 10, 399-412.
Giroux and Hannah. (1994). *Molecular and General Genetics* 243, 400-408.
Green et al., (1997). *Plant Physiology* 114, 203-212.
He et al., (1994). *Plant Cell Reports* 14: 192-196.
Hedman and Boyer, (1982). *Biochemical Genetics* 20, 483-492.
Hess et al., (1990). *Plant Science* 72: 233-244.
James et al., (1995). *Plant Cell* 7, 417-429.
Jobling et al., (1999). *Plant Journal* 18, 163-171.
Komari et al., (1996). *Plant Journal* 10: 165-174.
Konik-Rose et al (2001) *Starch* 53, 14-20.
Krueger et al., (1987). *Cereal Chemistry* 64, 187-190.
Kubo et al., (1999). *Plant physiology.* 121, 399-409.
Li et al., (1999a). *Plant physiology.* 120, 1147-1155.
Li et al., (1999b). *Theoretical and Applied Genetics* 98, 1208-1216.
Li et al., (2000). *Plant Physiology* 123, 613-624.
Li et al., (2003). *Funct Integr Genomics* 3:76-85.
Maniatis et al., (1982). Molecular cloning: a laboratory manual. Cold Spring Harbour Laboratory Press New York.
McCreery and Helentjaris (1994). Methods in Molecular Biology, Vol. 28: Protocols for nucleic acid analysis by non-radioactive probes, 67-71, Humana Press Inc., Totawa, N.J.
Mizuno et al., (1993). *Journal of Biological Chemistry* 268, 19084-19091.
Mizuno et al., (1992). *Journal of Biochemistry* 112, 643-651.
Morell et al., (1997). *Plant Physiology* 113, 201-208.
Morell et al., (1998). *Electrophoresis* 19, 2603-2611.
Morell et al., (2003). *Plant J* 34: 173-185.
Morrison and Laignelet (1983). *Journal of Cereal Science* 1:9-20.
Mullins et al., (1999). *European Journal of Plant Pathology* 105: 465-475.
Myers et al., (2000). *Plant Physiology* 122, 989-997.
Nakamura (2002). *Plant Cell Physiology* 43, 718-725.
Nakamura and Yamanouchi (1992). *Plant Physiol* 99: 1265-1266.
Nair et al., (1997). *Plant Sci* 122: 153-163.
Nehra et al., (1994). *Plant J* 5: 285-297.
Ng et al., (1997) *Cereal Chemistry* 74: 288-292.
Nishi et al., (2001). *Plant Physiology* 127, 459-472.
Rahman et al., (1995). *Australian Journal of Plant Physiology* 22, 793-803.
Rahman et al., (1997). *Genome* 40: 465-474.
Rahman et al., (1999). *Theor Appl Genet.* 98: 156-163.
Rahman et al., (2000). *J Cereal Sci* 31: 91-110.
Rahman et al., (2001). *Plant Physiol* 125: 1314-1324.
Repellin et al., (1997). *Plant Gene Reg* 97-094
Safford et al., (1998). *Carbohydrate Polymers* 35, 155-168.
Schulman and Kammiovirta, (1991). *Starch* 43, 387-389.
Schwall et al., (2000). *Nature Biotechnology* 18, 551-554.

Senior (1998). *Biotechnology and Genetic Engineering Reviews* 15, 79-119.
Shannon and Garwood, (1984). In *Starch: Chemistry and Technology*, Whistler et al., eds, Academic Press, Orlando, Fla., pp25-86.
Shure et al., (1983). *Cell* 35, 225-233.
Sidebottom et al., (1998). *Journal of Cereal Science* 27, 279-287.
Stacey and Isaac (1994). Methods in Molecular Biology, Vol. 28: Protocols for nucleic acid analysis by non-radioactive probes, pp 9-15, Humana Press Inc., Totawa, N.J.
Sun et al., (1997). *The New Phytologist* 137, 215-215.
Takeda et al., (1993a). *Carbohydrate Research* 240, 253-262.
Takeda et al., (1993b). *Carbohydrate Research* 246, 273-281.
Thomas and Atwell 1999 Starches Eagen Press, St Paul, Minn., USA pp: 13-24.
Thorbjomsen et al., (1996). *Plant Journal* 10, 243-250.
Vasil et al., (1992). *Bio/Technology* 10: 667-674.
Vasil et al., (1993). *Bio/Technology* 11: 1553-1558.
Wang et al., (1998). *Journal of Experimental Botany* 49, 481-502.
Weeks et al., (1993). *Plant Physiol* 102: 1077-1084.
Wegener et al., 1994. *Mol. Gen Genet.* 245, 465-470.
Weir et al., (2001). *Aust J Plant Physiol* 28: 807-818.
Yamamori and Endo, (1996). *Theoretical and Applied Genetics* 93, 275-281.
Yamamori et al., (2000). *Theor. Appl. Genet.* 101, 21-29
Young. (1984). in Whistler et al. (eds), Academic Press, Orlando, Fla., chap 8.
Zhao and Sharp, (1998). *Plant Breeding* 117: 488-490.
Zikiryaeva and Kasimov, (1972). *Uzbekskii Biologicheskii Zhurnal* 6, 18-20.
Zwar and Chandler, (1995). *Planta* 197, 39-48.

---

SEQUENCE LISTING

```
<160> NUMBER OF SEQ ID NOS: 35

<210> SEQ ID NO 1
<211> LENGTH: 11476
<212> TYPE: DNA
<213> ORGANISM: Aegilops tauschii
<220> FEATURE:
<221> NAME/KEY: misc_feature
<222> LOCATION: (1722)..(1722)
<223> OTHER INFORMATION: n=a,c,t or g
<220> FEATURE:
<221> NAME/KEY: misc_feature
<222> LOCATION: (4794)..(4794)
<223> OTHER INFORMATION: n=a,c,t or g
<220> FEATURE:
<221> NAME/KEY: misc_feature
<222> LOCATION: (4972)..(4972)
<223> OTHER INFORMATION: n=a,c,t or g
<220> FEATURE:
<221> NAME/KEY: misc_feature
<222> LOCATION: (5077)..(5077)
<223> OTHER INFORMATION: n=a,c,t or g
<220> FEATURE:
<221> NAME/KEY: misc_feature
<222> LOCATION: (5078)..(5078)
<223> OTHER INFORMATION: n=a,c,t or g
<220> FEATURE:
<221> NAME/KEY: misc_feature
<222> LOCATION: (5081)..(5081)
<223> OTHER INFORMATION: n=a,c,t or g
<220> FEATURE:
<221> NAME/KEY: misc_feature
<222> LOCATION: (7009)..(7009)
<223> OTHER INFORMATION: n=a,c,t or g
<220> FEATURE:
<221> NAME/KEY: misc_feature
<222> LOCATION: (7326)..(7326)
<223> OTHER INFORMATION: n=a,c,t or g
<220> FEATURE:
<221> NAME/KEY: misc_feature
<222> LOCATION: (7380)..(7380)
<223> OTHER INFORMATION: n=a,c,t or g
<220> FEATURE:
<221> NAME/KEY: misc_feature
<222> LOCATION: (7383)..(7383)
<223> OTHER INFORMATION: n=a,c,t or g
<220> FEATURE:
<221> NAME/KEY: misc_feature
<222> LOCATION: (7818)..(7818)
<223> OTHER INFORMATION: n=a,c,t or g
<220> FEATURE:
<221> NAME/KEY: misc_feature
<222> LOCATION: (8188)..(8188)
<223> OTHER INFORMATION: n=a,c,t or g
```

<220> FEATURE:
<221> NAME/KEY: misc_feature
<222> LOCATION: (10458)..(10458)
<223> OTHER INFORMATION: n=a,c,t or g

<400> SEQUENCE: 1

| | | | | | | |
|---|---|---|---|---|---|---|
| agaaacacct | ccattttaga | ttttttttt | gttcttttcg | gacggtgggt | cgtggagaga | 60 |
| ttagcgtcta | gttttcttaa | aagaacaggc | catttaggcc | ctgctttaca | aaaggctcaa | 120 |
| ccagtccaaa | acgtctgcta | ggatcaccag | ctgcaaagtt | aagcgcgaga | ccaccaaaac | 180 |
| aggcgcattc | gaactggaca | gacgctcacg | caggagccca | gcaccacagg | cttgagcctg | 240 |
| acagcggacg | tgagtgcgtg | acacatgggg | tcatctatgg | gcgtcggagc | aaggaagaga | 300 |
| gacgcacatg | aacaccatga | tgatgctatc | aggcctgatg | gagggagcaa | ccatgcacct | 360 |
| tttcccctct | ggaaattcat | agctcacact | tttttttaat | ggaagcaaga | gttggcaaac | 420 |
| acatgcattt | tcaaacaagg | aaaattaatt | ctcaaaccac | catgacatgc | aattctcaaa | 480 |
| ccatgcaccg | acgagtccat | gcgaggtgga | aacgaagaac | tgaaaatcaa | catcccagtt | 540 |
| gtcgagtcga | aagaggatg | acactgaaag | tatgcgtatt | acgatttcat | ttacatacat | 600 |
| gtacaaatac | ataatgtacc | ctacaatttg | tttttggag | cagagtggtg | tggtcttttt | 660 |
| tttttacacg | aaaatgccat | agctggcccg | catgcgtgca | gatcggatga | tcggtcggag | 720 |
| acgacggaca | atcagacact | caccaactgc | ttttgtctgg | gacacaataa | atgttttgt | 780 |
| aaacaaaata | aatacttata | aacgagggta | ctagaggccg | ctaacggcat | ggccaggtaa | 840 |
| acgcgctccc | agccgttggt | ttgcgatctc | gtcctcccgc | acgcagcgtc | gcctccaccg | 900 |
| tccgtccgtc | gctgccacct | ctgctgtgcg | cgcgcacgaa | gggaggaaga | acgaacgccg | 960 |
| cacacacact | cacacacggc | acactccccg | tgggtcccct | ttccggcttg | gcgtctatct | 1020 |
| cctctccccc | gcccatcccc | atgcactgca | ccgtacccgc | cagcttccac | ccccgccgca | 1080 |
| cacgttgctc | ccccttctca | tcgcttctca | attaatatct | ccatcactcg | ggttccgcgc | 1140 |
| tgcatttcgg | ccggcgggtt | gagtgagatc | tgggcgactg | gctgactcaa | tcactacgcg | 1200 |
| gggatggcga | cgttcgcggt | gtccggcgcg | actctcggtg | tggcgcgggc | cggcgtcgga | 1260 |
| gtggcgcggg | ccggctcgga | gcggaggggc | ggggcggact | tgccgtcgct | gctcctcagg | 1320 |
| aagaaggact | cctctcgtac | gcctcgctct | ctcgaatctc | ccccgtctgg | ctttggctcc | 1380 |
| ccttctctct | cctctgcgcg | cgcatggcct | gttcgatgct | gttccccaat | tgatctccat | 1440 |
| gagtgagaga | gatagctgga | ttaggcgatc | gcgcttcctg | aacctgtatt | ttttcccccg | 1500 |
| cggggaaatg | cgttagtgtc | acccaggccc | tggtgttacc | acggctttga | tcattcctcg | 1560 |
| tttcattctg | atatatattt | tctcattctt | tttcttcctg | ttcttgctgt | aactgcaagt | 1620 |
| tgtggcgttt | tttcactatt | gtagtcatcc | ttgcattttg | caggcgccgt | cctgagccgc | 1680 |
| gcggcctctc | cagggaaggt | cctggtgcct | gacggcgaga | gngacgactt | ggcaagtccg | 1740 |
| gcgcaacctg | aagaattaca | ggtacacaca | ctcgtgccgg | taaatcttca | tacaatcgtt | 1800 |
| attcacttac | caaatgccgg | atgaaaccaa | ccacgatgc | gtcaggtttc | gagcttcttc | 1860 |
| tatcagcatt | gtgcagtact | gcactgcctt | gttcattttg | ttagccttgg | ccccgtgctg | 1920 |
| gctcttgggc | cactgaaaaa | atcagatgga | tgtgcattct | agcaagaact | tcacaacata | 1980 |
| atgcaccgtt | tggggtttcg | tcagtctgct | ctacaattgc | tattttcgt | gctgtagata | 2040 |
| cctgaagata | tcgaggagca | aacggcgaa | gtgaacatga | caggggggac | tgcagagaaa | 2100 |
| cttcaatctt | cagaaccgac | tcagggcatt | gtggaaacaa | tcactgatgg | tgtaaccaaa | 2160 |

-continued

```
ggagttaagg aactagtcgt gggggagaaa ccgcgagttg tcccaaaacc aggagatggg      2220
cagaaaatat acgagattga cccaacactg aaagattttc ggagccatct tgactaccgg      2280
taatgcctac ccgctgcttt cgctcatttt gaattaaggt cctttcatca tgcaaatttg      2340
gggaacatca aagagacaaa gactagggac caccatttca tacagatccc ttcgtggtct      2400
gagaatatgc tgggaagtaa atgtataatt gatggctaca atttgctcaa aattgcaata      2460
cgaataactg tctccgatca ttacaattaa agagtggcaa actgatgaaa atgtggtgga      2520
tgggttatag attttacttt gctaattcct ctaccaaatt cctagggggg aaatctacca      2580
gttgggaaac ttagtttctt atctttgtgg cctttttgtt ttggggaaaa cacattgcta      2640
aattcgaatg attttgggta tacctcggtg gattcaacag atacagcgaa tacaagagaa      2700
ttcgtgctgc tattgaccaa catgaaggtg gattggaagc attttctcgt ggttatgaaa      2760
agcttggatt tacccgcagg taaatttaaa gctttattat tatgaaacgc ctccactagt      2820
ctaattgcat atcttataag aaaatttata attcctgttt tcccctctct tttttccagt      2880
gctgaaggta tcgtctaatt gcatatctta taagaaaatt tatattcctg ttttcccta       2940 ttttccagtg ctgaaggtat cacttaccga gaatgggctc cctggagcgc atgttatgtt      3000
cttttaagtt ccttaacgag acaccttcca atttattgtt aatggtcact attcaccaac      3060
tagcttactg gacttacaaa ttagcttact gaatactgac cagttactat aaatttatga      3120
tctggctttt gcaccctgtt acagtctgca gcattagtag gtgacttcaa caattggaat      3180
ccaaatgcag atactatgac cagagtatgt ctacagcttg gcaattttcc acctttgctt      3240
cataactact gatacatcta tttgtattta tttagctgtt tgcacattcc ttaaagttga      3300
gcctcaacta catcatatca aaatggtata atttgtcagt gtcttaagct tcagcccaaa      3360
gattctactg aatttagtcc atcttttga gattgaaaat gagtatatta aggatgaatg       3420
aatacgtgca acactcccat ctgcattatg tgtgcttttc catctacaat gagcatattt      3480
ccatgctatc agtgaaggtt tgctcctatt gatgcagata tttgatatgg tcttttcagg      3540
atgattatgg tgtttgggag attttcctcc ctaacaacgc tgatggatcc tcagctattc      3600
ctcatggctc acgtgtaaag gtaagctggc caattattta gtcgaggatg tagcattttc      3660
gaactctgcc tactaagggt ccctttttcct ctctgttttt tagatacgga tggatactcc     3720
atccggtgtg aaggattcaa tttctgcttg gatcaagttc tctgtgcagg ctccaggtga      3780
aatacctttc aatggcatat attatgatcc acctgaagag gtaagtatcg atctacatta      3840
cattattaaa tgaaatttcc agtgttacag tttttttaata cccacttctt actgacatgt     3900
gagtcaagac aatactttg aatttggaag tgacatatgc attaattcac cttctaaggg       3960 ctaagggca accaaccttg gtgatgtgtg tatgcttgtg tgtgacataa gatcttatag       4020 ctctttttatg tgttctctgt tggttaggat attccatttt ggccttttgt gaccatttac     4080
taaggatatt tacatgcaaa tgcaggagaa gtatgtcttc caacatctca actaaacgac      4140
cagagtcact aaggatttat gaatcacaca ttggaatgag cagcccggta tgtcaataag      4200
ttatttcacc tgtttctggt ctgatggttt attctctgga ttttctagtt ctgttatgta     4260
ctgttaacat attacatggt gcattcactt gacaacctcg attttatttt ctaatgtctt      4320
catattggca agtgcaaaac tttgcttcct cttttgtctgc ttgttctttt gtcttctgta    4380
agatttccat tgcatttgga ggcagtgggc atgtgaaagt catatctatt ttttttttgt      4440
cagagcatag ttatatgaat tccattgttg ttgcaatagc tcggtataat gtaaccatgt      4500
tactagctta agatttccca cttaggatgt aagaaatatt gcattggagc gtctccagca      4560
```

```
agccatttcc taccttatta atgagagaga gacaagggg ggggggggg gggggttccc    4620 ttcattattc tgcgagcgat tcaaaaactt ccattgttct gaggtgtacg tactgcaggg    4680
atctcccatt atgaagagga tatagttaat tctttgtaac ctacttggaa acttgagtct    4740
tgaggcatcg ctaatatata ctatcatcac aatacttaga ggatgcatct gaanatttta    4800
gtgtgatctt gcacaggaac cgaagataaa ttcatatgct aattttaggg atgaggtgtt    4860
gccaagaatt aaaaggcttg gatacaatgc agtgcagata atggcaatcc aggagcattc    4920
atactatgca agctttgggt attcacacaa tccattttttt tctgtataca cntcttcacc    4980
catttggagc tattacatcc taatgcttca tgcacataaa atatttggat ataatccttt    5040
attagatata tagtacaact acacttagta ttctgannaa naagatcatt ttattgttgt    5100
tggcttgttc caggtaccat gttactaatt tttttgcacc aagtagccgt tttggaactc    5160
cagaggactt aaaatcctg atcgatagag cacatgagct tggtttgctt gttcttatgg    5220
atattgttca taggtaatta gtccaattta attttagctg ttttactgtt tatctggtat    5280
tctaaaggga aattcaggca attatgatac attgtcaaaa gctaagagtg gcgaaagtga    5340
aatgtcaaaa tctagagtgg cataaggaaa attggcaaaa actagagtgg caaaaataaa    5400
attttcccat cctaaatggc agggccctat cgccgaatat ttttccattc tatataattg    5460
tgctacgtga cttcttttt ctcagatgta ttaaaccagt tggacatgaa atgtatttgg    5520
tacatgtagt aaactgacag ttccatagaa tatcgttttg taatggcaac acaatttgat    5580
gccatagatg tggattgaga agttcagatg ctatcaatag aattaatcaa ctggccatgt    5640
actcgtggca ctacatatag tttgcaagtt ggaaaactga cagcaatacc tcactgataa    5700
gtggccaggc cccacttgcc agcttcatac tagatgttac ttccctgttg aattcatttg    5760
aacatattac ttaaagttct tcatttgtcc taagtcaaac ttctttaagt ttgaccaagt    5820
ctattggaaa atatatcaac atctacaaca ccaaattact ttgatcagat taacaatttt    5880
tattttatta tattagcaca tctttgatgt tgtagatatc agcacatttt tctatagact    5940
tggtcaaata tagagaagtt tgacttagga caaatctaga acttcaatca atttggatca    6000
gagggaacat caaataatat agatagatgt caacacttca acaaaaaaat cagaccttgt    6060
caccatatat gcatcagacc atctgtttgc tttagccact tgcttcata tttatgtgtt    6120 tgtacctaat ctacttttcc ttctacttgg tttggttgat tctatttcag ttgcattgct    6180
tcatcaatga ttttgtgtac cctgcagtca ttcgtcaaat aatacccttg acggtttgaa    6240
tggtttcgat ggcactgata cacattactt ccacggtggt ccacgcggcc atcattggat    6300
gtgggattct cgtctattca actatgggag ttgggaagta tgtagctctg acttctgtca    6360
ccatatttgg ctaactgttc ctgttaatct gttcttacac atgttgatat tctattctta    6420
tgcaggtatt gagattctta ctgtcaaacg cgagatggtg gcttgaagaa tataagtttg    6480
atggatttcg atttgatggg gtgacctcca tgatgtatac tcaccatgga ttacaagtaa    6540
gtcatcaagt ggtttcagta acttttttag ggcactgaaa caattgctat gcatcataac    6600
atgtatcatg atcaggactt gtgctacgga gtcttagata gttccctagt atgcttgtac    6660
aattttacct gatgagatca tggaagattg gaagtgatta ttatttattt tcttctaag    6720 tttgtttctt gttctagatg acatttactg ggaactatgg cgaatatttt ggatttgcta    6780
ctgatgttga tgcggtagtt tacttgatgc tggtcaacga tctaattcat ggactttatc    6840
ctgatgctgt atccattggt gaagatgtaa gtgcttacag tatttatgat ttttaactag    6900
```

```
ttaagtagtt ttattttggg gatcagtctg ttacactttt tgttagggt aaaatctctc    6960
ttttcataac aatgctaatt tataccttgt atgataatgc atcacttang taatttgaaa    7020
agtgcaaggg cattcaagct tacgagcata ttttttgatg gctgtaattt atttgatagt   7080
atgcttgttt gggttttca ataagtggga gtgtgtgact aatgttgtat tatttattta    7140
attgcggaag aaatgggcaa ccttgtcaat tgcttcagaa ggctaacttt gattccataa   7200
acgctttgga aatgagaggc tattcccaag gacatgaatt atacttcagt gtgttctgta   7260
catgtatttg taatagtggt ttaacttaaa ttcctgcact gctatggaat ctcactgtat   7320
gttgtnagtg tacacatcca caaacaagta atcctgagct ttcaactcat gagaaaatan   7380
gangtccgct tctgccagca ttaactgttc acagttctaa tttgtgtaac tgtgaaattg   7440
ttcaggtcag tggaatgcct acattttgca tccctgttcc agatggtggt gttggttttg   7500
actaccgcct gcatatggct gtagcagata aatggattga actcctcaag taagtgcagg   7560
aatattggtg attacatgcg cacaatgatc tagattacat tttctaaatg gtaaaaagga   7620
aaatatgtat gtgaatatct agacatttgc ctgttatcag cttgaatacg agaagtcaaa   7680
tacatgattt aaatagcaaa tctcggaaat gtaatggcta gtgtctttat gctgggcagt   7740
gtacattgcg ctgtagcagg ccagtcaaca cagttagcaa tattttcaga aacaatatta   7800
tttatatccg tatatganga aagttagtat ataaactgtg gtcattaatt gtgttcacct   7860
tttgtcctgt ttaaggatgg gcagtaggta ataaatttag ccagataaaa taaatcgtta   7920
ttaggtttac aaaaggaata tacagggtca tgtagcatat ctagttgtaa ttaatgaaaa   7980
ggctgacaaa aggctcggta aaaaaaactt tatgatgatc cagatagata tgcaggaacg   8040
cgactaaagc tcaaatactt attgctacta cacagctgcc aatctgtcat gatctgtgtt   8100
ctgctttgtg ctatttagat ttaaatacta actcgataca ttggcaataa taaacttaac   8160
tattcaacca atttggtgga taccaganat ttctgccctc ttgttagtaa tgatgtgctc   8220
cctgctgctg ttctctgccg ttacaaaagc tgttttcagt ttttgcatc attatttttg    8280
tgtgtgagta gtttaagcat gttttttgaa gctgtgagct gttggtactt aatacattct   8340
tggaagtgtc caaatatgct gcagtgtaat ttagcatttc tttaacacag gcaaagtgac   8400
gaatcttgga aaatgggcga tattgtgcac accctaacaa atagaaggtg gcttgagaag   8460
tgtgtaactt atgcagaaag tcatgatcaa gcactagttg gtgacaagac tattgcattc   8520
tggttgatgg ataaggtact agctgttact tttggacaaa agaattactc cctcccgttc   8580
ctaaatataa gtctttgtag agattccact atggaccaca tagtatatag atgcatttta   8640
gagtgtagat tcactcattt tgcttcgtat gtagtccata gtgaaatctc tacagagact   8700
tatatttagg aacggaggga gtacataatt gatttgtctc atcagattgc tagtgttttc   8760
ttgtgataaa gattggctgc ctcacccatc accagctatt tcccaactgt tacttgagca   8820
gaatttgctg aaaacgtacc atgtggtact gtggcggctt gtgaactttg acagttatgt   8880
tgcaatttc tgttcttatt tatttgattg cttatgttac cgttcatttg ctcattcctt    8940
tccgagacca gccaaagtca cgtgttagct gtgtgatctg ttatctgaat cttgagcaaa   9000
ttttattaat aggctaaaat ccaacgaatt atttgcttga atttaaatat acagacgtat   9060
agtcacctgg ctctttctta gatgattacc atagtgcctg aaggctgaaa tagttttggt   9120
gtttcttgga tgccgcctaa aggagtgatt tttattggat agattcctgg ccgagtcttc   9180
gttacaacat aacattttgg agatatgctt agtaacagct ctgggaagtt tggtcacaag   9240
tctgcatcta cacgctcctt gaggttttat tatggcgcca tctttgtaac tagtggcacc   9300
```

-continued

```
tgtaaggaaa cacattcaaa aggaaacggt cacatcattc taatcaggac caccatacta    9360
agagcaagat tctgttccaa ttttatgagt ttttgggact ccaaagggaa caaaagtgtc    9420
tcatattgtg cttataacta cagttgtttt tataccagtg tagttttatt ccaggacagt    9480
tgatacttgg tactgtgctg taaattattt atccgacata gaacagcatg aacatatcaa    9540
gctctctttg tgcaggatat gtatgatttc atggctctgg ataggcttca actcttcgca    9600
ttgatcgtgg catagcatta cataaaatga tcaggcttgt caccatgggt ttaggtggtg    9660
aaggctatct taacttcatg ggaaatgagt ttgggcatcc tggtcagtct ttacaacatt    9720
attgcattct gcatgattgt gatttactgt aatttgaacc atgctttttct ttcacattgt    9780 atgtattatg taatctgttg cttccaagga ggaagttaac ttctatttac ttggcagaat    9840
ggatagattt tccaagaggc ccacaaactc ttccaaccgg caaagttctc ccctggaaat    9900
aacaatagtt atgataaatg ccgccgtaga tttgatcttg taagttttag ctgtgctatt    9960
acattccctc actagatctt tattggccat ttatttcttg atgaaatcat aatgtttgtt   10020
aggaaagatc aacattgctt ttgtagtttt gtagacgtta acataagtat gtgttgagag   10080
ttgttgatca ttaaaaatat catgattttt tgcagggaga tgcagatttt cttagatatc   10140
gtggtatgca agagttcgat caggcaatgc agcatcttga ggaaaaatat ggggtatgtc   10200
actggtttgt ctttgttgca taacaagtca cagtttaacg tcagtctctt caagtggtaa   10260
aaaaagtgta gaattaattc ctgtaatgag atgaaaactg tgcaaaggcg gagctggaat   10320
tgcttttcac caaaactatt ttcttaagtg cttgtgtatt gatacatata ccagcactga   10380
caatgtaact gcagtttatg acatctgagc accagtatgt ttcacggaaa catgaggaag   10440
ataaggtgat catcctcnaa aagaggagat ttggtatttg ttttcaactt ccactggagc   10500
aatagctttt ttgactaccg tgttgggtgt tccaagcctg ggaagtacaa ggtatgcttg   10560 cctttcatt gtccaccctt caccagtagg gttagtgggg gcttctacaa ctttttaattc   10620 cacatggata gagtttgttg gtcgtgcagc tatcaatata agaatagggg taatttgtaa   10680
agaaaagaat ttgctcgagc tgttgtagcc ataggaaggt tgttcttaac agccccgaag   10740
cacataccat tcattcatat tatctactta agtgtttgtt tcaatcttta tgctcagttg   10800
gactcggtct aatactagaa ctattttccg aatctaccct aaccatccta gcagttttag   10860
agcagcccca tttggacaat tggctgggtt tttgttagtt gtgacagttt ctgctatttc   10920
ttaatcaggt ggccttggac tctgacgatg cactctttgg tggattcagc aggcttgatc   10980
atgatgtcga ctacttcaca accgtaagtc tgggctcaag cgtcacttga ctcgtcttga   11040
ctcaactgct tacaaatctg aatcaacttc ccaattgctg atgcccttgc aggaacatcc   11100
gcatgacaac aggccgcgct ctttctcggt gtacactccg agcagaactg cggtcgtgta   11160
tgcccttaca gagtaagaac cagcagcggc ttgttacaag gcaaagagag aactccagag   11220
agctcgtgga tcgtgagcga agcgacgggc aacggcgcga ggctgctcca agcgccatga   11280
ctggaggggg atcgtgcctc ttccccagat gccaggagga gcagatggat aggtagcttg   11340
ttggtgagcg ctcgaaagaa aatggacggg cctgggtgtt tgttgtgctg cactgaaccc   11400
tcctcctatc ttgcacattc ccggttgttt tgtacatat aactaataat tgcccgtgcg   11460
ctcaacgtga aaatcc                                                   11476
```

<210> SEQ ID NO 2
<211> LENGTH: 6520
<212> TYPE: DNA

```
<213> ORGANISM: Triticum aestivum
<220> FEATURE:
<221> NAME/KEY: misc_feature
<222> LOCATION: (4606)..(4606)
<223> OTHER INFORMATION: n=a,c,t or g
<220> FEATURE:
<221> NAME/KEY: misc_feature
<222> LOCATION: (4633)..(4633)
<223> OTHER INFORMATION: n=a,c,t or g
<220> FEATURE:
<221> NAME/KEY: misc_feature
<222> LOCATION: (4666)..(4666)
<223> OTHER INFORMATION: n=a,c,t or g
<220> FEATURE:
<221> NAME/KEY: misc_feature
<222> LOCATION: (4678)..(4678)
<223> OTHER INFORMATION: n=a,c,t or g
<220> FEATURE:
<221> NAME/KEY: misc_feature
<222> LOCATION: (4694)..(4694)
<223> OTHER INFORMATION: n=a,c,t or g
<220> FEATURE:
<221> NAME/KEY: misc_feature
<222> LOCATION: (4711)..(4711)
<223> OTHER INFORMATION: n=a,c,t or g
<220> FEATURE:
<221> NAME/KEY: misc_feature
<222> LOCATION: (5458)..(5458)
<223> OTHER INFORMATION: n=a,c,t or g
<220> FEATURE:
<221> NAME/KEY: misc_feature
<222> LOCATION: (5688)..(5688)
<223> OTHER INFORMATION: n=a,c,t or g
<220> FEATURE:
<221> NAME/KEY: misc_feature
<222> LOCATION: (5696)..(5696)
<223> OTHER INFORMATION: n=a,c,t or g
<220> FEATURE:
<221> NAME/KEY: misc_feature
<222> LOCATION: (5715)..(5715)
<223> OTHER INFORMATION: n=a,c,t or g
<220> FEATURE:
<221> NAME/KEY: misc_feature
<222> LOCATION: (5768)..(5768)
<223> OTHER INFORMATION: n=a,c,t or g
<220> FEATURE:
<221> NAME/KEY: misc_feature
<222> LOCATION: (5838)..(5838)
<223> OTHER INFORMATION: n=a,c,t or g
<220> FEATURE:
<221> NAME/KEY: misc_feature
<222> LOCATION: (5879)..(5879)
<223> OTHER INFORMATION: n=a,c,t or g
<220> FEATURE:
<221> NAME/KEY: misc_feature
<222> LOCATION: (5895)..(5895)
<223> OTHER INFORMATION: n=a,c,t or g
<220> FEATURE:
<221> NAME/KEY: misc_feature
<222> LOCATION: (5937)..(5937)
<223> OTHER INFORMATION: n=a,c,t or g
<220> FEATURE:
<221> NAME/KEY: misc_feature
<222> LOCATION: (5956)..(5956)
<223> OTHER INFORMATION: n=a,c,t or g
<220> FEATURE:
<221> NAME/KEY: misc_feature
<222> LOCATION: (5969)..(5969)
<223> OTHER INFORMATION: n=a,c,t or g
<220> FEATURE:
<221> NAME/KEY: misc_feature
<222> LOCATION: (6055)..(6055)
<223> OTHER INFORMATION: n=a,c,t or g
<220> FEATURE:
<221> NAME/KEY: misc_feature
<222> LOCATION: (6147)..(6147)
<223> OTHER INFORMATION: n=a,c,t or g
<220> FEATURE:
<221> NAME/KEY: misc_feature
```

<222> LOCATION: (6215)..(6215)
<223> OTHER INFORMATION: n=a,c,t or g

<400> SEQUENCE: 2

| | | | | | |
|---|---|---|---|---|---|
| aagctttgta | gccttgcacg | ggctccccaa | caaactgcct | cactcgattg | tcaaaaaagt | 60 |
| aaaaatgatt | gtagaaaaaa | aaactgactc | actcgtcact | accctaccgt | cctacatgac | 120 |
| acctggccgc | aagacgacgc | cgtcctcctg | ccgcgcgcgt | ccgcgatcac | accaccgcaa | 180 |
| aaaccaaaac | ctcttcgccg | gtgcgtccca | cgctaccatc | catgcagccg | tccgcccgcg | 240 |
| cgcgcgttgc | ccgcaccacc | cgctggcggc | caccacgccg | ccactctcgc | gtgaaggctc | 300 |
| cgtccgcttc | ctcctagttc | cactctctct | ccgtgctagc | agtatatagc | atccgccctc | 360 |
| cgcccctcc | caatcttaga | acaccctcc | ctttgcctcc | tcatttcgct | cgcgtgggtt | 420 |
| taagcaggag | acgaggcggg | gtcagttggg | cagttaggtt | ggatccgatc | cggctgcggc | 480 |
| ggcggcgacg | ggatggctgc | gccggcattc | gcagtttccg | cggcggggct | ggcccggccg | 540 |
| tcggctcctc | gatccggcgg | ggcagagcgg | aggggcgcg | gggtggagct | gcagtcgcca | 600 |
| tcgctgctct | tcggccgcaa | caagggcacc | cgttcacccc | gtaattattt | gcgccacctt | 660 |
| tctcactcac | attctctcgt | gtattctgtc | gtgctcgccc | ttcgccgacg | acgcgtgccg | 720 |
| attccgtatc | gggctgcggt | gttcagcgat | cttacgtcgg | ttccctcctg | gtgtggtgat | 780 |
| gtctgtaggt | gccgtcggcg | tcggaggttc | tggatggcgc | gtggtcatgc | gcgcgggggg | 840 |
| gccgtccggg | gaggtgatga | tccctgacgg | cggtagtggc | ggaacaccgc | cttccatcga | 900 |
| cggtcccgtt | cagttcgatt | ctgatgatct | gaaggtagtt | tttttttgc | atcgatctga | 960 |
| aggtacttga | catatactac | tgtattaccc | tgagtaaata | ctgccaccat | atttttatgg | 1020 |
| ttcgcttgaa | atacctgttt | acttgctacg | gttttcactt | tcattgagac | gtcggacgaa | 1080 |
| attcactgaa | ttcctataat | ttggtagaca | ccgaaatata | tactactcct | tccgtcccat | 1140 |
| aatataagag | cgttttggc | accttatatt | atagggcgga | gggagtacct | tttaggtcaa | 1200 |
| aatattgtgg | tagtttcaat | tgtatacaag | aattcaaata | ttttttttaa | aaaaaaatca | 1260 |
| actaattggt | tgagtttcaa | gtgaagcgtt | ttggtccttt | ggctgagatg | taaaccgaaa | 1320 |
| tcactgaaat | tcatagtagc | cgaaacttta | atagaactga | aactcaaaat | ctgctatccg | 1380 |
| gcgaaattct | aaagatttgc | ttatttcaca | cgtaggttgc | agtacaccct | ctttctaatt | 1440 |
| tattggggaa | ggggtattat | tatcttgtta | gtacctgcct | gcatgacaat | tgaaatctaa | 1500 |
| gacaaaacac | catatgcgag | gcctacacac | ggtaggttgg | tttacaacta | tgtgtgccac | 1560 |
| agttcgtctg | aacttttttgt | ccttcacatc | gtgttaggtt | ccattcattg | atgatgaaac | 1620 |
| aagcctacag | gatggaggtg | aagatagtat | ttggtcttca | gagacaaatc | aggttagtga | 1680 |
| agaaattgat | gctgaagaca | cgagcagaat | ggacaaagaa | tcatctacga | gggagaaatt | 1740 |
| acgcattctg | ccaccaccgg | gaaatggaca | gcaaatatac | gagattgacc | caacgctccg | 1800 |
| agactttaag | taccatcttg | agtatcggta | tgcttcgctt | ctattgtgtg | cactttaaaa | 1860 |
| acaatttaca | gtcttttgata | agatgtgaat | ggctgcttgc | tgtgacacga | aactcttgaa | 1920 |
| gttcgtagtc | actcttgtgt | gttcatggtt | ctgaggtaac | atggtaaccg | aacaaaaata | 1980 |
| ggaaagtggc | aagcactgca | atgtgagcta | ctgataacca | cccattgtaa | ttgggtacac | 2040 |
| tgattaatat | atatgtcttc | atgggctcta | ttttttttca | atatctatgc | caattgaaca | 2100 |
| acaatgcttt | gtggacgggt | gttctttttac | cctcttcttc | tatcaataga | tgatatgcat | 2160 |
| actcatgcgt | atcctacaaa | aaattgaaca | acaatgccac | tttccccgt | gttgcttttg | 2220 |

```
taaggatgaa acacatatgt ccagatcaaa ctatactagc agtctaactg tgccttaatg    2280
gatcaaaaac agatatagcc tatacaggag aatacgttca gacattgatg aacacgaagg    2340
aggcatggat gtattttccc gcggttacga gaagtttgga tttatgcgca ggtgaaattt    2400
cttgactaaa taactatgta tctacctttt ctttgtactc tatcaacatt cctcttccca    2460
tgcagcgctg aaggtatcac ttaccgagaa tgggctcctg gagcagatgt acgttcttct    2520
aaccatctga tcgtttacct gactatacta attctatctt tcaactaatt gtgaataatt    2580
actgctcatc agctatccta aggttgggga ttttgcacct cccagatgaa cagcatatta    2640
agtcgcacaa ctagcattat taagaactaa ctcctgcttc caattgcagt ctgcagcatt    2700
agttggcgac ttcaacaatt gggatccaaa tgcagaccat atgagcaaag tatgcatgta    2760
gtttcacaaa tatatcatat tttctttgta gattttttt tttagatcgg cttatctatt    2820
acgttgagct gtaaatatag ttggaagtgt ttaggagtat taaattcact ggactctatt    2880
ctttcacttg cctgttgcac gagcccatta ctagatatca atgttgatga tgcttttgtt    2940
gtatgaggtc gaagtgaaac atgcatgtta cccttttata taagtaaggt tgcacatgta    3000 tttttatga tctaaacatt atttactgat tttgttcttg caagcacta agcagtttta     3060 cataataatg gcgttggagc aggccgactg cacatctgaa ctgtagctcc atgtggttga    3120
tatagattac aaatgctcat attcaatgta actgttttca gaatgacctt ggtgtttggg    3180
agatttttct gccaaacaat gcagatggtt cgccaccaat tcctcacggc tcacgggtga    3240
aggttgtttt cttctccttg ccaacggtgt taggctcagg aacatgtcct gtattactca    3300
gaagctcttt tgaacatcta ggtgagaatg gatactccat ctgggataaa ggattcaatt    3360
cctgcttgga tcaagtactc cgtgcagact ccaggagata taccatacaa tggaatatat    3420
tatgatcctc ccgaagaggt attttacttc atcttctgtg cttttagatt tcagatattt    3480
ttattagaag aaaattatga ttttttcccct cacgaacctt cccaattgct atttcaagct    3540
gtcctactta tttgctgctg gcatcttatt tttctattct ctaaccagtt atgaaattcc    3600
ttacatgcat atgcaggaga agtatgtatt caagcatcct caacctaaac gaccaaaatc    3660
attgcggata tatgaaacac atgttggcat gagtagcccg gtatttcatc tttaccatgt    3720
attccataaa tgaagttagc tatatgcagt tcaaatttat ttacaggttg ttacaatggt    3780
atttttgtgt tggtgccctt ctttcgtttt ataagtaaaa aacttatcat aaatttattt    3840
gttatgccgc ttggttaata caatctgaaa aatgtaactg tggacaatct agaactagat    3900
aatacaaatc tgaaaaaaca tgctggaata gtgtcatttc agtcaactag gatgttttga    3960
atgctcaaga gaagtactag tgtgtagcat caaaagctgg tgtccatttg ttcaaatgtt    4020
taattaacac tatagtgaaa acaagtaatt gcacaaagaa acaagtaatt gcccaagttc    4080
atatgttttt tcactatatt acatgtttca tcaacaattt aattaacctc attccttaca    4140
aacatttgta tttacatttg ttcctacata tatagttatt ttatatatca actttataaa    4200
tcatgactgt tataattaaa accgatggta tatcaacgat tgagataatt tggcatatgt    4260
ggatgaattt tgtggcttgt tatgctcttg ttttaataac ataataaata gattatgctt    4320
gttggtagcc tttttacatt aacacatggg caattacttg tttctttgtg caaccaggaa    4380
ccaaagatcg acacatatgc aaacttcagg gatgaggtgc ttccaagaat taaaagactt    4440
ggatacaatg cagtgcaaat aatggcaatc caagagcact catactatgg aagctttggg    4500
tagttctctg ggtcgatttc tggttctttt agttatcttg tgtccataga acatatttca    4560
actttagcaa ctatactatt atattaactt ttcagctatt gtcttncttt ttcttatgtg    4620
```

```
agagactgct gcntcttgct acttcctgtg ttctcattca gagtanacat cttatganta    4680
gacaactcta tgtngacatt ccggaagtat ncactggctg attcggtcta aaataacata    4740
ctgctcagat agccacataa cagtacgatt acacacataa tgaccatgtt tgcatagagt    4800
ggcggtagta tgttcctcac catactagca taatgacttg ttatataaga gtatatcata    4860
ttaacttctt ttccaatgac atggaagctg taacaacttt caaatcattt ttgtctttta    4920
agtgctgctt ttttcctgtt tgacaattaa tacaatacca cttttatgtg ttttttacttc    4980 tattgcaggt accatgttac caatttcttt gcaccaagta gccgttttgg gtccccagaa    5040
gatttaaaat ctttgattga tagagctcac gagcttggct tggttgtcct catggatgtt    5100
gttcacaggt acttaatgta atttgaggtt ggcgtgttaa gttcacatta atcttaattc    5160
tttatttcaa ttcctatggc ctctctccta gattggaaca gtaaaagcat catccagttt    5220
gtataaattg ctaaagaac atttacatg ttaagtattt tcaattacta tgaaacatat    5280
aaatttacat acttattgat tttacgacag aagtaccgat ctcacaagat gaacaattgg    5340
ttgatcacat atcatttcat actacaatac aagaaaatga atagaaacg agttaatatt    5400 agccttggta aaatcagcaa cttgtttgga ataaagtat agtgatgcca gtgcaaanaa    5460
caaggcatca agttggtttc agctcccacg gtcggtgcta gctgtcaagg gtaatttgca    5520
cgtagtcgca catagatttg tgtgggagtg aaagtaacc acagattgtc cgaggaacac    5580
gggacacacg tcttagccac aggtttgggc tccccttgat gcgggtagta gctttactcc    5640
ttatatgaaa ttatctcaag atagatttca atttggggtt acacttanga actcancaag    5700
ttaaggatca actcnctgag ttctatacga ctgatctttg accgagatat cttgatcagg    5760
ctaagtanca aaatccaggc cttgagatgt tgaacatgtc cttcattttg ggctgggtgc    5820
ccttgggcat aaggtgtngt ccttccttca tgtgcttctt gcagcgtatg acataaacnt    5880
cctctgagtt ggtanatgca cggttccctt tgaggaaatc aggggtagtc gcatctnggg    5940
aaagttggtc acccangcat ggatcctcng cgcacaccgg gcaaacacgg tgaaaccact    6000
tctcctcgac actagctaac ttgacattca agcaaactaa gaatataact ttatntctaa    6060
atgaaccgga caccctcctt gtgcctgcac ctacagagta caatgccagt tttggactga    6120
actcttgtgt tcatgtatgt gctaatnaca taggttctaa ccatgattct aaatagcgcg    6180
ttataactcc actatagtaa tgctatagcg tttanaagat cccgcactaa gggaccttag    6240
tccaaataca tgatcaaaca ttttacatag cgcgctatag ctatttaaaa ctatggtcac    6300
ccgctaagag gcataactcg ctatttaaaa ctatggttct aacttttaat ctattttatg    6360
tcttggtcca aagccccttt ttgttctata gctttacctt tgggttgaga tcacccttaa    6420
cccattggta atcctggttg atttactcca tcctttcttg cgtagcttta cttttggttt    6480
tttgtttctc acagtcacgc gtcaaataat accttggacg                          6520

<210> SEQ ID NO 3
<211> LENGTH: 400
<212> TYPE: DNA
<213> ORGANISM: Triticum aestivum

<400> SEQUENCE: 3
cgccagcttc cacccccgcc gcacacgttg ctccccctte tcatcgcttc tcaattaata      60
tctccatcac tcgggttccg cgctgcattt cggccggcgg gttgagtgag atctgggcca     120
ctgaccgact cactcgctcg ctgcgcgggg atggcgacgt tcgcggtgtc cggcgcgacc     180
```

-continued

| ctcggtgtgg cgcggcccgc cggcgccggc ggcggactgc tgccgcgatc cggctcggag | 240 |
| cggaggggcg gggtggacct gccgtcgctg ctcctcagga agaaggactc ctctcgcgcc | 300 |
| gtcctgagcc gcgcggcctc tccaggaag gtcctggtgc ctgacggtga gagcgacgac | 360 |
| ttggcaagtc cggcgcaacc tgaagaatta cagatacctg | 400 |

<210> SEQ ID NO 4
<211> LENGTH: 279
<212> TYPE: DNA
<213> ORGANISM: Triticum aestivum

<400> SEQUENCE: 4

| gccactgacc gactcactcg ctcgctgcgc ggggatggcg acgtttgcgg tgtccggcgc | 60 |
| gacccctcggt gtggcgcggc cgccggcgc cggcggcgga ctgctgccgc gatccggctc | 120 |
| ggagcggagg ggcggggtgg acctgccgtc gctgctcctc aggaagaagg actcctctcg | 180 |
| cgccgtcctg agccgcgcgg cctctccagg gaaggtcctg gtgcctgacg gtgagagcga | 240 |
| cgacttggca agtccggcgc aacctgaaga attacagat | 279 |

<210> SEQ ID NO 5
<211> LENGTH: 273
<212> TYPE: DNA
<213> ORGANISM: Triticum aestivum

<400> SEQUENCE: 5

| ggcggggttga gtgagatctg ggcgactggc tgactcaatc actacgcggg gatggcgacg | 60 |
| ttcgcggtgt ccggcgcgac tcggtgtg gcgcgggccg gcgtcggagt ggcgcgggcc | 120 |
| ggctcggagc ggaggggcgg ggcggacttg ccgtcgctgc tcctcaggaa gaaggactcc | 180 |
| tctcgcgccg tcctgagccg cgcggcctct ccagggaagg tcctggtgcc tgacggcgag | 240 |
| agcgacgact gcaagtccg gcgcaacctg aag | 273 |

<210> SEQ ID NO 6
<211> LENGTH: 208
<212> TYPE: DNA
<213> ORGANISM: Triticum aestivum

<400> SEQUENCE: 6

| acgttgctcc cccttctcat cgcttctcaa ttaatatctc catcactcgg ttccgcgctg | 60 |
| catttcggcc ggcggttga gtgagatctg ggccactgac cgactcactc gctcgctgcg | 120 |
| gggatggcga cgttcgcggt gtccggcgcg acccctcggtg tggcgcggcc gccggcggcg | 180 |
| gcgcaacctg aagaattaca gatacctg | 208 |

<210> SEQ ID NO 7
<211> LENGTH: 818
<212> TYPE: PRT
<213> ORGANISM: Triticum aestivum

<400> SEQUENCE: 7

Met Ala Thr Phe Ala Val Ser Gly Ala Thr Leu Gly Val Ala Arg Ala
1               5                   10                  15

Gly Val Gly Val Ala Arg Ala Gly Ser Glu Arg Arg Gly Gly Ala Asp
            20                  25                  30

Leu Pro Ser Leu Leu Leu Arg Lys Lys Asp Ser Ser Arg Ala Val Leu
        35                  40                  45

Ser Arg Ala Ala Ser Pro Gly Lys Val Leu Val Pro Asp Gly Glu Ser
    50                  55                  60

-continued

```
Asp Asp Leu Ala Ser Pro Ala Gln Pro Glu Glu Leu Gln Ile Pro Glu
 65                  70                  75                  80

Asp Ile Glu Glu Gln Thr Ala Glu Val Asn Met Thr Gly Gly Thr Ala
                 85                  90                  95

Glu Lys Leu Gln Ser Ser Glu Pro Thr Gln Gly Ile Val Glu Thr Ile
            100                 105                 110

Thr Asp Gly Val Thr Lys Gly Val Lys Glu Leu Val Val Gly Glu Lys
        115                 120                 125

Pro Arg Val Val Pro Lys Pro Gly Asp Gly Gln Lys Ile Tyr Glu Ile
    130                 135                 140

Asp Pro Thr Leu Lys Asp Phe Arg Ser His Leu Asp Tyr Arg Tyr Ser
145                 150                 155                 160

Glu Tyr Lys Arg Ile Arg Ala Ala Ile Asp Gln His Glu Gly Gly Leu
                165                 170                 175

Glu Ala Phe Ser Arg Gly Tyr Glu Lys Leu Gly Phe Thr Arg Ser Ala
            180                 185                 190

Glu Gly Ile Thr Tyr Arg Glu Trp Ala Pro Gly Ala His Ser Ala Ala
        195                 200                 205

Leu Val Gly Asp Phe Asn Asn Trp Asn Pro Asn Ala Asp Thr Met Thr
    210                 215                 220

Arg Asp Asp Tyr Gly Val Trp Glu Ile Phe Leu Pro Asn Asn Ala Asp
225                 230                 235                 240

Gly Ser Ser Ala Ile Pro His Gly Ser Arg Val Lys Ile Arg Met Asp
                245                 250                 255

Thr Pro Ser Gly Val Lys Asp Ser Ile Ser Ala Trp Ile Lys Phe Ser
            260                 265                 270

Val Gln Ala Pro Gly Glu Ile Pro Phe Asn Gly Ile Tyr Tyr Asp Pro
        275                 280                 285

Pro Glu Glu Lys Tyr Val Phe Gln His Pro Gln Arg Lys Arg Pro Glu
    290                 295                 300

Ser Leu Arg Ile Tyr Glu Ser His Ile Gly Met Ser Ser Pro Glu Pro
305                 310                 315                 320

Lys Ile Asn Ser Tyr Ala Asn Phe Arg Asp Glu Val Leu Pro Arg Ile
                325                 330                 335

Lys Arg Leu Gly Tyr Asn Ala Val Gln Ile Met Ala Ile Gln Glu His
            340                 345                 350

Ser Tyr Tyr Ala Ser Phe Gly Tyr His Val Thr Asn Phe Phe Ala Pro
        355                 360                 365

Ser Ser Arg Phe Gly Thr Pro Glu Asp Leu Lys Ser Leu Ile Asp Arg
    370                 375                 380

Ala His Glu Leu Gly Leu Leu Val Leu Met Asp Ile Val His Ser His
385                 390                 395                 400

Ser Ser Asn Asn Thr Leu Asp Gly Leu Asn Gly Phe Asp Gly Thr Asp
                405                 410                 415

Thr His Tyr Phe His Gly Gly Pro Arg Gly His His Trp Met Trp Asp
            420                 425                 430

Ser Arg Leu Phe Asn Tyr Gly Ser Trp Glu Val Leu Arg Phe Leu Leu
        435                 440                 445

Ser Asn Ala Arg Trp Trp Leu Glu Glu Tyr Lys Phe Asp Gly Phe Arg
    450                 455                 460

Phe Asp Gly Val Thr Ser Met Met Tyr Thr His His Gly Leu Gln Met
465                 470                 475                 480
```

```
Thr Phe Thr Gly Asn Tyr Gly Glu Tyr Phe Gly Phe Ala Thr Asp Val
            485                 490                 495

Asp Ala Val Val Tyr Leu Met Leu Val Asn Asp Leu Ile His Gly Leu
            500                 505                 510

Tyr Pro Asp Ala Val Ser Ile Gly Glu Asp Val Ser Gly Met Pro Thr
            515                 520                 525

Phe Cys Ile Pro Val Pro Asp Gly Gly Val Gly Phe Asp Tyr Arg Leu
            530                 535                 540

His Met Ala Val Ala Asp Lys Trp Ile Glu Leu Leu Lys Gln Ser Asp
545                 550                 555                 560

Glu Ser Trp Lys Met Gly Asp Ile Val His Thr Leu Thr Asn Arg Arg
            565                 570                 575

Trp Leu Glu Lys Cys Val Thr Tyr Ala Glu Ser His Asp Gln Ala Leu
            580                 585                 590

Val Gly Asp Lys Thr Ile Ala Phe Trp Leu Met Asp Lys Asp Met Tyr
            595                 600                 605

Asp Phe Met Ala Leu Asp Arg Pro Ser Thr Leu Arg Ile Asp Arg Gly
            610                 615                 620

Ile Ala Leu His Lys Met Ile Arg Leu Val Thr Met Gly Leu Gly Gly
625                 630                 635                 640

Glu Gly Tyr Leu Asn Phe Met Gly Asn Glu Phe Gly His Pro Glu Trp
            645                 650                 655

Ile Asp Phe Pro Arg Gly Pro Gln Thr Leu Pro Thr Gly Lys Val Leu
            660                 665                 670

Pro Gly Asn Asn Asn Ser Tyr Asp Lys Cys Arg Arg Phe Asp Leu
            675                 680                 685

Val Asn Ala Asp Phe Leu Arg Tyr Arg Gly Met Gln Glu Phe Asp Gln
            690                 695                 700

Ala Met Gln His Leu Glu Glu Lys Tyr Gly Phe Met Thr Ser Glu His
705                 710                 715                 720

Gln Tyr Val Ser Arg Lys His Glu Glu Asp Lys Val Ile Ile Leu Lys
            725                 730                 735

Arg Gly Asp Leu Val Phe Val Phe Asn Phe His Trp Ser Asn Ser Phe
            740                 745                 750

Phe Asp Tyr Arg Val Gly Cys Ser Lys Pro Gly Lys Tyr Lys Val Ala
            755                 760                 765

Leu Asp Ser Asp Asp Ala Leu Phe Gly Gly Phe Ser Arg Leu Asp His
            770                 775                 780

Asp Val Asp Tyr Phe Thr Thr Glu His Pro His Asp Asn Arg Pro Arg
785                 790                 795                 800

Ser Phe Ser Val Tyr Thr Pro Ser Arg Thr Ala Val Val Tyr Ala Leu
            805                 810                 815

Thr Glu

<210> SEQ ID NO 8
<211> LENGTH: 823
<212> TYPE: PRT
<213> ORGANISM: Triticum aestivum

<400> SEQUENCE: 8

Met Ala Thr Phe Ala Val Ser Gly Ala Thr Leu Gly Val Ala Arg Pro
1               5                   10                  15

Ala Gly Ala Gly Gly Gly Leu Leu Pro Arg Ser Gly Ser Glu Arg Arg
            20                  25                  30
```

-continued

```
Gly Gly Val Asp Leu Pro Ser Leu Leu Arg Lys Lys Asp Ser Ser
         35                  40                  45

Arg Ala Val Leu Ser Arg Ala Ala Ser Pro Gly Lys Val Leu Val Pro
 50                  55                  60

Asp Gly Glu Ser Asp Leu Ala Ser Pro Ala Gln Pro Glu Glu Leu
 65                  70                  75                  80

Gln Ile Pro Glu Asp Ile Glu Glu Gln Thr Ala Glu Val Asn Met Thr
                     85                  90                  95

Gly Gly Thr Ala Glu Lys Leu Glu Ser Ser Glu Pro Thr Gln Gly Ile
             100                 105                 110

Val Glu Thr Ile Thr Asp Gly Val Thr Lys Gly Val Lys Glu Leu Val
             115                 120                 125

Val Gly Glu Lys Pro Arg Val Val Pro Lys Pro Gly Asp Gly Gln Lys
 130                 135                 140

Ile Tyr Glu Ile Asp Pro Thr Leu Lys Asp Phe Arg Ser His Leu Asp
145                 150                 155                 160

Tyr Arg Tyr Ser Glu Tyr Arg Arg Ile Arg Ala Ala Ile Asp Gln His
                 165                 170                 175

Glu Gly Gly Leu Glu Ala Phe Ser Arg Gly Tyr Glu Lys Leu Gly Phe
             180                 185                 190

Thr Arg Ser Ala Glu Gly Ile Thr Tyr Arg Glu Trp Ala Pro Gly Ala
         195                 200                 205

His Ser Ala Ala Leu Val Gly Asp Phe Asn Asn Trp Asn Pro Asn Ala
210                 215                 220

Asp Thr Met Thr Arg Asp Asp Tyr Gly Val Trp Glu Ile Phe Leu Pro
225                 230                 235                 240

Asn Asn Ala Asp Gly Ser Pro Ala Ile Pro His Gly Ser Arg Val Lys
                 245                 250                 255

Ile Arg Met Asp Thr Pro Ser Gly Val Lys Asp Ser Ile Ser Ala Trp
             260                 265                 270

Ile Lys Phe Ser Val Gln Ala Pro Gly Glu Ile Pro Phe Asn Gly Ile
         275                 280                 285

Tyr Tyr Asp Pro Pro Glu Glu Lys Tyr Val Phe Gln His Pro Gln
290                 295                 300

Pro Lys Arg Pro Glu Ser Leu Arg Ile Tyr Glu Ser His Ile Gly Met
305                 310                 315                 320

Ser Ser Pro Glu Pro Lys Ile Asn Ser Tyr Ala Asn Phe Arg Asp Glu
                 325                 330                 335

Val Leu Pro Arg Ile Lys Arg Leu Gly Tyr Asn Ala Val Gln Ile Met
             340                 345                 350

Ala Ile Gln Glu His Ser Tyr Tyr Ala Ser Phe Gly Tyr His Val Thr
         355                 360                 365

Asn Phe Phe Ala Pro Ser Ser Arg Phe Gly Thr Pro Glu Asp Leu Lys
370                 375                 380

Ser Leu Ile Asp Arg Ala His Glu Leu Gly Leu Leu Val Leu Met Asp
385                 390                 395                 400

Ile Val His Ser His Ser Ser Asn Asn Thr Leu Asp Gly Leu Asn Gly
                 405                 410                 415

Phe Asp Gly Thr Asp Thr His Tyr Phe His Gly Gly Pro Arg Gly His
             420                 425                 430

His Trp Met Trp Asp Ser Arg Leu Phe Asn Tyr Gly Ser Trp Glu Val
         435                 440                 445

Leu Arg Phe Leu Leu Ser Asn Ala Arg Trp Trp Leu Glu Glu Tyr Lys
```

-continued

```
            450                 455                 460
Phe Asp Gly Phe Arg Phe Asp Gly Val Thr Ser Met Met Tyr Thr His
465                 470                 475                 480

His Gly Leu Gln Met Thr Phe Thr Gly Asn Tyr Gly Glu Tyr Phe Gly
                485                 490                 495

Phe Ala Thr Asp Val Asp Ala Val Val Tyr Leu Met Leu Val Asn Asp
            500                 505                 510

Leu Ile His Gly Leu His Pro Asp Ala Val Ser Ile Gly Glu Asp Val
        515                 520                 525

Ser Gly Met Pro Thr Phe Cys Ile Pro Val Pro Asp Gly Gly Val Gly
530                 535                 540

Leu Asp Tyr Arg Leu His Met Ala Val Ala Asp Lys Trp Ile Glu Leu
545                 550                 555                 560

Leu Lys Gln Ser Asp Glu Ser Trp Lys Met Gly Asp Ile Val His Thr
                565                 570                 575

Leu Thr Asn Arg Arg Trp Leu Glu Lys Cys Val Thr Tyr Ala Glu Ser
            580                 585                 590

His Asp Gln Ala Leu Val Gly Asp Lys Thr Ile Ala Phe Trp Leu Met
        595                 600                 605

Asp Lys Asp Met Tyr Asp Phe Met Ala Leu Asp Arg Pro Ser Thr Pro
610                 615                 620

Arg Ile Asp Arg Gly Ile Ala Leu His Lys Met Ile Arg Leu Val Thr
625                 630                 635                 640

Met Gly Leu Gly Gly Glu Gly Tyr Leu Asn Phe Met Gly Asn Glu Phe
                645                 650                 655

Gly His Pro Glu Trp Ile Asp Phe Pro Arg Gly Pro Gln Thr Leu Pro
            660                 665                 670

Thr Gly Lys Val Leu Pro Gly Asn Asn Asn Ser Tyr Asp Lys Cys Arg
        675                 680                 685

Arg Arg Phe Asp Leu Gly Asp Ala Asp Phe Leu Arg Tyr His Gly Met
690                 695                 700

Gln Glu Phe Asp Gln Ala Met Gln His Leu Glu Glu Lys Tyr Gly Phe
705                 710                 715                 720

Met Thr Ser Glu His Gln Tyr Val Ser Arg Lys His Glu Glu Asp Lys
                725                 730                 735

Val Ile Ile Phe Glu Arg Gly Asp Leu Val Phe Val Phe Asn Phe His
            740                 745                 750

Trp Ser Asn Ser Phe Phe Asp Tyr Arg Val Gly Cys Ser Arg Pro Gly
        755                 760                 765

Lys Tyr Lys Val Ala Leu Asp Ser Asp Ala Leu Phe Gly Gly Phe
770                 775                 780

Ser Arg Leu Asp His Asp Val Asp Tyr Phe Thr Thr Glu His Pro His
785                 790                 795                 800

Asp Asn Arg Pro Arg Ser Phe Ser Val Tyr Thr Pro Ser Arg Thr Ala
                805                 810                 815

Val Val Tyr Ala Leu Thr Glu
            820
```

<210> SEQ ID NO 9
<211> LENGTH: 22
<212> TYPE: DNA
<213> ORGANISM: Artificial Sequence
<220> FEATURE:
<223> OTHER INFORMATION: Primer

```
<400> SEQUENCE: 9
cccgctgctt tcgctcattt tg                                              22

<210> SEQ ID NO 10
<211> LENGTH: 22
<212> TYPE: DNA
<213> ORGANISM: Artificial Sequence
<220> FEATURE:
<223> OTHER INFORMATION: Primer

<400> SEQUENCE: 10
gactaccgga gctcccacct tc                                              22

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11
agatgtgaat ggctgcttgc tg                                              22

<210> SEQ ID NO 12
<211> LENGTH: 22
<212> TYPE: DNA
<213> ORGANISM: Artificial Sequence
<220> FEATURE:
<223> OTHER INFORMATION: Primer

<400> SEQUENCE: 12
caggtcgacc atatgggaga gc                                              22

<210> SEQ ID NO 13
<211> LENGTH: 18
<212> TYPE: PRT
<213> ORGANISM: Artificial Sequence
<220> FEATURE:
<223> OTHER INFORMATION: synthetic peptide

<400> SEQUENCE: 13

Ala Ala Ser Pro Gly Lys Val Leu Val Pro Asp Glu Ser Asp Asp Leu
1               5                   10                  15

Gly Cys

<210> SEQ ID NO 14
<211> LENGTH: 12
<212> TYPE: PRT
<213> ORGANISM: Artificial Sequence
<220> FEATURE:
<223> OTHER INFORMATION: synthetic peptide

<400> SEQUENCE: 14

Ala Gly Gly Pro Ser Gly Glu Val Met Ile Gly Cys
1               5                   10

<210> SEQ ID NO 15
<211> LENGTH: 19
<212> TYPE: DNA
<213> ORGANISM: Artificial Sequence
<220> FEATURE:
<223> OTHER INFORMATION: Primer

<400> SEQUENCE: 15
atcacttacc gagaatggg                                                  19
```

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
ctgcatttgg attccaattg                                        20

<210> SEQ ID NO 17
<211> LENGTH: 24
<212> TYPE: DNA
<213> ORGANISM: Artificial Sequence
<220> FEATURE:
<223> OTHER INFORMATION: Primer

<400> SEQUENCE: 17
cacccattgt aattgggtac actg                                   24

<210> SEQ ID NO 18
<211> LENGTH: 24
<212> TYPE: DNA
<213> ORGANISM: Artificial Sequence
<220> FEATURE:
<223> OTHER INFORMATION: Primer

<400> SEQUENCE: 18
tccatgcctc cttcgtgttc atca                                   24

<210> SEQ ID NO 19
<211> LENGTH: 24
<212> TYPE: DNA
<213> ORGANISM: Artificial Sequence
<220> FEATURE:
<223> OTHER INFORMATION: Primer

<400> SEQUENCE: 19
ctgcgcataa atccaaactt ctcg                                   24

<210> SEQ ID NO 20
<211> LENGTH: 23
<212> TYPE: DNA
<213> ORGANISM: Artificial Sequence
<220> FEATURE:
<223> OTHER INFORMATION: Primer

<400> SEQUENCE: 20
ctatgccaat tgaacaacaa tgc                                    23

<210> SEQ ID NO 21
<211> LENGTH: 22
<212> TYPE: DNA
<213> ORGANISM: Artificial Sequence
<220> FEATURE:
<223> OTHER INFORMATION: Primer

<400> SEQUENCE: 21
cgtgttcatc aatgtctgaa cg                                     22

<210> SEQ ID NO 22
<211> LENGTH: 20
<212> TYPE: DNA
<213> ORGANISM: Artificial Sequence
<220> FEATURE:

<223> OTHER INFORMATION: Primer

<400> SEQUENCE: 22
ggatatgtat gatttcatgg                                           20

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
ccataaagtt aagataaccc                                           20

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
gacatcagac caccagtacg                                           20

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
cttcccaggc tttaaacagc                                           20

<210> SEQ ID NO 26
<211> LENGTH: 30
<212> TYPE: DNA
<213> ORGANISM: Artificial Sequence
<220> FEATURE:
<223> OTHER INFORMATION: Primer

<400> SEQUENCE: 26
ggtaccgcag aaaatatacg agattgaccc                                30

<210> SEQ ID NO 27
<211> LENGTH: 19
<212> TYPE: DNA
<213> ORGANISM: Artificial Sequence
<220> FEATURE:
<223> OTHER INFORMATION: Primer

<400> SEQUENCE: 27
atcacttacc gagaatggg                                            19

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
ctgcatttgg attccaattg                                           20

```
<210> SEQ ID NO 29
<211> LENGTH: 21
<212> TYPE: DNA
<213> ORGANISM: Artificial Sequence
<220> FEATURE:
<223> OTHER INFORMATION: Primer

<400> SEQUENCE: 29
ccaagtacca gtggtgaacg c                                              21

<210> SEQ ID NO 30
<211> LENGTH: 19
<212> TYPE: DNA
<213> ORGANISM: Artificial Sequence
<220> FEATURE:
<223> OTHER INFORMATION: Primer

<400> SEQUENCE: 30
cggtgggatc caacggccc                                                 19

<210> SEQ ID NO 31
<211> LENGTH: 21
<212> TYPE: DNA
<213> ORGANISM: Artificial Sequence
<220> FEATURE:
<223> OTHER INFORMATION: Primer

<400> SEQUENCE: 31
catgtgagct agctttcgcc c                                              21

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
gggcaaacgg aatctgatcc                                                20

<210> SEQ ID NO 33
<211> LENGTH: 23
<212> TYPE: DNA
<213> ORGANISM: Artificial Sequence
<220> FEATURE:
<223> OTHER INFORMATION: Primer

<400> SEQUENCE: 33
ccagatcgta tatcggaagg tcg                                            23

<210> SEQ ID NO 34
<211> LENGTH: 27
<212> TYPE: DNA
<213> ORGANISM: Artificial Sequence
<220> FEATURE:
<223> OTHER INFORMATION: Primer

<400> SEQUENCE: 34
gcaaaagcca gatcataaat ttagagc                                        27

<210> SEQ ID NO 35
<211> LENGTH: 27
<212> TYPE: DNA
<213> ORGANISM: Artificial Sequence
<220> FEATURE:
<223> OTHER INFORMATION: Primer
```

```
<400> SEQUENCE: 35
cttccaattc attgttaatg gtcacac                                                27
```

The invention claimed is:

1. A wheat grain comprising wheat endosperm having starch and DNA which encodes a double-stranded RNA molecule comprising nucleotides in a sequence which corresponds to a sequence of at least 30 contiguous nucleotides of an exon of the starch branching enzyme IIa (SBEIIa) gene whose sequence is set forth in SEQ ID NO: 1 and the complement thereof, which inhibits expression of SBEIIa, wherein the proportion of amylose of the starch of the wheat endosperm is at least 40% (w/w) as determined by an iodometric method.

2. The wheat grain of claim 1, wherein the proportion of amylose in the starch of the wheat endosperm is at least 60%.

3. The wheat grain of claim 1 which is non-shrunken.

4. The wheat grain of claim 1 which has an average weight of at least 36 mg.

5. The wheat grain of claim 4 which has an average weight of at least 40 mg.

6. The wheat grain of claim 1, wherein at least 50% of starch granules within the grain appear non-birefringent when observed under polarized light.

7. The wheat grain of claim 1, wherein the starch content of the grain when naked is at least 25% (w/w).

8. The wheat grain of claim 7, wherein the starch content of the grain when naked is at least 35% (w/w).

9. The wheat grain of claim 1, wherein the wheat grain comprises an altered level of ADP glucose pyrophosphorylase, GBSS, SSI, SSII, SSIII, SBEIIb, a debranching enzyme of an isoamylase type or a debranching enzyme of a pullulanase type.

10. The wheat grain of claim 9, wherein the wheat grain comprises a reduced level of SBEIIb.

11. The wheat grain of claim 1 which is whole grain.

12. The wheat grain of claim 1 in combination with a food ingredient.

13. The wheat grain of any one of claims 1 or 11 or 12, wherein the wheat grain has a reduced level of SBEIIa activity as compared to the NB1 wheat variety.

14. The wheat grain of any one of claims 1 or 11 or 12, wherein the wheat grain lacks a detectable level of SBEIIa protein in the wheat endosperm as determinable by Western blot analysis.

15. A wheat plant comprising the wheat grain of claim 1.

16. The wheat plant of claim 15 which is *Triticum aestivum* ssp. *aestivum*.

17. A process of producing a wheat grain comprising wheat endosperm having starch, DNA which encodes a double-stranded hairpin RNA molecule comprising nucleotides in a sequence which corresponds to a sequence of at least 30 contiguous nucleotides of an exon of the starch branching enzyme IIa (SBEIIa) gene whose sequence is set forth in SEQ ID NO: 1 and the complement thereof, which inhibits expression of SBEIIa, and which wheat grain has a proportion of amylose of at least 40% (w/w) in the starch of the wheat endosperm as determined by an iodometric method, comprising the steps of growing a wheat plant that produces the wheat grain, and harvesting the wheat grain from the wheat plant.

18. The wheat grain of claim 1, wherein the double-stranded RNA molecule is a hairpin RNA molecule.

19. The wheat grain of claim 18, wherein the proportion of amylose in the starch of the wheat endosperm is at least 60%.

20. The wheat grain of claim 18 which is non-shrunken.

21. The wheat grain of claim 18 which has an average weight of at least 36 mg.

22. The wheat grain of claim 21 which has an average weight of at least 40 mg.

23. The wheat grain of claim 18, wherein at least 50% of starch granules within the grain appear non-birefringent when observed under polarized light.

24. The wheat grain of claim 18, wherein the starch content of the grain when naked is at least 25% (w/w).

25. The wheat grain of claim 24, wherein the starch content of the grain when naked is at least 35% (w/w).

26. The wheat grain of claim 18, wherein the wheat grain comprises an altered level of ADP glucose pyrophosphorylase, GBSS, SSI, SSII, SSIII, SBEIIb, a debranching enzyme of an isoamylase type or a debranching enzyme of a pullulanase type.

27. The wheat grain of claim 18 which is whole grain.

28. A wheat plant comprising the wheat grain of claim 18.

29. The wheat plant of claim 28 which is *Triticum aestivum* ssp. *aestivum*.

30. The wheat grain of any one of claims 18 or 27, wherein the wheat grain lacks a detectable level of SBEIIa protein in the wheat endosperm as determinable by Western blot analysis.

31. The wheat grain of claim 1, wherein the sequence of at least 30 contiguous nucleotides of an exon of the starch branching enzyme IIa (SBEIIa) gene whose sequence is set forth in SEQ ID NO: 1 is derived from the 5' untranslated region of the SBEIIa gene.

32. The wheat grain of claim 18, wherein the sequence of at least 30 contiguous nucleotides of an exon of the starch branching enzyme IIa (SBEIIa) gene whose sequence is set forth in SEQ ID NO: 1 is derived from the 5' untranslated region of the SBEIIa gene.

* * * * *